US009957267B2

(12) United States Patent
Zhu et al.

(10) Patent No.: US 9,957,267 B2
(45) Date of Patent: May 1, 2018

(54) SOMATOSTATIN MODULATORS AND USES THEREOF

(71) Applicant: Crinetics Pharmaceuticals, Inc., San Diego, CA (US)

(72) Inventors: Yunfei Zhu, San Diego, CA (US); Jian Zhao, San Diego, CA (US); Zhiyong Chen, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 0 days. days.

(21) Appl. No.: 15/186,086

(22) Filed: Jun. 17, 2016

(65) Prior Publication Data

US 2017/0002001 A1 Jan. 5, 2017

Related U.S. Application Data

(60) Provisional application No. 62/187,604, filed on Jul. 1, 2015.

(51) Int. Cl.
*C07D 471/04* (2006.01)

(52) U.S. Cl.
CPC .................. *C07D 471/04* (2013.01)

(58) Field of Classification Search
None
See application file for complete search history.

(56) References Cited

U.S. PATENT DOCUMENTS

| | | | |
|---|---|---|---|
| 5,952,328 | A | 9/1999 | Bihovsky et al. |
| 5,962,457 | A | 10/1999 | Chenard et al. |
| 6,011,036 | A | 1/2000 | Lohray et al. |
| 6,136,812 | A | 10/2000 | Chenard et al. |
| 6,323,208 | B1 | 11/2001 | Chenard et al. |
| 6,667,300 | B2 | 12/2003 | Sadhu et al. |
| 6,730,682 | B2 | 5/2004 | Schnute et al. |
| 7,034,039 | B2 | 4/2006 | Oi et al. |
| 7,226,923 | B2 | 6/2007 | Boyd et al. |
| 7,501,410 | B2 | 3/2009 | Goldstein et al. |
| 7,696,215 | B2 | 4/2010 | Nash et al. |
| 7,737,155 | B2 | 6/2010 | Palani et al. |
| 7,737,274 | B2 | 6/2010 | Kataoka et al. |
| 7,750,015 | B2 | 7/2010 | Palani et al. |
| 7,750,154 | B2 | 7/2010 | Brown et al. |
| 7,786,115 | B2 | 8/2010 | Nash et al. |
| 7,939,539 | B2 | 5/2011 | Wang et al. |
| 7,960,384 | B2 | 6/2011 | Feng et al. |
| 8,188,117 | B2 | 5/2012 | Plettenburg et al. |
| 8,207,163 | B2 | 6/2012 | Bhat et al. |
| 8,530,499 | B2 | 9/2013 | Cheruvallath et al. |
| 8,541,403 | B2 | 9/2013 | Chu et al. |
| 8,604,032 | B2 | 12/2013 | Ren et al. |
| 8,609,691 | B2 | 12/2013 | Plettenburg et al. |
| 8,618,129 | B2 | 12/2013 | Kuehnert et al. |
| 8,637,533 | B2 | 1/2014 | Sadhu et al. |
| 8,815,901 | B2 | 8/2014 | Furet et al. |
| 8,969,363 | B2 | 3/2015 | Castro et al. |
| 2005/0033050 | A1 | 2/2005 | Kruger et al. |
| 2005/0043239 | A1 | 2/2005 | Douangpanya et al. |
| 2005/0054614 | A1 | 3/2005 | Diacovo et al. |
| 2006/0079538 | A1 | 4/2006 | Hallahan et al. |
| 2006/0106038 | A1 | 5/2006 | Bouscary et al. |
| 2007/0010537 | A1 | 1/2007 | Hamamura et al. |
| 2007/0135454 | A1 | 6/2007 | Bayliss et al. |
| 2008/0287469 | A1 | 11/2008 | Diacovo et al. |
| 2009/0209562 | A1 | 8/2009 | Nagase et al. |
| 2009/0233947 | A1 | 9/2009 | Bayliss et al. |
| 2009/0298856 | A1 | 12/2009 | Brown |
| 2010/0256120 | A1 | 10/2010 | Brown et al. |
| 2010/0267767 | A1 | 10/2010 | Narayanan et al. |
| 2011/0065671 | A1 | 3/2011 | Harris et al. |
| 2011/0065676 | A1 | 3/2011 | Perelman et al. |
| 2011/0071148 | A1 | 3/2011 | Ding et al. |
| 2011/0152242 | A1 | 6/2011 | Bayliss et al. |
| 2011/0294803 | A1 | 12/2011 | Law et al. |
| 2013/0053365 | A1 | 2/2013 | Wang et al. |
| 2013/0190309 | A1 | 7/2013 | Vu |
| 2013/0289027 | A1 | 10/2013 | De La Rosa et al. |
| 2014/0179718 | A1 | 6/2014 | Evarts et al. |
| 2014/0302987 | A1 | 10/2014 | Frackenpohl et al. |
| 2014/0371246 | A1 | 12/2014 | Evarts et al. |

FOREIGN PATENT DOCUMENTS

| | | |
|---|---|---|
| CA | 2644929 A1 | 5/2008 |
| WO | WO-9710221 A1 | 3/1997 |
| WO | WO-9722594 A1 | 6/1997 |
| WO | WO-9811438 A1 | 3/1998 |
| WO | WO-9938850 A1 | 8/1999 |

(Continued)

OTHER PUBLICATIONS

The Organic Chemistry of Drug Design and Drug Action, Silverman, Academic Press, 1992, pp. 352-355.*
Dishington et al., Tetrahedron Letters 45 (2004) 3733-3735.*
Berge et al. Pharmaceutical Salts. Journal of Pharmaceutical Sciences 66(1):1-19 (Jan. 1977).
Brazeau et al. Hypothalamic polypeptide that inhibits the secretion of immunoreactive pituitary growth hormone. Science 179:77-79 (1973).
Esch et al. Primary structure of ovine hypothalamic somatostatin-28 and somatostatin-25. PNAS USA 77:6827-6831 (1980).
Patel et al. Somatostatin receptors. Trends Endocrinol Metab 8:398-405 (1997).
PCT/US2016/038154 International Search Report and Written Opinion dated Sep. 23, 2016.
Pradayrol et al. N-terminally extended somatostatin: the primary structure of somatostatin-28. FEBS Letters 109:55-58 (1980).

(Continued)

*Primary Examiner* — Karl J Puttlitz
(74) *Attorney, Agent, or Firm* — Wilson Sonsini Goodrich & Rosati

(57) ABSTRACT

Described herein are compounds that are somatostatin modulators, methods of making such compounds, pharmaceutical compositions and medicaments comprising such compounds, and methods of using such compounds in the treatment of conditions, diseases, or disorders that would benefit from modulation of somatostatin activity.

22 Claims, No Drawings

(56) References Cited

FOREIGN PATENT DOCUMENTS

| | | |
|---|---|---|
| WO | WO-0055153 A1 | 9/2000 |
| WO | WO-0130768 A1 | 5/2001 |
| WO | WO-0181346 A2 | 11/2001 |
| WO | WO-03043995 A1 | 5/2003 |
| WO | WO-03070701 A2 | 8/2003 |
| WO | WO-2005016348 A1 | 2/2005 |
| WO | WO-2005030729 A1 | 4/2005 |
| WO | WO-2005067901 A2 | 7/2005 |
| WO | WO-2005120511 A1 | 12/2005 |
| WO | WO-2006026597 A2 | 3/2006 |
| WO | WO-2006062981 A2 | 6/2006 |
| WO | WO-2006102610 A2 | 9/2006 |
| WO | WO-2006124490 A2 | 11/2006 |
| WO | WO-2007056167 A2 | 5/2007 |
| WO | WO-2007149031 A1 | 12/2007 |
| WO | WO-2008051272 A2 | 5/2008 |
| WO | WO-2009015179 A1 | 1/2009 |
| WO | WO-2010017055 A2 | 2/2010 |
| WO | WO-2010037129 A1 | 4/2010 |
| WO | WO-2010060937 A2 | 6/2010 |
| WO | WO-2010149786 A1 | 12/2010 |
| WO | WO-2011019651 A1 | 2/2011 |
| WO | WO-2012011591 A1 | 1/2012 |
| WO | WO-2012166151 A1 | 12/2012 |
| WO | WO-2013068470 A1 | 5/2013 |
| WO | WO-2017003723 A1 | 1/2017 |

OTHER PUBLICATIONS

Reisine et al. Molecular biology of somatostatin receptors. Endocr Rev 16:427-442 (1995).

Wolkenberg et al. Design, synthesis, and evaluation of novel 3,6-diaryl-4-aminoalkoxyquinolines as selective agonists of somatostatin receptor subtype 2. J Med Chem xxx:000 (8 pgs) (2010).

\* cited by examiner

SOMATOSTATIN MODULATORS AND USES THEREOF

RELATED APPLICATIONS

This application claims the benefit of U.S. Provisional Patent Application No. 62/187,604 filed on Jul. 1, 2015, which is incorporated herein by reference in its entirety.

STATEMENT AS TO FEDERALLY SPONSORED RESEARCH

This invention was made with the support of the United States government under SBIR Grant No. 1R43DK088501-01A1, 1R44NS092231-01, 2R44DK088501-02A1, and 1R43EY024185-01 by the National Institutes of Health.

FIELD OF THE INVENTION

Described herein are compounds that are somatostatin modulators, methods of making such compounds, pharmaceutical compositions and medicaments comprising such compounds, and methods of using such compounds in the treatment of conditions, diseases, or disorders that would benefit from modulating somatostatin activity.

BACKGROUND OF THE INVENTION

Somatostatin is a peptide hormone that regulates the endocrine system and affects neurotransmission and cell proliferation via interaction with G-protein-coupled somatostatin receptors and inhibition of the release of numerous secondary hormones. Six subtype somatostatin receptor proteins have been identified (SSTR1, SSTR2a, SSTR2b, SSTR3, SSTR4, SSTR5) and are encoded by five different somatostatin receptor genes. Modulation of a particular subtype somatostatin receptor, or combination thereof, is attractive for the treatment of conditions, diseases, or disorders that would benefit from modulating somatostatin activity.

SUMMARY OF THE INVENTION

Compounds described herein are somatostatin modulator compounds. In some embodiments, compounds described herein modulate one or more of the subtype somatostatin receptor proteins. In some embodiments, compounds described herein modulate two or more of the subtype somatostatin receptor proteins.

Somatostatin peptide analogs, such as octreotide and pasirotide, formulated as depot injections, are routinely used to normalize hormone levels for the treatment of GH secreting adenomas, pancreatic neuroendocrine tumors, and carcinoid tumors. Unfortunately, these analogs are only effective in about half of acromegalic patients with GH adenomas, and patients with carcinoid tumors frequently become resistant to therapy. In addition, these peptide drugs are extremely expensive and require frequent doctor's office visits for painful injections that can lead to injection site reactions. Compounds described herein are molecules that are structurally different from peptide analogs. The compounds described herein are somatostatin modulators.

In one aspect, described herein is a compound of Formula (A), or a pharmaceutically acceptable salt, pharmaceutically acceptable solvate, diastereomeric mixture, enantiomer or prodrug thereof:

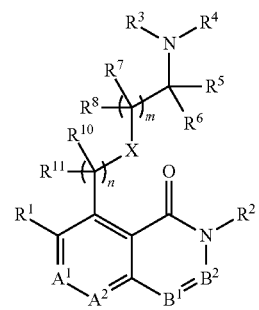

Formula (A)

wherein:

$A^1$ and $A^2$ are independently N or $CR^A$, provided that $A^1$ and $A^2$ are not N at the same time;

each $R^A$ is independently hydrogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —$CO_2R^{17}$, —C(=O)$NR^{17}R^{18}$, —$NR^{17}R^{18}$, —$NR^{17}$C(=O)$NHR^{18}$, —$NR^{17}$C(=O)($C_1$-$C_4$alkyl), —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;

$B^1$ and $B^2$ are independently N or $CR^B$, provided that $B_1$ and $B^2$ are not N at the same time;

each $R^B$ is independently hydrogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —$CO_2R^{17}$, —C(=O)$NR^{17}R^{18}$, —$NR^{17}R^{18}$, —$NR^{17}$C(=O)$NHR^{18}$, —$NR^{17}$C(=O)($C_1$-$C_4$alkyl), —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;

$R^1$ is hydrogen, unsubstituted or substituted $C_1$-$C_6$alkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^1$ is substituted then $R^1$ is substituted with 1-2 $R^{13}$ and 0-2 $R^{14}$;

$R^2$ is hydrogen, unsubstituted or substituted $C_1$-$C_6$alkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$ alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^2$ is substituted then $R^2$ is substituted with 1-2 $R^{15}$ and 0-2 $R^{16}$;

$R^3$ and $R^4$ are independently hydrogen, unsubstituted or substituted $C_1$-$C_6$ alkyl, unsubstituted or substituted $C_1$-$C_6$ fluoroalkyl, or unsubstituted or substituted $C_3$-$C_6$ cycloalkyl, wherein any substituted group of $R^3$ and $R^4$ is substituted with 1-4 $R^{12}$;

or $R^3$ and $R^4$ are taken together with the nitrogen atom with to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

$R^5$, $R^6$, $R^7$, $R^8$, $R^{10}$, and $R^{11}$ are each independently selected from the group consisting of hydrogen, unsubstituted or substituted $C_1$-$C_6$ alkyl, and unsubstituted or substituted $C_1$-$C_6$ fluoroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$ alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^5$, $R^6$, $R^7$, $R^8$, $R^{10}$, and $R^{11}$ is substituted then $R^5$, $R^6$, $R^7$, $R^8$, $R^{10}$, and $R^{11}$ is substituted with 1-2 $R^{15}$ and 0-2 $R^{16}$;

X is $NR^9$, O, or $CR^9R^{19}$;

$R^9$ is hydrogen, unsubstituted or substituted $C_1$-$C_6$ alkyl, or unsubstituted or substituted benzyl, wherein if $R^9$ is substituted then $R^9$ is substituted with 1-4 $R^{12}$;

$R^{19}$ is hydrogen, or unsubstituted or substituted $C_1$-$C_6$ alkyl, wherein if $R^{19}$ is substituted then $R^{19}$ is substituted with 1-4 $R^{12}$;

or $R^4$ and any one of $R^5$, $R^7$, $R^9$, or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^5$ and $R^6$ are taken together with the carbon atom with to which they are attached to form an unsubstituted or substituted monocyclic 4- to 7-membered carbocyclic ring, wherein if the carbocyclic ring is substituted then the carbocyclic ring is substituted with 1-4 $R^{12}$;

or $R^5$ and any one of $R^7$, $R^9$, or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^7$ and one of $R^9$ or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^9$ and $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

each $R^{12}$ is independently halogen, heterocycle, $C_1$-$C_4$alkyl, $C_1$-$C_4$fluoroalkyl, $C_1$-$C_4$fluoroalkoxy, —CN, —$OR^{17}$, —$CO_2R^{17}$, —C(=O)$NR^{17}R^{18}$, —$NR^{17}R^{18}$, —$NR^{17}$C(=O)$NHR^{18}$, —$NR^{17}$C(=O)$R^{18}$, —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;

each of $R^{13}$ and $R^{14}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}$C(=O)$R^{18}$, —$NR^{17}$C(=O)$NHR^{18}$, —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$, wherein if any group of $R^{13}$ and $R^{14}$ is substituted then the substituted group of $R^{13}$ and $R^{14}$ is substituted with 1-4$R^{12}$;

each of $R^{15}$ and $R^{16}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}$C(=O)$R^{18}$, —$NR^{17}$C(=O)$NHR^{18}$, —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$, wherein if any group of $R^{15}$ and $R^{16}$ is substituted then the substituted group of $R^{15}$ and $R^{16}$ is substituted with 1-4$R^{12}$;

each of $R^{17}$ and $R^{18}$ is independently hydrogen, $C_1$-$C_4$alkyl, $C_1$-$C_4$fluoroalkyl, $C_1$-$C_4$hydroxyalkyl, $C_1$-$C_4$aminoalkyl, or heterocycle;

m is 1, 2, 3, or 4; and n is 0, 1, 2, 3, or 4.

In another aspect, the compound of Formula (A) has the structure of Formula (I), or a pharmaceutically acceptable salt, pharmaceutically acceptable solvate, diastereomeric mixture, individual enantiomers or prodrug thereof:

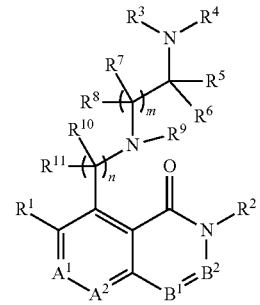

Formula (I)

wherein:

$A^1$ and $A^2$ are independently N or $CR^A$, provided that $A^1$ and $A^2$ are not N at the same time;

each $R^A$ is independently hydrogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —$CO_2R^{17}$, —C(=O)$NR^{17}R^{18}$, —$NR^{17}R^{18}$, —$NR^{17}$C(=O)$NHR^{18}$, —$NR^{17}$C(=O)($C_1$-$C_4$alkyl), —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;

$B_1$ and $B^2$ are independently N or $CR^B$, provided that $B_1$ and $B^2$ are not N at the same time;

each $R^B$ is independently hydrogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —$CO_2R^{17}$, —C(=O)$NR^{17}R^{18}$, —$NR^{17}R^{18}$, —$NR^{17}$C(=O)$NHR^{18}$, —$NR^{17}$C(=O)($C_1$-$C_4$alkyl), —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;

$R^1$ is hydrogen, unsubstituted or substituted $C_1$-$C_6$alkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^1$ is substituted then $R^1$ is substituted with 1-2 $R^{13}$ and 0-2 $R^{14}$;

$R^2$ is hydrogen, unsubstituted or substituted $C_1$-$C_6$alkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$ alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^2$ is substituted then $R^2$ is substituted with 1-2 $R^{15}$ and 0-2 $R^{16}$;

$R^3$ and $R^4$ are independently hydrogen, unsubstituted or substituted $C_1$-$C_6$ alkyl, unsubstituted or substituted $C_1$-$C_6$ fluoroalkyl, or unsubstituted or substituted $C_3$-$C_6$ cycloalkyl, wherein any substituted group of $R^3$ and $R^4$ is substituted with 1-4 $R^{12}$;

or $R^3$ and $R^4$ are taken together with the nitrogen atom with to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

$R^5$, $R^6$, $R^7$, $R^8$, $R^{10}$, and $R^{11}$ are each independently selected from the group consisting of hydrogen, unsubstituted or substituted $C_1$-$C_6$ alkyl, and unsubstituted or substituted $C_1$-$C_6$ fluoroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$ alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^5$, $R^6$, $R^7$, $R^8$, $R^{10}$, and $R^{11}$ is substituted then $R^5$, $R^6$, $R^7$, $R^8$, $R^{10}$, and $R^{11}$ is substituted with 1-2 $R^{15}$ and 0-2 $R^{16}$;

$R^9$ is hydrogen, unsubstituted or substituted $C_1$-$C_6$ alkyl, or unsubstituted or substituted benzyl, wherein if $R^9$ is substituted then $R^9$ is substituted with 1-4 $R^{12}$;

or $R^4$ and any one of $R^5$, $R^7$, $R^9$, or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^5$ and $R^6$ are taken together with the carbon atom with to which they are attached to form an unsubstituted or substituted monocyclic 4- to 7-membered carbocyclic ring, wherein if the carbocyclic ring is substituted then the carbocyclic ring is substituted with 1-4 $R^{12}$;

or $R^5$ and any one of $R^7$, $R^9$, or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^7$ and one of $R^9$ or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^9$ and $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

each $R^{12}$ is independently halogen, heterocycle, $C_1$-$C_4$alkyl, $C_1$-$C_4$fluoroalkyl, $C_1$-$C_4$fluoroalkoxy, —CN, —$OR^{17}$, —$CO_2R^{17}$, —C(=O)$NR^{17}R^{18}$, —$NR^{17}R^{18}$, —$NR^{17}$C(=O)$NHR^{18}$, —$NR^{17}$C(=O)$R^{18}$, —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;

each of $R^{13}$ and $R^{14}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}$C(=O)$R^{18}$, —$NR^{17}$C(=O)$NHR^{18}$, —C(=$NOR^{17}$)$R^{18}$, —S(=O)($C_1$-$C_4$alkyl), —$SO_2$($C_1$-$C_4$alkyl), or —$SO_2NR^{17}R^{18}$, wherein if any group of $R^{13}$ and $R^{14}$ is substituted then the substituted group of $R^{13}$ and $R^{14}$ is substituted with 1-4$R^{12}$;

each of $R^{15}$ and $R^{16}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}$C(=O)$R^{18}$, —$NR^{17}$C(=O)$NHR^{18}$, —C(=$NOR^{17}$)$R^{18}$, —S(=O)($C_1$-$C_4$alkyl), —$SO_2$($C_1$-$C_4$alkyl), or —$SO_2NR^{17}R^{18}$, wherein if any group of $R^{15}$ and $R^{16}$ is substituted then the substituted group of $R^{15}$ and $R^{16}$ is substituted with 1-4$R^{12}$;

each of $R^{17}$ and $R^{18}$ is independently hydrogen, $C_1$-$C_4$alkyl, $C_1$-$C_4$fluoroalkyl, $C_1$-$C_4$hydroxyalkyl, $C_1$-$C_4$aminoalkyl, or heterocycle;

m is 1, 2, 3, or 4; and n is 0, 1, 2, 3, or 4.

Also described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

Also described herein is a method of treating a disease or condition in a mammal that would benefit from the modulation of somatostatin receptor activity comprising administering a small molecule compound as described herein, or pharmaceutically acceptable salt, or solvate thereof, to the mammal in need thereof. In some embodiments, the small molecule compound is orally administered. In some embodiments, the disease or condition is acromegaly, a neuroendocrine tumor, an ophthalmic disease or condition, neuropathy, nephropathy, a respiratory disease or condition, cancer, pain, a neurodegenerative disease or condition, an inflammatory disease or condition, a psychiatric disease or condition, or combinations thereof.

In any of the aforementioned aspects are further embodiments in which the effective amount of the compound of Formula (A), or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the embodiments disclosed herein, the mammal is a human.

In some embodiments, compounds provided herein are orally administered to a human.

Articles of manufacture, which include packaging material, a compound of Formula (A), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for modulating one or more subtype somatostatin receptor proteins, or for the treatment, prevention or amelioration of one or more symptoms of a disease or condition that would benefit from modulating one or more subtype somatostatin receptor proteins, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Somatostatin (SST), also known as somatotropin release inhibiting factor (SRIF) was initially isolated as a 14-amino acid peptide from ovine hypothalamii (Brazeau et al., *Science* 179, 77-79, 1973). An N-terminal extended 28-amino acid peptide with similar biological activity to 14-amino acid somatostatin was subsequently isolated (Pradayrol et, al., *FEBS Letters*, 109, 55-58, 1980; Esch et al., *Proc. Natl. Acad. Sci. USA*, 77, 6827-6831, 1980). SST is a regulatory peptide produced by several cell types in response to other neuropeptides, neurotransmitters, hormones, cytokines, and growth factors. SST acts through both endocrine, paracrine, and nerve pathways to affect its target cells. Many of these effects are related to the inhibition of secretion of other hormones, most notably growth hormone (GH). They are produced by a wide variety of cell types in the central nervous system (CNS) and gut and have multiple functions including modulation of secretion of growth hormone (GH), insulin, glucagon, as well as many other hormones that are anti-proliferative.

These pleotropic actions of somatostatins are mediated by six somatostatin receptor proteins (SSTR1, SSTR2a, SSTR2b, SSTR3, SSTR4, SSTR5). The six somatostatin receptor proteins are encoded by five different somatostatin receptor genes (Reisine and Bell, *Endocr Rev.* 16, 427-442, 1995; Patel and Srikant, *Trends Endocrinol Metab* 8, 398-405, 1997). All the receptors are members of the class-A subgroup of the GPCR superfamily. SST2A receptor is the most widely expressed subtype in human tumors and is the dominant receptor by which GH secretion is suppressed.

It is possible to selectively modulate any one of the somatostatin receptor subtypes, or combination thereof. In some embodiments, selectively modulating any one of the somatostatin receptor subtypes relative to the other somatostatin receptor subtypes, or combination thereof, in useful in a variety of clinical applications.

For example, modulation of SSTR2 activity mediates the inhibition of growth hormone (GH) release from the anterior pituitary and glucagon release from pancreas. SSTR2 is also implicated in many other biological functions such as, but not limited to, cell proliferation, nociception, inflammation, and angiogenesis. In some embodiments, a selective SSTR2 modulator is used in the treatment of acromegaly, gut neuroendocrine tumors, pain, neuropathies, nephropathies, and inflammation, as well as retinopathies resulting from aberrant blood vessel growth. In some other embodiments, a selective SSTR2 modulator is used in the treatment of arthritis, pain, cancer, inflammatory bowel disease, irritable bowel syndrome, Crohn's disease, Cushing's disease, acute lung injury, acute respiratory distress syndrome, and ophthalmic disorders such as age-related macular degeneration (AMD), diabetic retinopathy, diabetic macular edema, and Graves ophthalmology, among others.

In some embodiments, SSTR4 agonists exhibit anti-inflammatory and anti-nociceptive effects.

In some embodiments, SSTR3 agonists inhibit insulin secretion.

In some embodiments, SSTR5 agonists inhibit insulin secretion. In addition, SSTR5 has also been implicated to modulate the release of growth hormone.

Somatostatin peptide and its receptor subtypes are also widely expressed in the brain and disruption or diminishment of their activity is potentially involved in several psychiatric and neurodegenerative diseases. For example, concentrations of somatostatin in the cebrebral cortex and hippocampus are reduced in schizophrenics and one of the most consistent neuropathologic findings in this patient group is a deficit in cortical inhibitory interneurons expressing somatostatin. Somatostatin is also highly expressed in brain regions associated with seizures and has also been implicated as having an important role in epilepsy. Somatostatin levels are diminished in the hippocampi of Alzheimer's and Parkinson's patients, suggesting that restoration of its signaling as a potential drug target for neurodegeneration.

In one aspect, compounds described herein are modulators of any one of somatostatin receptors, or combinations thereof. In some embodiments, compounds described herein modulate the activity of any one of SSTR1, SSTR2, SSTR3, SSTR4, SSTR5, or combinations thereof.

In some embodiments, compounds described herein selectively modulate the activity of any two of somatostatin receptors relative to the other somatostatin receptors. In some embodiments, compounds described herein selectively modulate the activity of SSTR2 and SSTR4 relative to the other somatostatin receptors. In some embodiments, compounds described herein selectively modulate the activity of SSTR2 and SSTR5 relative to the other somatostatin receptors. In some embodiments, compounds described herein selectively modulate the activity of SSTR1 and SSTR3 relative to the other somatostatin receptors. In some embodiments, compounds described herein selectively modulate the activity of SSTR1 and SSTR2 relative to the other somatostatin receptors. In some embodiments, compounds described herein selectively modulate the activity of SSTR3 and SSTR4 relative to the other somatostatin receptors. In some embodiments, compounds described herein selectively modulate the activity of SSTR3 and SSTR5 relative to the other somatostatin receptors.

In some embodiments, compounds described herein selectively modulate the activity of any three of somatostatin receptors relative to the other somatostatin receptors. In some embodiments, compounds described herein selectively modulate the activity of SSTR2, SSTR3 and SSTR4 relative to the other somatostatin receptors.

In some embodiments, compounds described here are amenable to oral administration to a mammal in need of treatment with a somatostatin modulator.

In some embodiments, somatostatin receptor modulators described herein have utility over a wide range of therapeutic applications. In some embodiments, somatostatin receptor modulators described herein are used in the treatment of a variety of diseases or conditions such as, but not limited to acromegaly, neuroendocrine tumors, retinopathies and other ophthalmic disorders, neuropathy, nephropathy, respiratory diseases, cancers, pain, neurodegenerative diseases, inflammatory diseases, as well as psychiatric and neurodegenerative disorders. In some embodiments, somatostatin receptor modulators described herein are used in the treatment of acromegaly in a mammal.

Compounds

Compounds of Formula (A), including pharmaceutically acceptable salts, prodrugs, active metabolites and pharmaceutically acceptable solvates thereof, are somatostatin receptor modulators. In some embodiments, the somatostatin receptor modulators are somatostatin receptor agonists.

In one aspect, provided herein is a compound of Formula (A), or a pharmaceutically acceptable salt, pharmaceutically acceptable solvate, diastereomeric mixture, individual enantiomers or prodrug thereof:

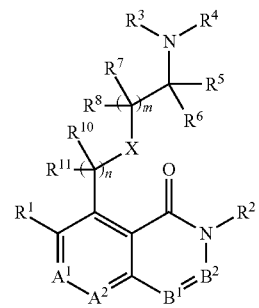

Formula (A)

wherein:
$A^1$ and $A^2$ are independently N or $CR^A$, provided that $A^1$ and $A^2$ are not N at the same time;
each $R^A$ is independently hydrogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —$CO_2R^{17}$, —C(=O)$NR^{17}R^{18}$, —$NR^{17}R^{18}$, —$NR^{17}$C(=O)$NHR^{18}$, —$NR^{17}$C(=O)($C_1$-$C_4$alkyl), —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;
$B_1$ and $B^2$ are independently N or $CR^B$, provided that $B_1$ and $B^2$ are not N at the same time;
each $R^B$ is independently hydrogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —$CO_2R^{17}$, —C(=O)$NR^{17}R^{18}$, —$NR^{17}R^{18}$, —$NR^{17}$C(=O)$NHR^{18}$, —$NR^{17}$C(=O)($C_1$-$C_4$alkyl), —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;
$R^1$ is hydrogen, unsubstituted or substituted $C_1$-$C_6$alkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^1$ is substituted then $R^1$ is substituted with 1-2 $R^{13}$ and 0-2 $R^{14}$;
$R^2$ is hydrogen, unsubstituted or substituted $C_1$-$C_6$alkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$ alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^2$ is substituted then $R^2$ is substituted with 1-2 $R^{15}$ and 0-2 $R^{16}$;
$R^3$ and $R^4$ are independently hydrogen, unsubstituted or substituted $C_1$-$C_6$ alkyl, unsubstituted or substituted $C_1$-$C_6$ fluoroalkyl, or unsubstituted or substituted $C_3$-$C_6$ cycloalkyl, wherein any substituted group of $R^3$ and $R^4$ is substituted with 1-4 $R^{12}$;
or $R^3$ and $R^4$ are taken together with the nitrogen atom with to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

$R^5$, $R^6$, $R^7$, $R^8$, $R^{10}$, and $R^{11}$ are each independently selected from the group consisting of hydrogen, unsubstituted or substituted $C_1$-$C_6$ alkyl, and unsubstituted or substituted $C_1$-$C_6$ fluoroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$ alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^5$, $R^6$, $R^7$, $R^8$, $R^{10}$, and $R^{11}$ is substituted then $R^5$, $R^6$, $R^7$, $R^8$, $R^{10}$, and $R^{11}$ is substituted with 1-2 $R^{15}$ and 0-2 $R^{16}$;

X is $NR^9$, O, or $CR^9R^{19}$;

$R^9$ is hydrogen, unsubstituted or substituted $C_1$-$C_6$ alkyl, or unsubstituted or substituted benzyl, wherein if $R^9$ is substituted then $R^9$ is substituted with 1-4 $R^{12}$;

$R^{19}$ is hydrogen, or unsubstituted or substituted $C_1$-$C_6$ alkyl, wherein if $R^{19}$ is substituted then $R^{19}$ is substituted with 1-4 $R^{12}$;

or $R^4$ and any one of $R^5$, $R^7$, $R^9$, or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^5$ and $R^6$ are taken together with the carbon atom with to which they are attached to form an unsubstituted or substituted monocyclic 4- to 7-membered carbocyclic ring, wherein if the carbocyclic ring is substituted then the carbocyclic ring is substituted with 1-4 $R^{12}$;

or $R^5$ and any one of $R^7$, $R^9$, or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^7$ and one of $R^9$ or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^9$ and $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

each $R^{12}$ is independently halogen, heterocycle, $C_1$-$C_4$alkyl, $C_1$-$C_4$alkoxy, $C_1$-$C_4$hydroxyalkyl, $C_1$-$C_4$aminoalkyl, $C_1$-$C_4$fluoroalkyl, $C_1$-$C_4$fluoroalkoxy, —CN, —$OR^{17}$, —$CO_2R^{17}$, —$C_1$-$C_4$alkyl$CO_2R^{17}$, —C(=O)$NR^{17}R^{18}$, —$NR^{17}R^{18}$, —$NR^{17}C(=O)NHR^{18}$, —$NR^{17}C(=O)R^{18}$, —C(=$NOR^{17}$)$R^{18}$, —$SR^{17}$, —S(=O)($C_1$-$C_4$alkyl), —$SO_2(C_1$-$C_4$alkyl), or —$SO_2NR^{17}R^{18}$;

each of $R^{13}$ and $R^{14}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}C(=O)R^{18}$, —$NR^{17}C(=O)$$NHR^{18}$, —C(=$NOR^{17}$)$R^{18}$, —$SR^{17}$, —S(=O)($C_1$-$C_4$alkyl), —$SO_2(C_1$-$C_4$alkyl), or —$SO_2NR^{17}R^{18}$, wherein if any group of $R^{13}$ and $R^{14}$ is substituted then the substituted group of $R^{13}$ and $R^{14}$ is substituted with 1-4$R^{12}$;

each of $R^{15}$ and $R^{16}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}C(=O)R^{18}$, —$NR^{17}C(=O)$$NHR^{18}$, —C(=$NOR^{17}$)$R^{18}$, —S(=O)($C_1$-$C_4$alkyl), —$SO_2(C_1$-$C_4$alkyl), or —$SO_2NR^{17}R^{18}$, wherein if any group of $R^{15}$ and $R^{16}$ is substituted then the substituted group of $R^{15}$ and $R^{16}$ is substituted with 1-4$R^{12}$;

each of $R^{17}$ and $R^{18}$ is independently hydrogen, $C_1$-$C_4$alkyl, $C_1$-$C_4$fluoroalkyl, $C_1$-$C_4$hydroxyalkyl, $C_1$-$C_4$aminoalkyl, or heterocycle;

m is 1, 2, 3, or 4; and n is 0, 1, 2, 3, or 4.

In some embodiments, X is $NR^9$. In some embodiments, X is O. In some embodiments, X is $CR^9R^{19}$.

In one aspect, the compound of Formula (A) has the structure of Formula (I), or a pharmaceutically acceptable salt, pharmaceutically acceptable solvate, diastereomeric mixture, individual enantiomers or prodrug thereof:

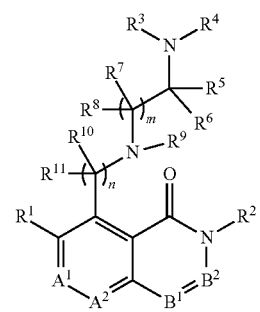

Formula (I)

wherein:

$A^1$ and $A^2$ are independently N or $CR^A$, provided that $A^1$ and $A^2$ are not N at the same time;

each $R^A$ is independently hydrogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —$CO_2R^{17}$, —C(=O)$NR^{17}R^{18}$, —$NR^{17}R^{18}$, —$NR^{17}C(=O)$$NHR^{18}$, —$NR^{17}C(=O)(C_1$-$C_4$alkyl), —C(=$NOR^{17}$)$R^{18}$, —$SR^{17}$, —S(=O)($C_1$-$C_4$alkyl), —$SO_2(C_1$-$C_4$alkyl), or —$SO_2NR^{17}R^{18}$;

$B^1$ and $B^2$ are independently N or $CR^B$, provided that $B^1$ and $B^2$ are not N at the same time;

each $R^B$ is independently hydrogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —$CO_2R^{17}$, —C(=O)$NR^{17}R^{18}$, —$NR^{17}R^{18}$, —$NR^{17}$C(=O)$NHR^{18}$, —$NR^{17}$C(=O)($C_1$-$C_4$alkyl), —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;

$R^1$ is hydrogen, unsubstituted or substituted $C_1$-$C_6$alkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^1$ is substituted then $R^1$ is substituted with 1-2 $R^{13}$ and 0-2 $R^{14}$;

$R^2$ is hydrogen, unsubstituted or substituted $C_1$-$C_6$alkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$ alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^2$ is substituted then $R^2$ is substituted with 1-2 $R^{15}$ and 0-2 $R^{16}$;

$R^3$ and $R^4$ are independently hydrogen, unsubstituted or substituted $C_1$-$C_6$ alkyl, unsubstituted or substituted $C_1$-$C_6$ fluoroalkyl, or unsubstituted or substituted $C_3$-$C_6$ cycloalkyl, wherein any substituted group of $R^3$ and $R^4$ is substituted with 1-4 $R^{12}$;

or $R^3$ and $R^4$ are taken together with the nitrogen atom with to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

$R^5$, $R^6$, $R^7$, $R^8$, $R^{10}$, and $R^{11}$ are each independently selected from the group consisting of hydrogen, unsubstituted or substituted $C_1$-$C_6$ alkyl, and unsubstituted or substituted $C_1$-$C_6$ fluoroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$ alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^5$, $R^6$, $R^7$, $R^8$, $R^{10}$, and $R^{11}$ is substituted then $R^5$, $R^6$, $R^7$, $R^8$, $R^{10}$, and $R^{11}$ is substituted with 1-2 $R^{15}$ and 0-2 $R^{16}$;

$R^9$ is hydrogen, unsubstituted or substituted $C_1$-$C_6$ alkyl, or unsubstituted or substituted benzyl, wherein if $R^9$ is substituted then $R^9$ is substituted with 1-4 $R^{12}$;

or $R^4$ and any one of $R^5$, $R^7$, $R^9$, or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^5$ and $R^6$ are taken together with the carbon atom with to which they are attached to form an unsubstituted or substituted monocyclic 4- to 7-membered carbocyclic ring, wherein if the carbocyclic ring is substituted then the carbocyclic ring is substituted with 1-4 $R^{12}$;

or $R^5$ and any one of $R^7$, $R^9$, or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^7$ and one of $R^9$ or $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

or $R^9$ and $R^{11}$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;

each $R^{12}$ is independently halogen, heterocycle, $C_1$-$C_4$alkyl, $C_1$-$C_4$alkoxy, $C_4$hydroxyalkyl, $C_1$-$C_4$aminoalkyl, $C_1$-$C_4$fluoroalkyl, $C_1$-$C_4$fluoroalkoxy, —CN, —$OR^{17}$, —$CO_2R^{17}$, —$C_1$-$C_4$alkyl$CO_2R^{17}$, —C(=O)$NR^{17}R^{18}$, —$NR^{17}R^{18}$, —$NR^{17}$C(=O)$NHR^{18}$, —$NR^{17}$C(=O)$R^{18}$, —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;

each of $R^{13}$ and $R^{14}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}$C(=O)$R^{18}$, —$NR^{17}$C(=O)$NHR^{18}$, —C(=$NOR^{17}$)$R^{18}$, —S(=O)($C_1$-$C_4$alkyl), —$SO_2$($C_1$-$C_4$alkyl), or —$SO_2NR^{17}R^{18}$, wherein if any group of $R^{13}$ and $R^{14}$ is substituted then the substituted group of $R^{13}$ and $R^{14}$ is substituted with 1-4$R^{12}$;

each of $R^{15}$ and $R^{16}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}$C(=O)$R^{18}$, —$NR^{17}$C(=O)$NHR^{18}$, —C(=$NOR^{17}$)$R^{18}$, —S(=O)($C_1$-$C_4$alkyl), —$SO_2$($C_1$-$C_4$alkyl), or —$SO_2NR^{17}R^{18}$, wherein if any group of $R^{15}$ and $R^{16}$ is substituted then the substituted group of $R^{15}$ and $R^{16}$ is substituted with 1-4$R^{12}$;

each of $R^{17}$ and $R^{18}$ is independently hydrogen, $C_1$-$C_4$alkyl, $C_1$-$C_4$fluoroalkyl, $C_1$-$C_4$hydroxyalkyl, $C_1$-$C_4$aminoalkyl, or heterocycle;

m is 1, 2, 3, or 4; and n is 0, 1, 2, 3, or 4.

For any and all of the embodiments, substituents are selected from among a subset of the listed alternatives. For example, in some embodiments, m is 1, 2, 3, or 4. In other embodiments, m is 1, 2, or 3. In some other embodiments, m is 1 or 2. In yet other embodiments, m is 1.

In some embodiments, n is 0, 1, 2, 3, or 4. In some embodiments, n is 0, 1, 2, or 3. In some embodiments, n is 0, 1, or 2. In some embodiments, n is 0 or 1. In some embodiments, n is 1, 2, 3, or 4. In some embodiments, n is 1, 2, or 3. In some embodiments, n is 1 or 2. In some embodiments, n is 1.

In some embodiments, $A^1$ and $A^2$ are independently N or $CR^A$, provided that $A^1$ and $A^2$ are not N at the same time or $A^1$ and $A^2$ are not $CR^A$ at the same time.

In some embodiments, $B_1$ and $B^2$ are independently N or $CR^B$, provided that $B^1$ and $B^2$ are not N at the same time or $B^1$ and $B^2$ are not $CR^B$ at the same time.

In some embodiments, $A^1$ is $CR^A$; and $A^2$ is N. In some embodiments, $A^1$ is N; and $A^2$ is $CR^A$. In some embodiments, $A^1$ is $CR^A$; and $A^2$ is $CR^A$. In some embodiments, each $R^A$ is independently hydrogen, $C_1$-$C_4$alkyl, $C_1$-$C_4$fluoroalkyl, or —CN.

In some embodiments, $B^1$ is N; and $B^2$ is $CR^B$. In some embodiments, $B^1$ is $CR^B$; and $B^2$ is N. In some embodiments, B is $CR^B$; and $B^2$ is $CR^B$. In some embodiments, each $R^B$ is independently hydrogen, $C_1$-$C_4$alkyl, $C_1$-$C_4$fluoroalkyl, or —CN.

In some embodiments, $A^1$ is $CR^A$; $A^2$ is N; $B^1$ is N; and $B^2$ is $CR^B$.

In some embodiments, m is 1 or 2; and is 1 or 2. In some embodiments, m is 1; and n is 1.

In some embodiments, the compound of Formula (I) has the structure of Formula (Ia), or a pharmaceutically acceptable salt or solvate thereof:

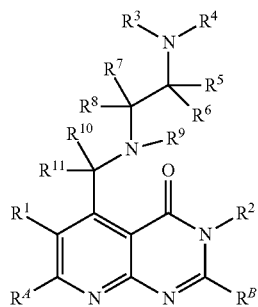

Formula (Ia)

In some embodiments, the compound of Formula (I) has the structure of Formula (Ib), or a pharmaceutically acceptable salt or solvate thereof:

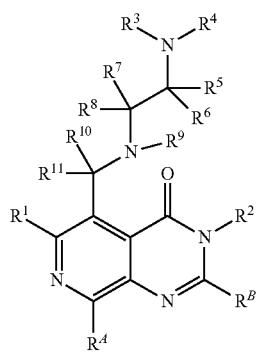

Formula (Ib)

In some embodiments, the compound of Formula (I) has the structure of Formula (Ic), or a pharmaceutically acceptable salt or solvate thereof:

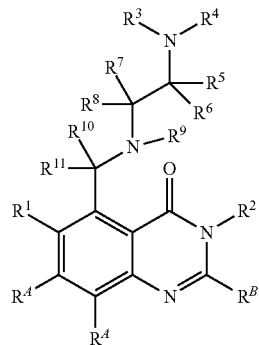

Formula (Ic)

In some embodiments, the compound of Formula (I) has the structure of Formula (Id), or a pharmaceutically acceptable salt or solvate thereof:

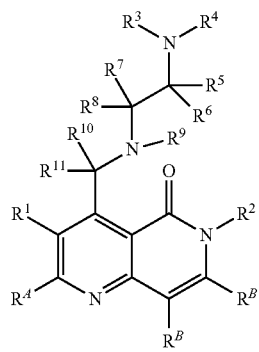

Formula (Id)

In some embodiments, the compound of Formula (I) has the structure of Formula (Ie), or a pharmaceutically acceptable salt or solvate thereof:

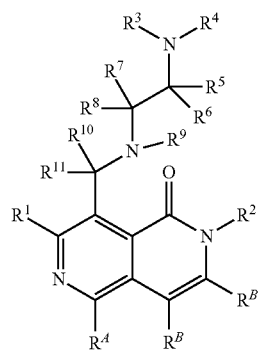

Formula (Ie)

In some embodiments, the compound of Formula (I) has the structure of Formula (If), or a pharmaceutically acceptable salt or solvate thereof:

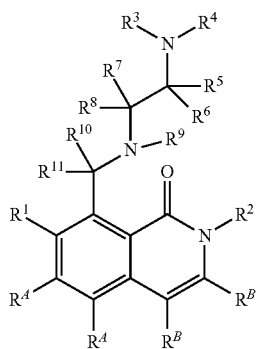

Formula (If)

In some embodiments, the compound of Formula (I) has the structure of Formula (Ig), or a pharmaceutically acceptable salt or solvate thereof:

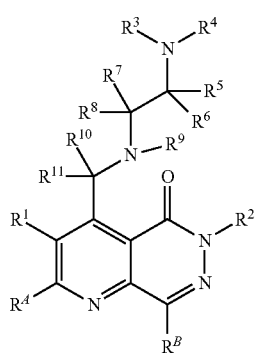

Formula (Ig)

In some embodiments, the compound of Formula (I) has the structure of Formula (Ih), or a pharmaceutically acceptable salt or solvate thereof:

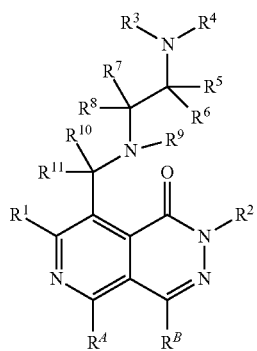

Formula (Ih)

In some embodiments, the compound of Formula (I) has the structure of Formula (Ii), or a pharmaceutically acceptable salt or solvate thereof:

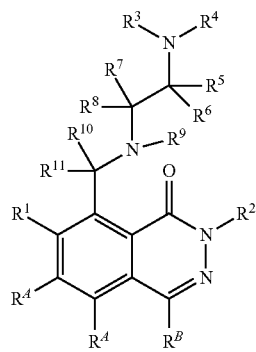

Formula (Ii)

In some embodiments, each $R^A$ is independently hydrogen, methyl, ethyl, n-propyl, propyl, n-butyl, i-butyl, sec-butyl, or tert-butyl; and each $R^B$ is independently hydrogen, methyl, ethyl, n-propyl, i-propyl, n-butyl, i-butyl, sec-butyl, or tert-butyl.

In some embodiments, $R^1$ is an unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^1$ is substituted then $R^1$ is substituted with 1-2 $R^{13}$ and 0-2 $R^{14}$.

In some embodiments, $R^1$ is an unsubstituted or substituted monocyclic carbocycle, or unsubstituted or substituted bicyclic carbocycle, wherein if $R^1$ is substituted then $R^1$ is substituted with 1-2 $R^{13}$ and 0-2 $R^{14}$.

In some embodiments, $R^1$ is an unsubstituted or substituted monocyclic carbocycle selected from unsubstituted or substituted phenyl, unsubstituted or substituted cyclopropyl, unsubstituted or substituted cyclobutyl, unsubstituted or substituted cyclopentyl, or unsubstituted or substituted cyclohexyl, wherein if $R^1$ is substituted then $R^1$ is substituted with 1-2 $R^{13}$ and 0-2 $R^{14}$.

In some embodiments, $R^1$ is an unsubstituted or substituted phenyl, wherein if $R^1$ is substituted then $R^1$ is substituted with 1-2 $R^{13}$ and 0-2 $R^{14}$.

In some embodiments, $R^1$ is

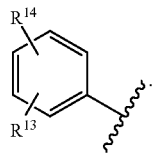

In some embodiments, $R^1$ is

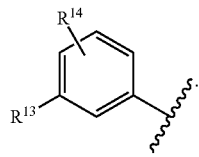

In some embodiments, $R^1$ is

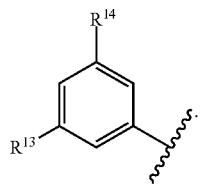

In some embodiments, $R^{13}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}$C(=O)$R^{18}$, —$NR^{17}$C(=O)$NHR^{18}$, —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$, wherein if any group of $R^{13}$ is substituted then the substituted group of $R^{13}$ is substituted with 1-4 $R^{12}$.

In some embodiments, $R^{13}$ is hydrogen, halogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, or —CN, wherein if any group of $R^{13}$ is substituted then the substituted group of $R^{13}$ is substituted with $R^{12}$; and $R^{14}$ is hydrogen, halogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}$C(=O)$NHR^{18}$, —$NR^{17}$C(=O)$R^{18}$, —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$; wherein if any group of $R^{14}$ is substituted then the substituted group of $R^{14}$ is substituted with $R^{12}$.

In some embodiments, $R^{13}$ is hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, —CN, or OH; wherein if any group of $R^{13}$ is substituted then the substituted group of $R^{13}$ is substituted with $R^{12}$; and $R^{14}$ is hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, —CN, —OH; wherein if any group of $R^{14}$ is substituted then the substituted group of $R^{14}$ is substituted with $R^{12}$.

In some embodiments, $R^1$ is an unsubstituted or substituted bicyclic carbocycle selected from unsubstituted or substituted naphthyl, unsubstituted or substituted indanyl, unsubstituted or substituted indenyl, or unsubstituted or substituted tetrahydronaphthyl, wherein if $R^1$ is substituted then $R^1$ is substituted with 1-2 $R^{13}$ and 0-2 $R^{14}$.

In some embodiments, $R^1$ is an unsubstituted or substituted monocyclic heterocycle containing 1-4 N atoms and 0 or 1 O or S atom, unsubstituted or substituted monocyclic heterocycle containing 0-4 N atoms and 1 O or S atoms, unsubstituted or substituted bicyclic heterocycle containing 1-4 N atoms and 0 or 1 O or S atoms, or unsubstituted or substituted bicyclic heterocycle containing 0-4 N atoms and 1 O or S atoms, wherein if $R^1$ is substituted then $R^1$ is substituted with 1-2 $R^{13}$ and 0-2 $R^{14}$.

In some embodiments, $R^1$ is an unsubstituted or substituted monocyclic heterocycle selected from unsubstituted or substituted furanyl, unsubstituted or substituted pyrrolyl, unsubstituted or substituted oxazolyl, unsubstituted or substituted thiazolyl, unsubstituted or substituted imidazolyl, unsubstituted or substituted pyrazolyl, unsubstituted or substituted triazolyl, unsubstituted or substituted tetrazolyl, unsubstituted or substituted isoxazolyl, unsubstituted or substituted isothiazolyl, unsubstituted or substituted oxadiazolyl, unsubstituted or substituted thiadiazolyl, unsubstituted or substituted pyridinyl, unsubstituted or substituted pyrimidinyl, unsubstituted or substituted pyrazinyl, unsubstituted or substituted pyridazinyl, and unsubstituted or substituted triazinyl, wherein if $R^1$ is substituted then $R^1$ is substituted with 1-2 $R^{13}$ and 0-2 $R^{14}$.

In some embodiments, $R^1$ is an unsubstituted or substituted bicyclic heterocycle selected from unsubstituted or substituted quinolinyl, unsubstituted or substituted isoquinolinyl, unsubstituted or substituted quinazolinyl, unsubstituted or substituted quinoxalinyl, unsubstituted or substituted naphthyridinyl, unsubstituted or substituted indolyl, unsubstituted or substituted indazolyl, unsubstituted or substituted benzoxazolyl, unsubstituted or substituted benzisoxazolyl, unsubstituted or substituted benzofuranyl, unsubstituted or substituted benzothienyl, unsubstituted or substituted benzothiazolyl, unsubstituted or substituted benzimidazolyl, unsubstituted or substituted purinyl, unsubstituted or substituted cinnolinyl, unsubstituted or substituted phthalazinyl, unsubstituted or substituted pteridinyl, unsubstituted or substituted pyridopyrimidinyl, unsubstituted or substituted pyrazolopyrimidinyl, or unsubstituted or substituted azaindolyl, wherein if $R^1$ is substituted then $R^1$ is substituted with 1-2 $R^{13}$ and 0-2 $R^{14}$.

In some embodiments, $R^2$ is an unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if $R^2$ is substituted then $R^2$ is substituted with 1-2 $R^{15}$ and 0-2 $R^{16}$.

In some embodiments, $R^2$ is an unsubstituted or substituted monocyclic carbocycle, or unsubstituted or substituted bicyclic carbocycle, wherein if $R^2$ is substituted then $R^2$ is substituted with 1-2 $R^{15}$ and 0-2 $R^{16}$.

In some embodiments, $R^2$ is an unsubstituted or substituted monocyclic carbocycle selected from unsubstituted or substituted phenyl, unsubstituted or substituted cyclopropyl, unsubstituted or substituted cyclobutyl, unsubstituted or substituted cyclopentyl, or unsubstituted or substituted cyclohexyl, wherein if $R^2$ is substituted then $R^2$ is substituted with 1-2 $R^{15}$ and 0-2 $R^{16}$.

In some embodiments, $R^2$ is an unsubstituted or substituted phenyl, wherein if $R^2$ is substituted then $R^2$ is substituted with 1-2 $R^{15}$ and 0-2 $R^{16}$.

In some embodiments, $R^2$ is

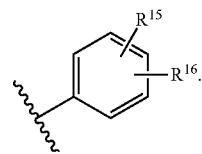

In some embodiments, $R^2$ is

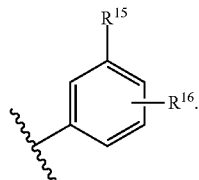

In some embodiments, $R^2$ is

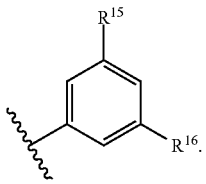

In some embodiments, $R^{15}$ is hydrogen, halogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, unsubstituted or substituted heterocycle, —CN, —OH, —CO$_2$R$^{17}$, —C(=O)NR$^{17}$R$^{18}$, —NR$^{17}$R$^{18}$, —NR$^{17}$C(=O)R$^{18}$, —NR$^{17}$C(=O)NHR$^{18}$, —C(=NOR$^{17}$)R$^{18}$, —SR$^{17}$, —S(=O)(C$_1$-C$_4$alkyl), —SO$_2$(C$_1$-C$_4$alkyl), or —SO$_2$NR$^{17}$R$^{18}$, wherein if any group of $R^{15}$ is substituted then the substituted group of $R^{15}$ is substituted with $R^{12}$; $R^{16}$ is hydrogen, halogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, or —OH, wherein if any group of $R^{16}$ is substituted then the substituted group of $R^{16}$ is substituted with $R^{12}$.

In some embodiments, each $R^{15}$ is independently F, Cl, —CF$_3$, —CN, —OH, —CO$_2$R$^{14}$, or —C(=O)NR$^{14}$R$^{15}$; and each $R^{16}$ is independently hydrogen, halogen, unsubstituted or substituted $C_1$-$C_4$alkyl, unsubstituted or substituted $C_1$-$C_4$alkoxy, —CN, —OH, —CO$_2$R$^{14}$, —C(=O)NR$^{14}$R$^{15}$, —SR$^{14}$, —S(=O)(C$_1$-C$_4$alkyl), —SO$_2$(C$_1$-C$_4$alkyl), or —SO$_2$NR$^{14}$R$^{15}$; wherein if any group of $R^{16}$ is substituted then the substituted group of $R^{16}$ is substituted with $R^{12}$.

In some embodiments, $R^2$ is an unsubstituted or substituted bicyclic carbocycle selected from unsubstituted or substituted naphthyl, unsubstituted or substituted indanyl, unsubstituted or substituted indenyl, or unsubstituted or substituted tetrahyodronaphthyl, wherein if $R^2$ is substituted then $R^2$ is substituted with 1-2 $R^{15}$ and 0-2 $R^{16}$.

In some embodiments, $R^2$ is an unsubstituted or substituted monocyclic heterocycle containing 1-4 N atoms and 0 or 1 O or S atom, unsubstituted or substituted monocyclic heterocycle containing 0-4 N atoms and 1 O or S atoms, unsubstituted or substituted bicyclic heterocycle containing 1-4 N atoms and 0 or 1 O or S atoms, or unsubstituted or substituted bicyclic heterocycle containing 0-4 N atoms and 1 O or S atoms, wherein if $R^2$ is substituted then $R^2$ is substituted with 1-2 $R^{15}$ and 0-2 $R^{16}$.

In some embodiments, $R^2$ is an unsubstituted or substituted monocyclic heterocycle selected from unsubstituted or substituted furanyl, unsubstituted or substituted pyrrolyl, unsubstituted or substituted oxazolyl, unsubstituted or substituted thiazolyl, unsubstituted or substituted imidazolyl, unsubstituted or substituted pyrazolyl, unsubstituted or substituted triazolyl, unsubstituted or substituted tetrazolyl, unsubstituted or substituted isoxazolyl, unsubstituted or substituted isothiazolyl, unsubstituted or substituted oxadiazolyl, unsubstituted or substituted thiadiazolyl, unsubstituted or substituted pyridinyl, unsubstituted or substituted pyrimidinyl, unsubstituted or substituted pyrazinyl, unsubstituted or substituted pyridazinyl, and unsubstituted or substituted triazinyl, wherein if $R^2$ is substituted then $R^2$ is substituted with 1-2 $R^{15}$ and 0-2 $R^{16}$.

In some embodiments, $R^2$ is an unsubstituted or substituted bicyclic heterocycle selected from unsubstituted or substituted quinolinyl, unsubstituted or substituted isoquinolinyl, unsubstituted or substituted quinazolinyl, unsubstituted or substituted quinoxalinyl, unsubstituted or substituted naphthyridinyl, unsubstituted or substituted indolyl, unsubstituted or substituted indazolyl, unsubstituted or substituted benzoxazolyl, unsubstituted or substituted benzisoxazolyl, unsubstituted or substituted benzofuranyl, unsubstituted or substituted benzothienyl, unsubstituted or substituted benzothiazolyl, unsubstituted or substituted benzimidazolyl, unsubstituted or substituted purinyl, unsubstituted or substituted cinnolinyl, unsubstituted or substituted phthalazinyl, unsubstituted or substituted pteridinyl, unsubstituted or substituted pyridopyrimidinyl, unsubstituted or substituted pyrazolopyrimidinyl, or unsubstituted or substituted azaindolyl, wherein if $R^2$ is substituted then $R^2$ is substituted with 1-2 $R^{15}$ and 0-2 $R^{16}$.

In some embodiments, $R^3$ and $R^4$ are independently hydrogen, or unsubstituted or substituted $C_1$-$C_6$ alkyl, wherein any substituted group of $R^3$ and $R^4$ is substituted with 1-4 $R^{12}$; $R^5$ and $R^6$ are each independently selected from the group consisting of hydrogen, and unsubstituted or substituted $C_1$-$C_6$ alkyl, wherein any substituted group of $R^5$ and $R^6$ is substituted with 1-2 $R^{15}$ and 0-2 $R^{16}$; or $R^4$ and $R^5$ are taken together with the intervening atoms to which they are attached to form an unsubstituted or substituted monocyclic 4- to 7-membered heterocyclic ring, wherein if the heterocyclic ring is substituted then the heterocyclic ring is substituted with 1-4 $R^{12}$.

In some embodiments, $R^3$ is hydrogen; $R^4$ is hydrogen, or unsubstituted or substituted $C_1$-$C_6$ alkyl; $R^5$ is hydrogen, or unsubstituted or substituted $C_1$-$C_6$ alkyl; or $R^4$ and $R^5$ are taken together with the intervening atoms to which they are attached to form an unsubstituted or substituted monocyclic 4- to 7-membered heterocyclic ring, wherein if the heterocyclic ring is substituted then the heterocyclic ring is substituted with 1-4 $R^{12}$; $R^6$ is hydrogen.

In some embodiments, $R^3$ is hydrogen; $R^4$ is hydrogen, methyl, ethyl, n-propyl, propyl, n-butyl, i-butyl, sec-butyl, or tert-butyl; $R^5$ is hydrogen, methyl, ethyl, n-propyl, i-propyl, n-butyl, i-butyl, sec-butyl, or tert-butyl; or $R^4$ and $R^5$ are taken together with the intervening atoms to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted pyrrolidinonyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl, wherein if the heterocyclic ring is substituted then the heterocyclic ring is substituted with 1-4 $R^{12}$; $R^6$ is hydrogen.

In some embodiments, $R^3$ and $R^4$ are independently hydrogen, or unsubstituted or substituted $C_1$-$C_6$ alkyl, wherein any substituted group of $R^3$ and $R^4$ is substituted with 1-4 $R^{12}$; or $R^5$ and $R^6$ are taken together with the carbon atom with to which they are attached to form a monocyclic 4- to 7-membered carbocyclic ring, wherein if the carbocyclic ring is substituted then the carbocyclic ring is substituted with 1-4 $R^{12}$.

In some embodiments,

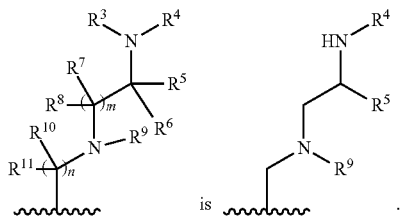 is

In some embodiments,

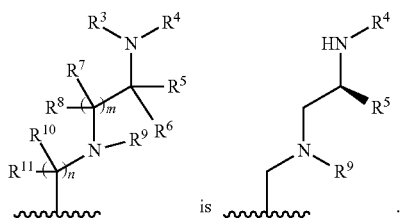 is

In some embodiments,

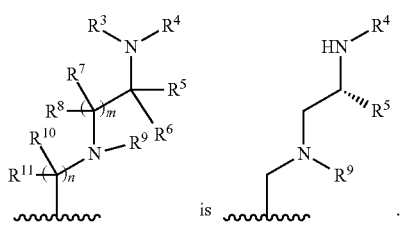 is

In some embodiments, $R^4$ and $R^5$ are taken together with the intervening atoms to which they are attached to form:

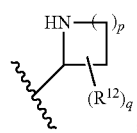;

p is 1, 2, or 3; and q is 0, 1, or 2.

In some embodiments, $R^4$ and $R^5$ are taken together with the intervening atoms to which they are attached to form:

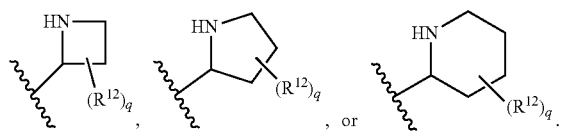

In some embodiments, $R^4$ and $R^5$ are taken together with the intervening atoms to which they are attached to form:

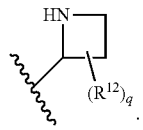

In some embodiments, $R^4$ and $R^5$ are taken together with the intervening atoms to which they are attached to form:

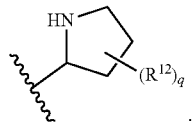

In some embodiments, $R^4$ and $R^5$ are taken together with the intervening atoms to which they are attached to form:

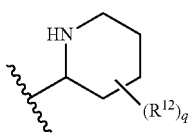

In some embodiments,

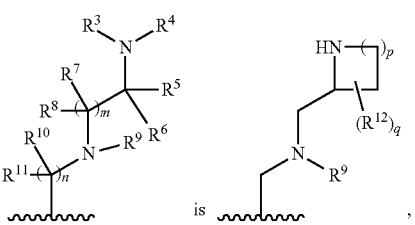 is wherein, p is 1, 2, or 3; and q is 0, 1, or 2.

In some embodiments, p is 1. In some embodiments, p is 2. In some embodiments, p is 3.

In some embodiments, q is 0. In some embodiments, q is 1. In some embodiments, q is 2.

In some embodiments,

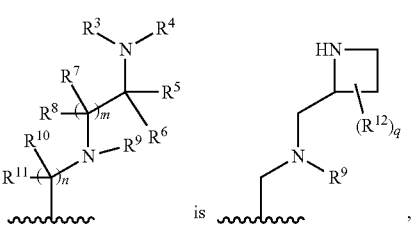 is

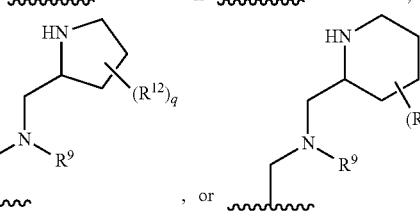, 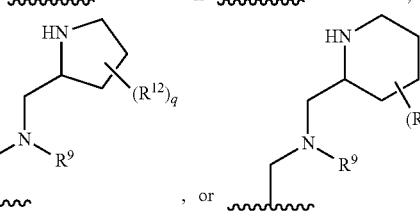, or 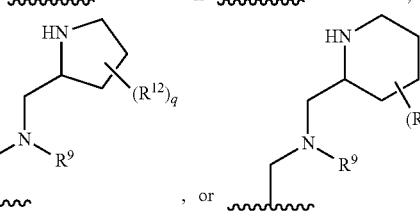.

In some embodiments,

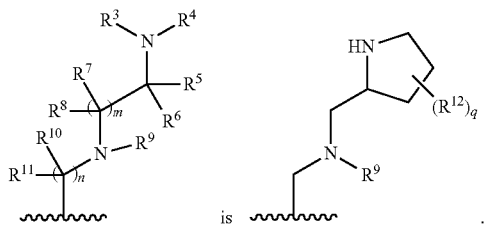

In some embodiments,

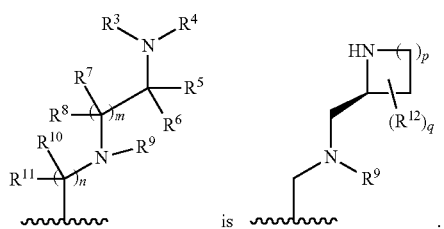

In some embodiments,

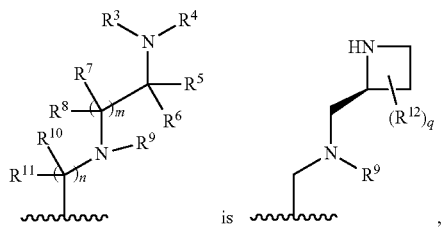

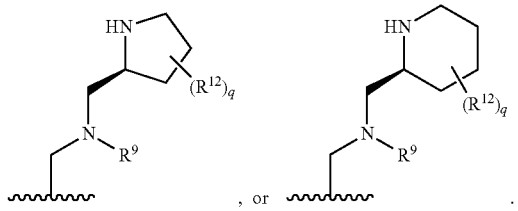

In some embodiments,

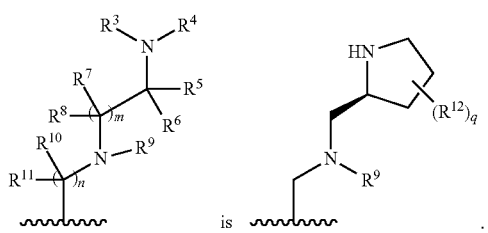

In some embodiments,

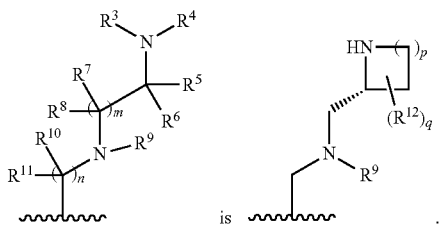

In some embodiments,

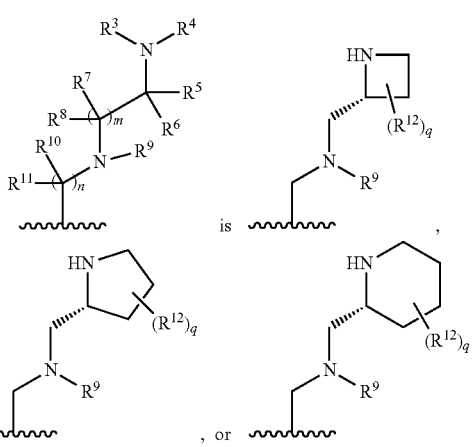

In some embodiments,

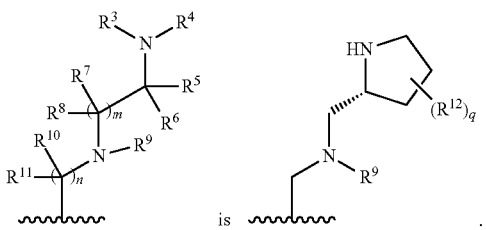

In some embodiments, $R^9$ is unsubstituted or substituted $C_1$-$C_6$ alkyl, or unsubstituted or substituted benzyl, wherein if $R^9$ is substituted then $R^9$ is substituted with 1-4 $R^{12}$. In some embodiments, $R^9$ is methyl, ethyl, n-propyl, i-propyl, n-butyl, i-butyl, sec-butyl, tert-butyl, or benzyl. In some embodiments, $R^9$ is methyl, ethyl, or benzyl. In some embodiments, $R^9$ is methyl, or ethyl. In some embodiments, $R^9$ is methyl.

In some embodiments, n is 1 and

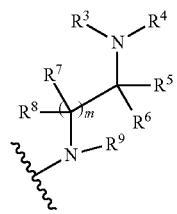

is R as described in any one of Table A, B, and/or C.

In some embodiments, $R^{13}$ is as described in Table A, B, and/or C. In some embodiments, $R^{14}$ is as described in Table A, B, and/or C. In some embodiments, $R^{15}$ is as described in Table A, B, and/or C. In some embodiments, $R^{16}$ is as described in Table A, B, and/or C. In some embodiments, $R^A$ is as described in Table A, B, and/or C. In some embodiments, $R^B$ is as described in Table A, B, and/or C. In some embodiments, $R^{13}$, $R^{14}$ are as described in Table A, B, and/or C. In some embodiments, $R^{15}$, $R^{16}$ are as described in Table A, B, and/or C. In some embodiments, $R^A$, $R^B$ are as described in Table A, B, and/or C. In some embodiments, $R^{13}$, $R^{14}$, $R^{15}$, $R^{16}$, $R^A$, $R^B$, are as described in Table A, B, and/or C.

In some embodiments, the compound of Formula (I), or a pharmaceutically acceptable salt, pharmaceutically acceptable solvate, diastereomeric mixture, individual enantiomers or prodrug thereof, has the structure of Formula (II), or a pharmaceutically acceptable salt or solvate thereof:

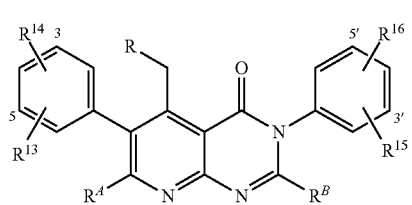

Formula (II)

wherein,

R, $R^{13}$, $R^{14}$, $R^{15}$, $R^{16}$, $R^A$, $R^B$ are as described in Table A;

or a pharmaceutically acceptable salt, pharmaceutically acceptable solvate, diastereomeric mixture, individual enantiomers or prodrug thereof.

In some embodiments, the compound of Formula (I), or a pharmaceutically acceptable salt, pharmaceutically acceptable solvate, diastereomeric mixture, individual enantiomers or prodrug thereof, has the structure of Formula (III), or a pharmaceutically acceptable salt or solvate thereof:

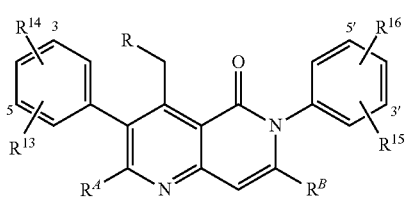

Formula (III)

wherein,

R, $R^{13}$, $R^{14}$, $R^{15}$, $R^{16}$, $R^A$, $R^B$ are as described in Table B;

or a pharmaceutically acceptable salt, pharmaceutically acceptable solvate, diastereomeric mixture, individual enantiomers or prodrug thereof.

In some embodiments, the compound of Formula (I), or a pharmaceutically acceptable salt, pharmaceutically acceptable solvate, diastereomeric mixture, individual enantiomers or prodrug thereof, has the structure of Formula (IV), or a pharmaceutically acceptable salt or solvate thereof:

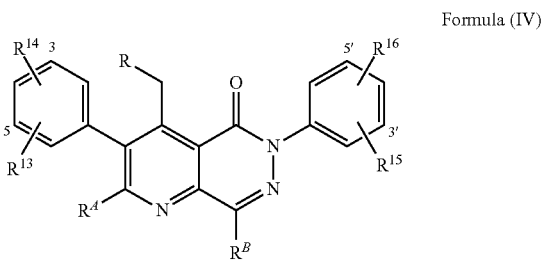

Formula (IV)

wherein,

R, $R^{13}$, $R^{14}$, $R^{15}$, $R^{16}$, $R^A$, $R^B$ are as described in Table C;

or a pharmaceutically acceptable salt, pharmaceutically acceptable solvate, diastereomeric mixture, individual enantiomers or prodrug thereof.

Any combination of the groups described above for the various variables is contemplated herein. Throughout the specification, groups and substituents thereof are chosen by one skilled in the field to provide stable moieties and compounds.

Exemplary compounds of Formula (I) include the compounds described in the following Tables:

TABLE A

| Cmpd # | R | $R^{13}$ | $R^{14}$ | $R^{15}$ | $R^{16}$ | $R^A$ | $R^B$ |
|---|---|---|---|---|---|---|---|
| A-1 | -N(CH₃)CH₂CH₂NH₂ | 3-Me | 5-Me | 3'-OH | | H | H |

TABLE A-continued

| Cmpd # | R | R13 | R14 | R15 | R16 | RA | RB |
|---|---|---|---|---|---|---|---|
| A-2 | -N(CH2CH3)CH2CH2NH2 | 3-Me | 5-Me | 3'-OH | H | H | H |
| A-3 | -N(CH2CH3)CH2CH2NH2 | 3-Cl | 5-Me | 3'-OH | 5'-F | H | H |
| A-4 | -N(CH2CH2CH3)CH2CH2NH2 | 3-Me | 5-Me | 3'-OH | H | H | H |
| A-5 | -N(CH2Ph)CH2CH2NH2 | 3-Me | 5-Me | 3'-OH | H | H | H |
| A-6 | -N(CH3)CH2CH2NHCH2Ph | 3-Me | 5-Me | 3'-OH | H | H | H |
| A-7 | -N(CH3)CH(CH3)CH2NH2 | 3-Me | 5-Me | 3'-OH | H | H | H |
| A-8 | -N(CH3)CH2C(CH3)(NH2) | 3-Me | 5-Me | 3'-OH | H | H | H |
| A-9 | -N(CH2CH3)CH2C(CH3)(NH2) | 3-Me | 5-Me | 3'-OH | H | H | H |

TABLE A-continued

| Cmpd # | R | R¹³ | R¹⁴ | R¹⁵ | R¹⁶ | Rᴬ | Rᴮ |
|---|---|---|---|---|---|---|---|
| A-10 | 3-aminopyrrolidin-1-yl | 3-Me | 5-Me | 3'-OH | H | H | H |
| A-11 | 2-(aminomethyl)pyrrolidin-1-yl | 3-Me | 5-Me | 3'-OH | H | H | H |
| A-12 | N-methyl-N-((1-aminocyclopentyl)methyl)amino | 3-Me | 5-Me | 3'-OH | H | H | H |
| A-13 | N-methyl-N-(piperidin-2-ylmethyl)amino | 3-Me | 5-Me | 3'-OH | H | H | H |
| A-14 | N-methyl-N-(piperidin-2-ylmethyl)amino | 3-Me | 5-Me | 3'-OH | H | H | H |
| A-15 | N-methyl-N-((S)-piperidin-2-ylmethyl)amino | 3-Me | 5-Me | 3'-OH | H | H | H |
| A-16 | N-methyl-N-(pyrrolidin-2-ylmethyl)amino | 3-Me | 5-Me | 3'-OH | H | H | H |
| A-17 | N-methyl-N-((S)-pyrrolidin-2-ylmethyl)amino | 3-Me | 5-Me | 3'-OH | H | H | H |

TABLE A-continued

| Cmpd # | R | R13 | R14 | R15 | R16 | R^A | R^B |
|---|---|---|---|---|---|---|---|
| A-18 | N-methyl-N-(azetidin-2-ylmethyl)amino | 3-Me | 5-Me | 3'-OH | H | H | H |
| A-19 | N-methyl-N-(morpholin-3-ylmethyl)amino | 3-Me | 5-Me | 3'-OH | H | H | H |
| A-20 | N-methyl-N-(piperidin-2-ylmethyl)amino | 2-Me | H | 3'-OH | H | H | H |
| A-21 | N-methyl-N-(piperidin-2-ylmethyl)amino | 3-Me | H | 3'-OH | H | H | H |
| A-22 | N-methyl-N-(piperidin-2-ylmethyl)amino | 3-isopropyl | H | 3'-OH | H | H | H |
| A-23 | N-methyl-N-(piperidin-2-ylmethyl)amino | 3-OMe | H | 3'-OH | H | H | H |
| A-24 | N-methyl-N-(piperidin-2-ylmethyl)amino | 3-Cl | H | 3'-OH | H | H | H |
| A-25 | N-methyl-N-(piperidin-2-ylmethyl)amino | 3-Me | 5-F | 3'-OH | H | H | H |

TABLE A-continued

| Cmpd # | R | R13 | R14 | R15 | R16 | R^A | R^B |
|---|---|---|---|---|---|---|---|
| A-26 | N-methyl-(piperidin-2-yl)methylamino | 2-Me | 3-F | 3'-OH | H | H | H |
| A-27 | N-methyl-(piperidin-2-yl)methylamino | 3-Me | 5-Me | 3'-OH | 5'-F | H | H |
| A-28 | N-methyl-(piperidin-2-yl)methylamino | 3-Me | 5-Cl | 3'-OH | 5'-F | H | H |
| A-29 | N-methyl-(piperidin-2-yl)methylamino | 3-Me | 5-Cl | 3'-OH | H | H | H |
| A-30 | N-methyl-(pyrrolidin-2-yl)methylamino | 3-Me | 5-Cl | 3'-OH | H | H | H |
| A-31 | N-methyl-(pyrrolidin-2-yl)methylamino | 3-Me | 5-Cl | 3-CONH₂ | H | H | H |
| A-32 | N-methyl-(pyrrolidin-2-yl)methylamino | 3-(CH₂)₂OH | H | 3'-OH | H | H | H |
| A-33 | N-methyl-(pyrrolidin-2-yl)methylamino | 3-MeO | H | 3'-OH | H | H | H |

TABLE A-continued

| Cmpd # | R | R¹³ | R¹⁴ | R¹⁵ | R¹⁶ | R^A | R^B |
|---|---|---|---|---|---|---|---|
| A-34 | N-methyl-(pyrrolidin-2-yl)methylamino | 3-CH₂OH | H | 3'-OH | H | H | H |
| A-35 | N-methyl-(pyrrolidin-2-yl)methylamino | 3-Cl | 5-F | 3'-OH | H | H | H |
| A-36 | N-methyl-(pyrrolidin-2-yl)methylamino | 3-Me | 5-F | 3'-OH | H | H | H |
| A-37 | N-methyl-(pyrrolidin-2-yl)methylamino | 3-Me | 5-CH₂OH | 3'-OH | H | H | H |
| A-38 | N-methyl-(pyrrolidin-2-yl)methylamino | 3-Cl | 5-CH₂OH | 3'-OH | H | H | H |
| A-39 | N-methyl-(pyrrolidin-2-yl)methylamino | 3-Me | 5-Me | 3'-CONH₂ | H | H | H |
| A-40 | N-methyl-(pyrrolidin-2-yl)methylamino | 3-Me | 5-Me | 3'-CH₂OH | H | H | H |
| A-41 | N-methyl-(pyrrolidin-2-yl)methylamino | 3-Me | 5-Me | 4'-OH | H | H | H |

TABLE A-continued

| Cmpd # | R | R¹³ | R¹⁴ | R¹⁵ | R¹⁶ | $R^A$ | $R^B$ |
|---|---|---|---|---|---|---|---|
| A-42 | N-methyl-(2S)-pyrrolidinylmethyl | 3-Me | 5-Me | 3'-CN | H | H | H |
| A-43 | N-methyl-(2S)-pyrrolidinylmethyl | 3-Me | 5-Me | 3'-CONHMe | H | H | H |
| A-44 | N-methyl-(2S)-pyrrolidinylmethyl | 3-Me | 5-Me | 3'-OH | 5'-Me | H | H |
| A-45 | N-methyl-(2S)-pyrrolidinylmethyl | 3-Me | 5-Me | 3'-OH | 5'-F | H | H |
| A-46 | N-methyl-(2S)-pyrrolidinylmethyl | 3-Me | 5-Me | 3'-CN | 5'-F | H | H |
| A-47 | N-methyl-(2S)-pyrrolidinylmethyl | 3-Me | 5-Cl | 3'-OH | 5'-F | H | H |
| A-48 | N-methyl-(2S)-pyrrolidinylmethyl | 3-Me | 5-Cl | 3'-OH | 5'-CF₃ | H | H |
| A-49 | N-methyl-(2S)-pyrrolidinylmethyl | 3-Me | 5-Cl | 3'-OH | 5'-Cl | H | H |

TABLE A-continued

| Cmpd # | R | R13 | R14 | R15 | R16 | R$^A$ | R$^B$ |
|---|---|---|---|---|---|---|---|
| A-50 | -N(CH₃)-CH₂-[(S)-pyrrolidin-2-yl] | 3-Me | 5-Cl | 3'-CONH$_2$ | 5'-F | H | H |
| A-51 | -N(CH₃)-CH₂-[(R)-pyrrolidin-2-yl] | 3-Me | 5-Cl | 3'-CONH$_2$ | 5'-F | H | H |
| A-52 | -N(CH₃)-CH₂-[(S)-pyrrolidin-2-yl] | 3-Me | 5-Cl | 3'-OH | 5'-OCF$_3$ | H | H |
| A-53 | -N(CH₃)-CH₂-[(R)-pyrrolidin-2-yl] | 3-Me | 5-Cl | 3'-OH | 5'-F | H | H |
| A-54 | -N(CH₃)-CH₂-[(S)-pyrrolidin-2-yl] | 3-Me | 5-Cl | 3'-OH | 6'-F | H | H |
| A-55 | -N(CH₃)-CH₂-[(S)-pyrrolidin-2-yl] | 3-Me | 5-Me | 3'-OH | 5'-F | H | Me |
| A-56 | -N(CH₃)-CH₂-[(S)-pyrrolidin-2-yl] | 3-Me | 5-Cl | 3'-OH | 5'-F | H | Me |
| A-57 | -N(CH₃)-CH₂-[(S)-pyrrolidin-2-yl] | 3-Me | 5-Cl | 3'-OH | H | H | Et |

TABLE A-continued

| Cmpd # | R | R13 | R14 | R15 | R16 | R^A^ | R^B^ |
|---|---|---|---|---|---|---|---|
| A-58 | -N(CH3)-CH2-[pyrrolidin-2-yl (HN)] | 3-Me | 5-Cl | 3'-OH | H | H | iPr |
| A-59 | -N(CH3)-CH2-[pyrrolidin-2-yl (HN)] | 3-Me | 5-Cl | 3'-OH | 5'-F | H | Me |
| A-60 | -N(CH3)-CH2-[pyrrolidin-2-yl (HN)] | 3-Me | 5-Cl | 3'-CN | 5'-F | H | Me |
| A-61 | -N(CH3)-CH2-C(=NH2)(CH2CH3) | 3-Me | 5-Me | 3'-OH | H | H | H |
| A-62 | -N(CH3)-CH2-C(=NH2)(CH2CH3) | 3-Me | 5-Me | 3'-OH | 5'-F | H | H |
| A-63 | -N(CH3)-CH2-C(=NH2)(CH2CH3) | 3-Me | 5-Me | 3'-OH | 5'-CF3 | H | H |
| A-64 | -N(CH3)-CH2-C(=NH2)(CH2CH3) | 3-Me | 5-Me | 3'-CONH2 | 5'-F | H | H |
| A-65 | -N(CH3)-CH2-C(=NH2)(CH2CH3) | 3-Me | 5-Cl | 3'-OH | 5'-CF3 | H | H |

TABLE A-continued
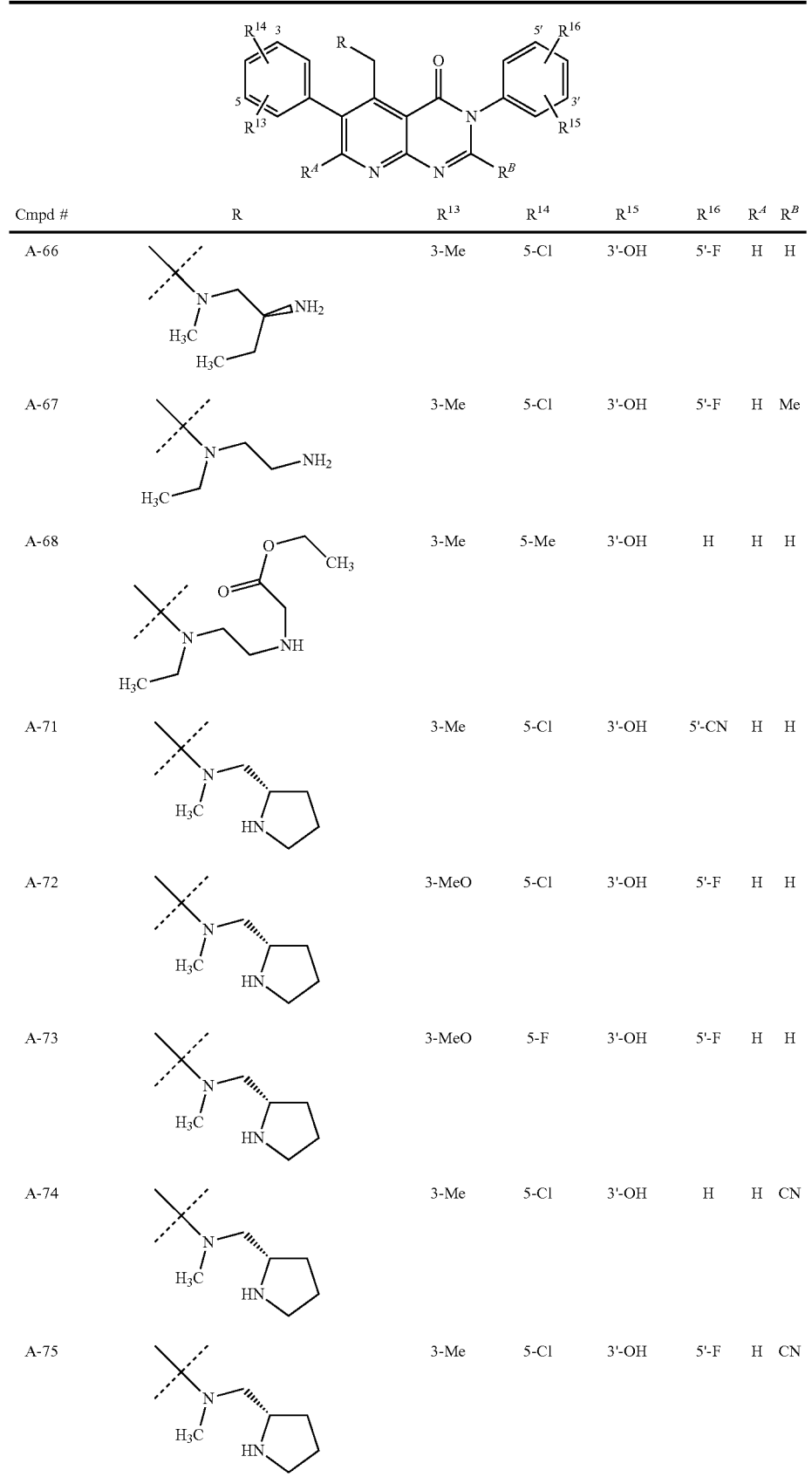
| Cmpd # | R | R¹³ | R¹⁴ | R¹⁵ | R¹⁶ | $R^A$ | $R^B$ |
|---|---|---|---|---|---|---|---|
| A-66 | | 3-Me | 5-Cl | 3'-OH | 5'-F | H | H |
| A-67 | | 3-Me | 5-Cl | 3'-OH | 5'-F | H | Me |
| A-68 | | 3-Me | 5-Me | 3'-OH | H | H | H |
| A-71 | | 3-Me | 5-Cl | 3'-OH | 5'-CN | H | H |
| A-72 | | 3-MeO | 5-Cl | 3'-OH | 5'-F | H | H |
| A-73 | | 3-MeO | 5-F | 3'-OH | 5'-F | H | H |
| A-74 | | 3-Me | 5-Cl | 3'-OH | H | H | CN |
| A-75 | | 3-Me | 5-Cl | 3'-OH | 5'-F | H | CN |

TABLE A-continued

| Cmpd # | R | R13 | R14 | R15 | R16 | RA | RB |
|---|---|---|---|---|---|---|---|
| A-76 | CH3-N-CH2-(pyrrolidine-4-F) | 3-Me | 5-Cl | 3'-OH | H | H | H |
| A-77 | CH3-N-CH2-(pyrrolidine-4-F) | 3-Me | 5-Cl | 3'-OH | 5'-F | H | H |
| A-78 | CH3-N-CH2-(pyrrolidine-4-F) | 3-MeO | 5-Cl | 3'-OH | 5'-F | H | H |
| A-79 | CH3-N-CH2-(pyrrolidine-4-F) | 3-MeO | 5-F | 3'-OH | 5'-F | H | H |
| A-80 | CH3-N-CH2-(pyrrolidine-4,4-diF) | 3-Me | 5-Cl | 3'-OH | H | H | H |
| A-81 | CH3-N-CH2-(pyrrolidine-4,4-diF) | 3-Me | 5-Cl | 3'-OH | 5'-F | H | H |
| A-82 | CH3-N-CH2-(pyrrolidine-4,4-diF) | 3-MeO | 5-Cl | 3'-OH | 5'-F | H | H |
| A-83 | CH3-N-CH2-(pyrrolidine-4,4-diF) | 3-MeO | 5-F | 3'-OH | 5'-F | H | H |

TABLE A-continued

| Cmpd # | R | R13 | R14 | R15 | R16 | R^A | R^B |
|---|---|---|---|---|---|---|---|
| A-84 | (pyrrolidine-CH2-N(CH3)-tBu, with COOH on pyrrolidine) | 3-Me | 5-Cl | 3'-OH | 5'-F | H | H |
| A-85 | (pyrrolidine-CH2-N(CH3)-tBu, with CH2COOH on pyrrolidine) | 3-Me | 5-Cl | 3'-OH | 5'-F | H | H |
| A-86 | (pyrrolidine-CH2-N(CH3)-tBu, with CH2CH2COOH on pyrrolidine) | 3-Me | 5-Cl | 3'-OH | 5'-F | H | H |
| A-87 | (pyrrolidine-CH2-N(CH2CH2OH)-tBu) | 3-Me | 5-Cl | 3'-OH | 5'-F | H | H |
| A-88 | (pyrrolidine-CH2-N(CH2COOH)-tBu) | 3-Me | 5-Cl | 3'-OH | 5'-F | H | H |
| A-89 | (azetidine-CH2-N(CH3)-tBu) | 3-Me | 5-Cl | 3'-OH | H | H | H |
| A-90 | (azetidine-CH2-N(CH3)-tBu) | 3-Me | 5-Cl | 3'-OH | 5'-F | H | H |
| A-91 | (azetidine-CH2-N(CH3)-tBu) | 3-Me | 5-Cl | 3'-OH | 5'-CF3 | H | H |

Compounds in Table A are named:

| Cmpd | Name |
| --- | --- |
| A-1 | 5-{[(2-aminoethyl)(methyl)amino]methyl}-6-(3,5-dimethylphenyl)-3-(3-hydroxyphenyl)-3H,4H-pyrido-[2,3-d]pyrimidin-4-one |
| A-2 | 5-{[(2-aminoethyl)(ethyl)amino]methyl}-6-(3,5-dimethylphenyl)-3-(3-hydroxyphenyl)-3H,4H-pyrido-[2,3-d]pyrimidin-4-one |
| A-3 | 5-(((2-aminoethyl)(ethyl)amino)methyl)-6-chloro-5-methylphenyl)-3-(3-fluoro-5-hydroxyphenyl)pyrido[2,3-d]pyrimidin-4(3H)-one |
| A-4 | 5-{[(2-aminoethyl)(propyl)amino]methyl}-6-(3,5-dimethylphenyl)-3-(3-hydroxyphenyl)-3H,4H-pyrido-[2,3-d]pyrimidin-4-one |
| A-5 | 5-{[(2-aminoethyl)(benzyl)amino]methyl}-6-(3,5-dimethylphenyl)-3-(3-hydroxyphenyl)-3H,4H-pyrido-[2,3-d]pyrimidin-4-one |
| A-6 | 5-({[2-(benzylamino)ethyl](methyl)amino}methyl)-6-(3,5-dimethylphenyl)-3-(3-hydroxyphenyl)-3H,4H-pyrido-[2,3-d]pyrimidin-4-one |
| A-7 | 5-{[(1-aminopropan-2-yl)(methyl)amino]methyl}-6-(3,5-dimethylphenyl)-3-(3-hydroxyphenyl)-3H,4H-pyrido-[2,3-d]pyrimidin-4-one |
| A-8 | 5-({[(2S)-2-aminopropyl](methyl)amino}methyl)-6-(3,5-dimethylphenyl)-3-(3-hydroxyphenyl)-3H,4H-pyrido-[2,3-d]pyrimidin-4-one |
| A-9 | 5-({[(2S)-2-aminopropyl](ethyl)amino}methyl)-6-(3,5-dimethylphenyl)-3-(3-hydroxyphenyl)-3H,4H-pyrido-[2,3-d]pyrimidin-4-one |
| A-10 | 5-[(3-aminopyrrolidin-1-yl)methyl]-6-(3,5-dimethylphenyl)-3-(3-hydroxyphenyl)-3H,4H-pyrido[2,3-d]pyrimidin-4-one |
| A-11 | 5-{[2-(aminomethyl)pyrrolidin-1-yl]methyl}-6-(3,5-dimethylphenyl)-3-(3-hydroxyphenyl)-3H,4H-pyrido-[2,3-d]pyrimidin-4-one |
| A-12 | 5-({[(1-aminocyclopentyl)methyl](methyl)amino}methyl)-6-(3,5-dimethylphenyl)-3-(3-hydroxyphenyl)-3H,4H-pyrido[2,3-d]pyrimidin-4-one |
| A-13 | 6-(3,5-dimethylphenyl)-3-(3-hydroxyphenyl)-5-{[methyl(piperidin-2-ylmethyl)amino]methyl}-3H,4H-pyrido[2,3-d]pyrimidin-4-one |
| A-14 | 6-(3,5-dimethylphenyl)-3-(3-hydroxyphenyl)-5-({methyl[(2R)-piperidin-2-ylmethyl]amino}methyl)-3H,4H-pyrido[2,3-d]pyrimidin-4-one |
| A-15 | 6-(3,5-dimethylphenyl)-3-(3-hydroxyphenyl)-5-({methyl[(2S)-piperidin-2-ylmethyl]amino}methyl)-3H,4H-pyrido[2,3-d]pyrimidin-4-one |
| A-16 | 6-(3,5-dimethylphenyl)-3-(3-hydroxyphenyl)-5-({methyl[(2R)-pyrrolidin-2-ylmethyl]amino}methyl)-3H,4H-pyrido[2,3-d]pyrimidin-4-one |
| A-17 | 6-(3,5-dimethylphenyl)-3-(3-hydroxyphenyl)-5-({methyl[(2S)-pyrrolidin-2-ylmethyl]amino}methyl)-3H,4H-pyrido[2,3-d]pyrimidin-4-one |
| A-18 | 5-({[(2S)-azetidin-2-ylmethyl](methyl)amino}methyl)-6-(3,5-dimethylphenyl)-3-(3-hydroxyphenyl)-3H,4H-pyrido[2,3-d]pyrimidin-4-one |
| A-19 | 6-(3,5-dimethylphenyl)-3-(3-hydroxyphenyl)-5-{[methyl(morpholin-3-ylmethyl)amino]methyl}-3H,4H-pyrido[2,3-d]pyrimidin-4-one |
| A-20 | 3-(3-hydroxyphenyl)-5-{[methyl(piperidin-2-ylmethyl)amino]methyl}-6-(2-methylphenyl)-3H,4H-pyrido[2,3-d]pyrimidin-4-one |
| A-21 | 3-(3-hydroxyphenyl)-5-{[methyl(piperidin-2-ylmethyl)amino]methyl}-6-(3-methylphenyl)-3H,4H-pyrido[2,3-d]pyrimidin-4-one |
| A-22 | 3-(3-hydroxyphenyl)-5-{[methyl(piperidin-2-ylmethyl)amino]methyl}-6-[3-(propan-2-yl)phenyl]-3H,4H-pyrido[2,3-d]pyrimidin-4-one |
| A-23 | 3-(3-hydroxyphenyl)-6-(3-methoxyphenyl)-5-{[methyl(piperidin-2-ylmethyl)amino]methyl}-3H,4H-pyrido[2,3-d]pyrimidin-4-one |
| A-24 | 6-(3-chlorophenyl)-3-(3-hydroxyphenyl)-5-{[methyl(piperidin-2-ylmethyl)amino]methyl}-3H,4H-pyrido[2,3-d]pyrimidin-4-one |
| A-25 | 6-(3-fluoro-5-methylphenyl)-3-(3-hydroxyphenyl)-5-{[methyl(piperidin-2-ylmethyl)amino]methyl}-3H,4H-pyrido[2,3-d]pyrimidin-4-one |
| A-26 | 6-(3-fluoro-2-methylphenyl)-3-(3-hydroxyphenyl)-5-{[methyl(piperidin-2-ylmethyl)amino]methyl}-3H,4H-pyrido[2,3-d]pyrimidin-4-one |
| A-27 | 6-(3,5-dimethylphenyl)-3-(3-fluoro-5-hydroxyphenyl)-5-({methyl[(2S)-piperidin-2-ylmethyl]amino}methyl)-3H,4H-pyrido[2,3-d]pyrimidin-4-one |
| A-28 | 6-(3-chloro-5-methylphenyl)-3-(3-fluoro-5-hydroxyphenyl)-5-({methyl[(2S)-piperidin-2-ylmethyl]amino}methyl)-3H,4H-pyrido[2,3-d]pyrimidin-4-one |
| A-29 | 6-(3-chloro-5-methylphenyl)-3-(3-hydroxyphenyl)-5-({methyl[(2S)-piperidin-2-ylmethyl]amino}methyl)-3H,4H-pyrido[2,3-d]pyrimidin-4-one |
| A-30 | 6-(3-chloro-5-methylphenyl)-3-(3-hydroxyphenyl)-5-({methyl[(2S)-pyrrolidin-2-ylmethyl]amino}methyl)-3H,4H-pyrido[2,3-d]pyrimidin-4-one |
| A-31 | 3-[6-(3-chloro-5-methylphenyl)-5-({methyl[(2S)-pyrrolidin-2-ylmethyl]amino}methyl)-4-oxo-3H,4H-pyrido[2,3-d]pyrimidin-3-yl]benzamide |
| A-32 | 6-[3-(2-hydroxyethyl)phenyl]-3-(3-hydroxyphenyl)-5-({methyl[(2S)-pyrrolidin-2-ylmethyl]amino}methyl)-3H,4H-pyrido[2,3-d]pyrimidin-4-one |
| A-33 | 6-(3,5-dimethylphenyl)-3-(3-methoxyphenyl)-5-({methyl[(2S)-pyrrolidin-2-ylmethyl]amino}methyl)-3H,4H-pyrido[2,3-d]pyrimidin-4-one |
| A-34 | 6-[3-(hydroxymethyl)phenyl]-3-(3-hydroxyphenyl)-5-({methyl[(2S)-pyrrolidin-2-ylmethyl]amino}methyl)-3H,4H-pyrido[2,3-d]pyrimidin-4-one |
| A-35 | 6-(3-chloro-5-fluorophenyl)-3-(3-hydroxyphenyl)-5-({methyl[(2S)-pyrrolidin-2-ylmethyl]amino}methyl)-3H,4H-pyrido[2,3-d]pyrimidin-4-one |
| A-36 | 6-(3-fluoro-5-methylphenyl)-3-(3-hydroxyphenyl)-5-({methyl[(2S)-pyrrolidin-2-ylmethyl]amino}methyl)-3H,4H-pyrido[2,3-d]pyrimidin-4-one |
| A-37 | 6-[3-(hydroxymethyl)-5-methylphenyl]-3-(3-hydroxyphenyl)-5-({methyl[(2S)-pyrrolidin-2-ylmethyl]amino}methyl)-3H,4H-pyrido[2,3-d]pyrimidin-4-one |
| A-38 | 6-[3-chloro-5-(hydroxymethyl)phenyl]-3-(3-hydroxyphenyl)-5-({methyl[(2S)-pyrrolidin-2-ylmethyl]amino}methyl)-3H,4H-pyrido[2,3-d]pyrimidin-4-one |
| A-39 | 3-[6-(3,5-dimethylphenyl)-5-({methyl[(2S)-pyrrolidin-2-ylmethyl]amino}methyl)-4-oxo-3H,4H-pyrido[2,3-d]pyrimidin-3-yl]benzamide |
| A-40 | 6-(3,5-dimethylphenyl)-3-[3-(hydroxymethyl)phenyl]-5-({methyl[(2S)-pyrrolidin-2-ylmethyl]amino}-methyl)-3H,4H-pyrido[2,3-d]pyrimidin-4-one |
| A-41 | 6-(3,5-dimethylphenyl)-3-(4-hydroxyphenyl)-5-({methyl[(2S)-pyrrolidin-2-ylmethyl]amino}methyl)-3H,4H-pyrido[2,3-d]pyrimidin-4-one |
| A-42 | 3-[6-(3,5-dimethylphenyl)-5-({methyl[(2S)-pyrrolidin-2-ylmethyl]amino}methyl)-4-oxo-3H,4H-pyrido[2,3-d]pyrimidin-3-yl]benzonitrile |
| A-43 | 3-[6-(3,5-dimethylphenyl)-5-({methyl[(2S)-pyrrolidin-2-ylmethyl]amino}methyl)-4-oxo-3H,4H-pyrido[2,3-d]pyrimidin-3-yl]-N-methylbenzamide |
| A-44 | 6-(3,5-dimethylphenyl)-3-(3-hydroxy-5-methylphenyl)-5-({methyl[(2S)-pyrrolidin-2-ylmethyl]amino}methyl)-3H,4H-pyrido[2,3-d]pyrimidin-4-one |
| A-45 | 6-(3,5-dimethylphenyl)-3-(3-fluoro-5-hydroxyphenyl)-5-({methyl[(2S)-pyrrolidin-2-ylmethyl]amino}methyl)-3H,4H-pyrido[2,3-d]pyrimidin-4-one |
| A-46 | 3-[6-(3,5-dimethylphenyl)-5-({methyl[(2S)-pyrrolidin-2-ylmethyl]amino}methyl)-4-oxo-3H,4H-pyrido[2,3-d]pyrimidin-3-yl]-5-fluorobenzonitrile |
| A-47 | 6-(3-chloro-5-methylphenyl)-3-(3-fluoro-5-hydroxyphenyl)-5-({methyl[(2S)-pyrrolidin-2-ylmethyl]amino}methyl)-3H,4H-pyrido[2,3-d]pyrimidin-4-one |
| A-48 | 6-(3-chloro-5-methylphenyl)-3-[3-hydroxy-5-(trifluoromethyl)phenyl]-5-({methyl[(2S)-pyrrolidin-2-ylmethyl]amino}methyl)-3H,4H-pyrido-[2,3-d]pyrimidin-4-one |
| A-49 | 3-(3-chloro-5-hydroxyphenyl)-6-(3-chloro-5-methylphenyl)-5-({methyl[(2S)-pyrrolidin-2-ylmethyl]amino}methyl)-3H,4H-pyrido[2,3-d]pyrimidin-4-one |
| A-50 | 3-[6-(3-chloro-5-methylphenyl)-5-({methyl[(2S)-pyrrolidin-2-ylmethyl]amino}methyl)-4-oxo-3H,4H-pyrido[2,3-d]pyrimidin-3-yl]-5-fluorobenzamide |

| Cmpd | Name |
|---|---|
| A-51 | 3-[6-(3-chloro-5-methylphenyl)-5-({methyl[(2R)-pyrrolidin-2-ylmethyl]amino}methyl)-4-oxo-3H,4H-pyrido[2,3-d]pyrimidin-3-yl]-5-fluorobenzamide |
| A-52 | 6-(3-chloro-5-methylphenyl)-3-[3-hydroxy-5-(trifluoromethoxy)phenyl]-5-({methyl[(2S)-pyrrolidin-2-ylmethyl]amino}methyl)-3H,4H-pyrido[2,3-d]pyrimidin-4-one |
| A-53 | 6-(3-chloro-5-methylphenyl)-3-(3-fluoro-5-hydroxyphenyl)-5-({methyl[(2R)-pyrrolidin-2-ylmethyl]amino}methyl)-3H,4H-pyrido[2,3-d]pyrimidin-4-one |
| A-54 | 6-(3-chloro-5-methylphenyl)-3-(2-fluoro-5-hydroxyphenyl)-5-({methyl[(2S)-pyrrolidin-2-ylmethyl]amino}methyl)-3H,4H-pyrido[2,3-d]pyrimidin-4-one |
| A-55 | 6-(3,5-dimethylphenyl)-3-(3-fluoro-5-hydroxyphenyl)-2-methyl-5-({methyl[(2S)-pyrrolidin-2-ylmethyl]amino}methyl)-3H,4H-pyrido[2,3-d]pyrimidin-4-one |
| A-56 | 6-(3-chloro-5-methylphenyl)-3-(3-hydroxyphenyl)-2-methyl-5-({methyl[(2S)-pyrrolidin-2-ylmethyl]amino}methyl)-3H,4H-pyrido[2,3-d]pyrimidin-4-one |
| A-57 | 6-(3-chloro-5-methylphenyl)-2-ethyl-3-(3-hydroxyphenyl)-5-({methyl[(2S)-pyrrolidin-2-ylmethyl]amino}methyl)-3H,4H-pyrido[2,3-d]pyrimidin-4-one |
| A-58 | 6-(3-chloro-5-methylphenyl)-3-(3-hydroxyphenyl)-5-({methyl[(2S)-pyrrolidin-2-ylmethyl]amino}methyl)-2-(propan-2-yl)-3H,4H-pyrido[2,3-d]pyrimidin-4-one |
| A-59 | 6-(3-chloro-5-methylphenyl)-3-(3-fluoro-5-hydroxyphenyl)-2-methyl-5-({methyl[(2S)-pyrrolidin-2-ylmethyl]amino}methyl)-3H,4H-pyrido[2,3-d]pyrimidin-4-one |
| A-60 | 3-[6-(3-chloro-5-methylphenyl)-2-methyl-5-({methyl[(2S)-pyrrolidin-2-ylmethyl]amino}methyl)-4-oxo-3H,4H-pyrido[2,3-d]pyrimidin-3-yl]-5-fluorobenzonitrile |
| A-61 | 5-({[(2S)-2-aminobutyl](methyl)amino}methyl)-6-(3,5-dimethylphenyl)-3-(3-hydroxyphenyl)-3H,4H-pyrido[2,3-d]pyrimidin-4-one |
| A-62 | 5-({[(2S)-2-aminobutyl](methyl)amino}methyl)-6-(3,5-dimethylphenyl)-3-(3-fluoro-5-hydroxyphenyl)-3H,4H-pyrido[2,3-d]pyrimidin-4-one |
| A-63 | 5-({[(2S)-2-aminobutyl](methyl)amino}methyl)-6-(3,5-dimethylphenyl)-3-[3-hydroxy-5-(trifluoromethyl)phenyl]-3H,4H-pyrido[2,3-d]pyrimidin-4-one |
| A-64 | 3-[5-({[(2S)-2-aminobutyl](methyl)amino}methyl)-6-(3,5-dimethylphenyl)-4-oxo-3H,4H-pyrido[2,3-d]pyrimidin-3-yl]-5-fluorobenzamide |
| A-65 | 5-({[(2S)-2-aminobutyl](methyl)amino}methyl)-6-(3-chloro-5-methylphenyl)-3-[3-hydroxy-5-(trifluoromethyl)phenyl]-3H,4H-pyrido[2,3-d]pyrimidin-4-one |
| A-66 | 5-({[(2S)-2-aminobutyl](methyl)amino}methyl)-6-(3-chloro-5-methylphenyl)-3-(3-fluoro-5-hydroxyphenyl)-3H,4H-pyrido[2,3-d]pyrimidin-4-one |
| A-67 | 5-{[(2-aminoethyl)(ethyl)amino]methyl}-6-(3-chloro-5-methylphenyl)-3-(3-fluoro-5-hydroxyphenyl)-2-methyl-3H,4H-pyrido[2,3-d]pyrimidin-4-one |
| A-68 | ethyl 2-{[2-({[3-(3,5-dimethylphenyl)-6-(3-hydroxyphenyl)-4-oxo-3H,4H-pyrido[2,3-d]pyrimidin-5-yl]methyl}(ethyl)amino)ethyl]amino}acetate |
| A-71 | 6-(3-methyl-5-chlorophenyl)-3-(3-cyano-5-hydroxyphenyl)-5-({methyl[(2S)-pyrrolidin-2-ylmethyl]amino}methyl)-3H,4H-pyrido[2,3-d]pyrimidin-4-one |
| A-72 | 6-(3-methoxy-5-chlorophenyl)-3-(3-fluoro-5-hydroxyphenyl)-5-({methyl[(2S)-pyrrolidin-2-ylmethyl]amino}methyl)-3H,4H-pyrido[2,3-d]pyrimidin-4-one |
| A-73 | 6-(3-methyl-5-fluorophenyl)-3-(3-fluoro-5-hydroxyphenyl)-5-({methyl[(2S)-pyrrolidin-2-ylmethyl]amino}methyl)-3H,4H-pyrido[2,3-d]pyrimidin-4-one |
| A-74 | 6-(3-methyl-5-chlorophenyl)-3-(3-hydroxyphenyl)-2-cyano-5-({methyl[(2S)-pyrrolidin-2-ylmethyl]amino}methyl)-3H,4H-pyrido[2,3-d]pyrimidin-4-one |
| A-75 | 6-(3-methyl-5-chlorophenyl)-3-(3-fluoro-5-hydroxyphenyl)-2-cyano-5-({methyl[(2S)-pyrrolidin-2-ylmethyl]amino}methyl)-3H,4H-pyrido[2,3-d]pyrimidin-4-one |
| A-76 | 6-(3-methyl-5-chlorophenyl)-3-(3-hydroxyphenyl)-5-({methyl[(2S)-4-fluoropyrrolidin-2-ylmethyl]amino}methyl)-3H,4H-pyrido[2,3-d]pyrimidin-4-one |
| A-77 | 6-(3-methyl-5-chlorophenyl)-3-(3-fluoro-5-hydroxyphenyl)-5-({methyl[(2S)-4-fluoropyrrolidin-2-ylmethyl]amino}methyl)-3H,4H-pyrido[2,3-d]pyrimidin-4-one |
| A-78 | 6-(3-methoxy-5-chlorophenyl)-3-(3-fluoro-5-hydroxyphenyl)-5-({methyl[(2S)-4-fluoropyrrolidin-2-ylmethyl]amino}methyl)-3H,4H-pyrido[2,3-d]pyrimidin-4-one |
| A-79 | 6-(3-methoxy-5-fluorophenyl)-3-(3-fluoro-5-hydroxyphenyl)-5-({methyl[(2S)-4-fluoropyrrolidin-2-ylmethyl]amino}methyl)-3H,4H-pyrido[2,3-d]pyrimidin-4-one |
| A-80 | 6-(3-methyl-5-chlorophenyl)-3-(3-hydroxyphenyl)-5-({methyl[(2S)-4,4-difluoropyrrolidin-2-ylmethyl]amino}methyl)-3H,4H-pyrido[2,3-d]pyrimidin-4-one |
| A-81 | 6-(3-methyl-5-chlorophenyl)-3-(3-fluoro-5-hydroxyphenyl)-5-({methyl[(2S)-4,4-difluoropyrrolidin-2-ylmethyl]amino}methyl)-3H,4H-pyrido[2,3-d]pyrimidin-4-one |
| A-82 | 6-(3-methoxy-5-chlorophenyl)-3-(3-fluoro-5-hydroxyphenyl)-5-({methyl[(2S)-4,4-difluoropyrrolidin-2-ylmethyl]amino}methyl)-3H,4H-pyrido[2,3-d]pyrimidin-4-one |
| A-83 | 6-(3-methoxy-5-fluorophenyl)-3-(3-fluoro-5-hydroxyphenyl)-5-({methyl[(2S)-4,4-difluoropyrrolidin-2-ylmethyl]amino}methyl)-3H,4H-pyrido[2,3-d]pyrimidin-4-one |
| A-84 | (5S)-5-(((((6-(3-chloro-5-methylphenyl)-3-(3-fluoro-5-hydroxyphenyl)-4-oxo-3,4-dihydropyrido[2,3-d]pyrimidin-5-yl)methyl)(methyl)amino)methyl)pyrrolidine-3-carboxylic acid |
| A-85 | 2-((5S)-5-(((((6-(3-chloro-5-methylphenyl)-3-(3-fluoro-5-hydroxyphenyl)-4-oxo-3,4-dihydropyrido[2,3-d]pyrimidin-5-yl)methyl)(methyl)amino)methyl)pyrrolidin-3-yl)acetic acid |
| A-86 | 3-((5S)-5-(((((6-(3-chloro-5-methylphenyl)-3-(3-fluoro-5-hydroxyphenyl)-4-oxo-3,4-dihydropyrido[2,3-d]pyrimidin-5-yl)methyl)(methyl)amino)methyl)pyrrolidin-3-yl)propanoic acid |
| A-87 | (S)-6-(3-chloro-5-methylphenyl)-3-(3-fluoro-5-hydroxyphenyl)-5-(((2-hydroxyethyl)(pyrrolidin-2-ylmethyl)amino)methyl)pyrido[2,3-d]pyrimidin-4(3H)-one |
| A-88 | (S)-2-(((6-(3-chloro-5-methylphenyl)-3-(3-fluoro-5-hydroxyphenyl)-4-oxo-3,4-dihydropyrido[2,3-d]pyrimidin-5-yl)methyl)(pyrrolidin-2-ylmethyl)amino)acetic acid |
| A-89 | 6-(3-methyl-5-chlorophenyl)-3-(3-hydroxyphenyl)-5-({methyl[(S)-azetidin-2-ylmethyl]amino}methyl)-3H,4H-pyrido[2,3-d]pyrimidin-4-one |
| A-90 | 6-(3-methyl-5-chlorophenyl)-3-(3-fluoro-5-hydroxyphenyl)-5-({methyl[(S)-azetidin-2-ylmethyl]amino}methyl)-3H,4H-pyrido[2,3-d]pyrimidin-4-one |
| A-91 | 6-(3-methyl-5-chlorophenyl)-3-(3-hydroxy-5-trifluoromethylphenyl)-5-({methyl[(S)-azetidin-2-ylmethyl]amino}methyl)-3H,4H-pyrido[2,3-d]pyrimidin-4-one |

Other Exemplary compounds are 3-(3-hydroxy-phenyl)-5-[(methyl-piperidin-2-ylmethyl-amino)-methyl]-6-naphthalen-1-yl-3H-pyrido[2,3-d]pyrimidin-4-one as compound A-69 and 6-(2-Fluoro-3,5-dimethyl-phenyl)-3-(3-hydroxy-phenyl)-5-[(methyl-piperidin-2-ylmethyl-amino)-methyl]-3H-pyrido[2,3-d]pyrimidin-4-one as compound A-70.

TABLE B

| Cmpd # | R | $R^{13}$ | $R^{14}$ | $R^{15}$ | $R^{16}$ | $R^A$ | $R^B$ |
|---|---|---|---|---|---|---|---|
| B-1 | (structure: N-methyl, isobutyl, CH₂CH(NH₂)-) | 3-Me | 5-Me | 3'-OH | H | H | H |

TABLE B-continued

| Cmpd # | R | R13 | R14 | R15 | R16 | R4 | RB |
|---|---|---|---|---|---|---|---|
| B-2 | N(CH3)(CH2CH3)-CH2-C(NH2) | 3-Me | 5-Cl | 3'-OH | H | H | H |
| B-3 | N(CH3)(CH2CH3)-CH2-C(NH2) | 3-Me | 5-Cl | 3'-OH | 5'-F | H | H |
| B-4 | N(CH3)(CH2CH3)-CH2-C(NH2) | 3-Me | 5-Cl | 3'-OH | 5'-F | H | Me |
| B-5 | N(CH3)(CH2CH3)-CH2-C(NH2) | 3-Me | 5-Cl | 3'-OH | 5'-F | H | CN |
| B-6 | N(CH3)(CH2CH3)-CH2-C(NH2) | 3-Me | 5-Cl | 3'-OH | 5'-F | H | $CF_3$ |
| B-7 | N(CH3)(CH2CH3)-CH2-C(NH2) | 3-Me | 5-Cl | 3'-OH | 5'-$CF_3$ | H | H |
| B-8 | N(CH3)-CH2-pyrrolidine | 3-Me | 5-Cl | 3'-OH | H | H | H |
| B-9 | N(CH3)-CH2-pyrrolidine | 3-Me | 5-Cl | 3'-OH | H | H | Me |
| B-10 | N(CH3)-CH2-pyrrolidine | 3-Me | 5-Cl | 3'-OH | 5'-F | H | H |
| B-11 | N(CH3)-CH2-pyrrolidine | 3-Me | 5-Cl | 3'-OH | 5'-F | H | Me |
| B-12 | N(CH3)-CH2-pyrrolidine | 3-Me | 5-Cl | 3'-OH | 5'-F | H | $CF_3$ |
| B-13 | N(CH3)-CH2-pyrrolidine | 3-Me | 5-Cl | 3'-OH | 5'-$CF_3$ | H | H |
| B-14 | N(CH3)-CH2-pyrrolidine | 3-Me | 5-Cl | 3'-OH | 5'-$CF_3$ | H | Me |
| B-15 | N(CH3)-CH2-pyrrolidine | 3-Me | 5-Cl | 3'-OH | 5'-$CF_3$ | H | CN |
| B-16 | N(CH3)-CH2-pyrrolidine | 3-Me | 5-Cl | 3'-OH | 5'-CN | H | H |
| B-17 | N(CH3)-CH2-pyrrolidine | 3-Me | 5-F | 3'-OH | H | H | H |
| B-18 | N(CH3)-CH2-pyrrolidine | 3-Me | 5-F | 3'-OH | H | H | Me |
| B-19 | N(CH3)-CH2-pyrrolidine | 3-Me | 5-F | 3'-OH | 5'-F | H | H |
| B-20 | N(CH3)-CH2-pyrrolidine | 3-Me | 5-F | 3'-OH | 5'-F | H | Me |
| B-21 | N(CH3)-CH2-pyrrolidine | 3-Me | 5-F | 3'-OH | 5'-F | H | $CF_3$ |

TABLE B-continued

| Cmpd # | R | R13 | R14 | R15 | R16 | R4 | RB |
|---|---|---|---|---|---|---|---|
| B-22 | N-methyl-(pyrrolidin-2-ylmethyl)amino | 3-Me | 5-F | 3'-OH | 5'-CF$_3$ | H | H |
| B-23 | N-methyl-(pyrrolidin-2-ylmethyl)amino | 3-Me | 5-F | 3'-OH | 5'-CF$_3$ | H | Me |
| B-24 | N-methyl-(pyrrolidin-2-ylmethyl)amino | 3-Me | 5-F | 3'-OH | 5'-CF$_3$ | H | CN |
| B-25 | N-methyl-(pyrrolidin-2-ylmethyl)amino | 3-Me | 5-Me | 3'-OH | H | H | H |
| B-26 | N-methyl-(pyrrolidin-2-ylmethyl)amino | 3-Me | 5-Me | 3'-OH | H | H | Me |
| B-27 | N-methyl-(pyrrolidin-2-ylmethyl)amino | 3-Me | 5-Me | 3'-OH | 5'-F | H | H |
| B-28 | N-methyl-(pyrrolidin-2-ylmethyl)amino | 3-Me | 5-Me | 3'-OH | 5'-F | H | Me |
| B-29 | N-methyl-(pyrrolidin-2-ylmethyl)amino | 3-Me | 5-Me | 3'-OH | 5'-F | H | CF$_3$ |
| B-30 | N-methyl-(pyrrolidin-2-ylmethyl)amino | 3-Me | 5-Me | 3'-OH | 5'-CF$_3$ | H | H |
| B-31 | N-methyl-(pyrrolidin-2-ylmethyl)amino | 3-Me | 5-Me | 3'-OH | 5'-CF$_3$ | H | Me |
| B-32 | N-methyl-(pyrrolidin-2-ylmethyl)amino | 3-Me | 5-Me | 3'-OH | 5'-CF$_3$ | H | CN |
| B-33 | N-methyl-(pyrrolidin-2-ylmethyl)amino | 3-Me | 5-Me | 3'-OH | 5'-CN | H | H |
| B-34 | N-methyl-(pyrrolidin-2-ylmethyl)amino | 3-MeO | 5-Cl | 3'-OH | 5'-F | H | H |
| B-35 | N-methyl-(pyrrolidin-2-ylmethyl)amino | 3-MeO | 5-F | 3'-OH | 5'-F | H | H |

Compounds in Table B are named:

| Cmpd | Name |
|---|---|
| B-1 | (S)-4-(((2-aminobutyl)(methyl)amino)methyl)-3-(3,5-dimethylphenyl)-6-(3-hydroxyphenyl)-1,6-naphthyridin-5(6H)-one |
| B-2 | (S)-4-(((2-aminobutyl)(methyl)amino)methyl)-3-(3-chloro-5-methylphenyl)-6-(3-hydroxyphenyl)-1,6-naphthyridin-5(6H)-one |
| B-3 | (S)-4-(((2-aminobutyl)(methyl)amino)methyl)-3-(3-chloro-5-methylphenyl)-6-(3-fluoro-5-hydroxyphenyl)-1,6-naphthyridin-5(6H)-one |
| B-4 | (S)-4-(((2-aminobutyl)(methyl)amino)methyl)-3-(3-chloro-5-methylphenyl)-6-(3-fluoro-5-hydroxyphenyl)-7-methyl-1,6-naphthyridin-5(6H)-one |
| B-5 | (S)-4-(((2-aminobutyl)(methyl)amino)methyl)-3-(3-chloro-5-methylphenyl)-6-(3-fluoro-5-hydroxyphenyl)-5-oxo-5,6-dihydro-1,6-naphthyridine-7-carbonitrile |
| B-6 | (S)-4-(((2-aminobutyl)(methyl)amino)methyl)-3-(3-chloro-5-methylphenyl)-6-(3-fluoro-5-hydroxyphenyl)-7-(trifluoromethyl)-1,6-naphthyridin-5(6H)-one |
| B-7 | (S)-4-(((2-aminobutyl)(methyl)amino)methyl)-3-(3-chloro-5-methylphenyl)-6-(3-hydroxy-5-(trifluoromethyl)phenyl)-1,6-naphthyridin-5(6H)-one |
| B-8 | (S)-3-(3-chloro-5-methylphenyl)-6-(3-hydroxyphenyl)-4-((methyl(pyrrolidin-2-ylmethyl)amino)methyl)-1,6-naphthyridin-5(6H)-one |
| B-9 | (S)-3-(3-chloro-5-methylphenyl)-6-(3-hydroxyphenyl)-7-methyl-4-((methyl(pyrrolidin-2-ylmethyl)amino)methyl)-1,6-naphthyridin-5(6H)-one |
| B-10 | (S)-3-(3-chloro-5-methylphenyl)-6-(3-fluoro-5-hydroxyphenyl)-4-((methyl(pyrrolidin-2-ylmethyl)amino)methyl)-1,6-naphthyridin-5(6H)-one |
| B-11 | (S)-3-(3-chloro-5-methylphenyl)-6-(3-fluoro-5-hydroxyphenyl)-7-methyl-4-((methyl(pyrrolidin-2-ylmethyl)amino)methyl)-1,6-naphthyridin-5(6H)-one |

| Cmpd | Name |
|---|---|
| B-12 | (S)-3-(3-chloro-5-methylphenyl)-6-(3-fluoro-5-hydroxyphenyl)-4-((methyl(pyrrolidin-2-ylmethyl)amino)methyl)-7-(trifluoromethyl)-1,6-naphthyridin-5(6H)-one |
| B-13 | (S)-3-(3-chloro-5-methylphenyl)-6-(3-hydroxy-5-(trifluoromethyl)phenyl)-4-((methyl(pyrrolidin-2-ylmethyl)-amino)methyl)-1,6-naphthyridin-5(6H)-one |
| B-14 | (S)-3-(3-chloro-5-methylphenyl)-6-(3-hydroxy-5-(trifluoromethyl)phenyl)-7-methyl-4-(methyl(pyrrolidin-2-ylmethyl)amino)methyl)-1,6-naphthyridin-5(6H)-one |
| B-15 | (S)-3-(3-chloro-5-methylphenyl)-6-(3-hydroxy-5-(trifluoromethyl)phenyl)-4-((methyl(pyrrolidin-2-ylmethyl)amino)methyl)-5-oxo-5,6-dihydro-1,6-naphthyridine-7-carbonitrile |
| B-16 | (S)-3-(3-(3-chloro-5-methylphenyl)-4-((methyl-(pyrrolidin-2-ylmethyl)amino)methyl)-5-oxo-1,6-naphthyridin-6(5H)-yl)-5-hydroxybenzonitrile |
| B-17 | (S)-3-(3-fluoro-5-methylphenyl)-6-(3-hydroxyphenyl)-4-((methyl(pyrrolidin-2-ylmethyl)amino)methyl)-1,6-naphthyridin-5(6H)-one |
| B-18 | (S)-3-(3-fluoro-5-methylphenyl)-6-(3-hydroxyphenyl)-7-methyl-4-((methyl(pyrrolidin-2-ylmethyl)-amino)methyl)-1,6-naphthyridin-5(6H)-one |
| B-19 | (S)-6-(3-fluoro-5-hydroxyphenyl)-3-(3-fluoro-5-methylphenyl)-4-((methyl(pyrrolidin-2-yl-methyl)amino)methyl)-1,6-naphthyridin-5(6H)-one |
| B-20 | (S)-6-(3-fluoro-5-hydroxyphenyl)-3-(3-fluoro-5-methylphenyl)-7-methyl-4-((methyl(pyrrolidin-2-yl-methyl)amino)methyl)-1,6-naphthyridin-5(6H)-one |
| B-21 | (S)-6-(3-fluoro-5-hydroxyphenyl)-3-(3-fluoro-5-methylphenyl)-4-((methyl(pyrrolidin-2-ylmethyl)-amino)-methyl)-7-(trifluoromethyl)-1,6-naphthyridin-5(6H)-one |
| B-22 | (S)-3-(3-fluoro-5-methylphenyl)-6-(3-hydroxy-5-(trifluoromethyl)phenyl)-4-((methyl(pyrrolidin-2-ylmethyl)amino)methyl)-1,6-naphthyridin-5(6H)-one |
| B-23 | (S)-3-(3-fluoro-5-methylphenyl)-6-(3-hydroxy-5-(trifluoromethyl)phenyl)-7-methyl-4-((methyl(pyrrolidin-2-ylmethyl)amino)methyl)-1,6-naphthyridin-5(6H)-one |
| B-24 | (S)-3-(3-fluoro-5-methylphenyl)-6-(3-hydroxy-5-(trifluoromethyl)phenyl)-4-((methyl(pyrrolidin-2-ylmethyl)amino)methyl)-5-oxo-5,6-dihydro-1,6-naphthyridine-7-carbonitrile |
| B-25 | (S)-3-(3,5-dimethylphenyl)-6-(3-hydroxyphenyl)-4-((methyl(pyrrolidin-2-ylmethyl)amino)methyl)-1,6-naphthyridin-5(6H)-one |
| B-26 | (S)-3-(3,5-dimethylphenyl)-6-(3-hydroxyphenyl)-7-methyl-4-((methyl(pyrrolidin-2-ylmethyl)amino)-methyl)-1,6-naphthyridin-5(6H)-one |
| B-27 | (S)-3-(3,5-dimethylphenyl)-6-(3-fluoro-5-hydroxyphenyl)-4-((methyl(pyrrolidin-2-ylmethyl)amino)methyl)-1,6-naphthyridin-5(6H)-one |
| B-28 | (S)-3-(3,5-dimethylphenyl)-6-(3-fluoro-5-hydroxyphenyl)-7-methyl-4-((methyl(pyrrolidin-2-ylmethyl)amino)methyl)-1,6-naphthyridin-5(6H)-one |
| B-29 | (S)-3-(3,5-dimethylphenyl)-6-(3-fluoro-5-hydroxyphenyl)-4-((methyl(pyrrolidin-2-ylmethyl)amino)methyl)-7-(trifluoromethyl)-1,6-naphthyridin-5(6H)-one |
| B-30 | (S)-3-(3,5-dimethylphenyl)-6-(3-hydroxy-5-(trifluoromethyl)phenyl)-4-((methyl(pyrrolidin-2-ylmethyl)-amino)methyl)-1,6-naphthyridin-5(6H)-one |
| B-31 | (S)-3-(3,5-dimethylphenyl)-6-(3-hydroxy-5-(trifluoromethyl)phenyl)-7-methyl-4-((methyl(pyrrolidin-2-ylmethyl)amino)methyl)-1,6-naphthyridin-5(6H)-one |
| B-32 | (S)-3-(3,5-dimethylphenyl)-6-(3-hydroxy-5-(trifluoromethyl)phenyl)-4-((methyl(pyrrolidin-2-ylmethyl)amino)methyl)-5-oxo-5,6-dihydro-1,6-naphthyridine-7-carbonitrile |
| B-33 | (S)-3-(3-(3,5-dimethylphenyl)-4-((methyl(pyrrolidin-2-ylmethyl)amino)methyl)-5-oxo-1,6-naphthyridin-6(5H)-yl)-5-hydroxybenzonitrile |
| B-34 | (S)-3-(3-chloro-5-methoxyphenyl)-6-(3-fluoro-5-hydroxyphenyl)-4-((methyl(pyrrolidin-2-yl-methyl)amino)methyl)-1,6-naphthyridin-5(6H)-one |
| B-35 | (S)-6-(3-fluoro-5-hydroxyphenyl)-3-(3-fluoro-5-methoxyphenyl)-4-((methyl(pyrrolidin-2-yl-methyl)amino)methyl)-1,6-naphthyridin-5(6H)-one |

TABLE C

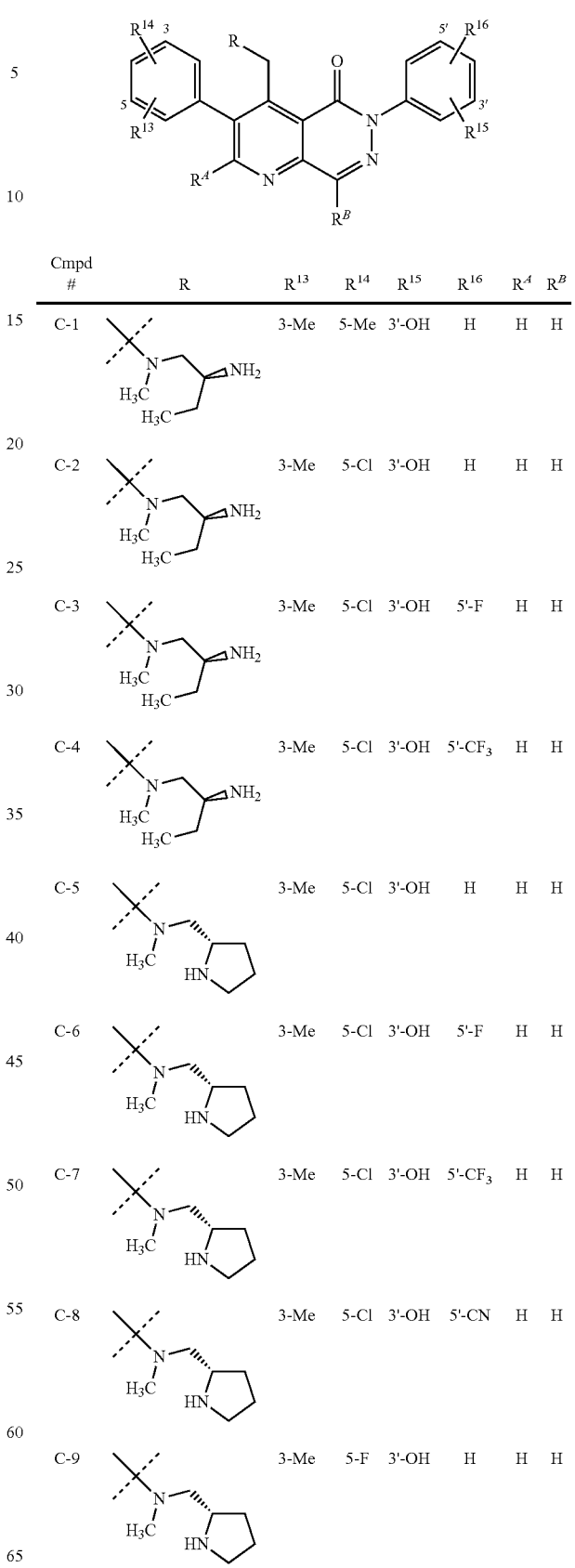

| Cmpd # | R | $R^{13}$ | $R^{14}$ | $R^{15}$ | $R^{16}$ | $R^A$ | $R^B$ |
|---|---|---|---|---|---|---|---|
| C-1 | | 3-Me | 5-Me | 3'-OH | H | H | H |
| C-2 | | 3-Me | 5-Cl | 3'-OH | H | H | H |
| C-3 | | 3-Me | 5-Cl | 3'-OH | 5'-F | H | H |
| C-4 | | 3-Me | 5-Cl | 3'-OH | 5'-CF$_3$ | H | H |
| C-5 | | 3-Me | 5-Cl | 3'-OH | H | H | H |
| C-6 | | 3-Me | 5-Cl | 3'-OH | 5'-F | H | H |
| C-7 | | 3-Me | 5-Cl | 3'-OH | 5'-CF$_3$ | H | H |
| C-8 | | 3-Me | 5-Cl | 3'-OH | 5'-CN | H | H |
| C-9 | | 3-Me | 5-F | 3'-OH | H | H | H |

TABLE C-continued

Structure: pyrido[2,3-d]pyridazinone core with substituents R, R¹³, R¹⁴, R¹⁵, R¹⁶, R^A, R^B

| Cmpd # | R | R¹³ | R¹⁴ | R¹⁵ | R¹⁶ | R^A | R^B |
|---|---|---|---|---|---|---|---|
| C-10 | (methyl)(pyrrolidin-2-ylmethyl)amino-methyl | 3-Me | 5-F | 3'-OH | 5'-F | H | H |
| C-11 | (methyl)(pyrrolidin-2-ylmethyl)amino-methyl | 3-Me | 5-F | 3'-OH | 5'-CF₃ | H | H |
| C-12 | (methyl)(pyrrolidin-2-ylmethyl)amino-methyl | 3-Me | 5-Me | 3'-OH | H | H | H |
| C-13 | (methyl)(pyrrolidin-2-ylmethyl)amino-methyl | 3-Me | 5-Me | 3'-OH | 5'-F | H | H |
| C-14 | (methyl)(pyrrolidin-2-ylmethyl)amino-methyl | 3-Me | 5-Me | 3'-OH | 5'-CF₃ | H | H |
| C-15 | (methyl)(pyrrolidin-2-ylmethyl)amino-methyl | 3-Me | 5-Me | 3'-OH | 5'-CN | H | H |
| C-16 | (methyl)(pyrrolidin-2-ylmethyl)amino-methyl | 3-MeO | 5-F | 3'-OH | 5'-F | H | H |
| C-17 | (methyl)(pyrrolidin-2-ylmethyl)amino-methyl | 3-MeO | 5-Cl | 3'-OH | 5'-F | H | H |

Compounds in Table C are named:

| Cmpd | Name |
|---|---|
| C-1 | (S)-4-(((2-aminobutyl)(methyl)amino)methyl)-3-(3,5-dimethylphenyl)-6-(3-hydroxyphenyl)pyrido[2,3-d]pyridazin-5(6H)-one |
| C-2 | (S)-4-(((2-aminobutyl)(methyl)amino)methyl)-3-(3-chloro-5-methylphenyl)-6-(3-hydroxyphenyl)pyrido[2,3-d]pyridazin-5(6H)-one |
| C-3 | (S)-4-(((2-aminobutyl)(methyl)amino)methyl)-3-(3-chloro-5-methylphenyl)-6-(3-fluoro-5-hydroxyphenyl)pyrido[2,3-d]pyridazin-5(6H)-one |
| C-4 | (S)-4-(((2-aminobutyl)(methyl)amino)methyl)-3-(3-chloro-5-methylphenyl)-6-(3-hydroxy-5-(trifluoromethyl)phenyl)pyrido[2,3-d]pyridazin-5(6H)-one |
| C-5 | (S)-3-(3-chloro-5-methylphenyl)-6-(3-hydroxyphenyl)-4-((methyl(pyrrolidin-2-ylmethyl)amino)methyl)pyrido[2,3-d]pyridazin-5(6H)-one |
| C-6 | (S)-3-(3-chloro-5-methylphenyl)-6-(3-fluoro-5-hydroxyphenyl)-4-((methyl(pyrrolidin-2-ylmethyl)amino)methyl)pyrido[2,3-d]pyridazin-5(6H)-one |
| C-7 | (S)-3-(3-chloro-5-methylphenyl)-6-(3-hydroxy-5-(trifluoromethyl)phenyl)-4-((methyl(pyrrolidin-2-ylmethyl)amino)methyl)pyrido[2,3-d]pyridazin-5(6H)-one |
| C-8 | (S)-3-(3-(3-chloro-5-methylphenyl)-4-((methyl(pyrrolidin-2-ylmethyl)amino)methyl)-5-oxopyrido[2,3-d]pyridazin-6(5H)-yl)-5-hydroxybenzonitrile |
| C-9 | (S)-3-(3-fluoro-5-methylphenyl)-6-(3-hydroxyphenyl)-4-((methyl(pyrrolidin-2-ylmethyl)amino)methyl)pyrido[2,3-d]pyridazin-5(6H)-one |
| C-10 | (S)-6-(3-fluoro-5-hydroxyphenyl)-3-(3-fluoro-5-methylphenyl)-4-((methyl(pyrrolidin-2-ylmethyl)amino)methyl)pyrido[2,3-d]pyridazin-5(6H)-one |
| C-11 | (S)-3-(3-fluoro-5-methylphenyl)-6-(3-hydroxy-5-(trifluoromethyl)phenyl)-4-((methyl(pyrrolidin-2-ylmethyl)amino)methyl)pyrido[2,3-d]pyridazin-5(6H)-one |
| C-12 | (S)-3-(3,5-dimethylphenyl)-6-(3-hydroxyphenyl)-4-((methyl(pyrrolidin-2-ylmethyl)amino)methyl)pyrido-[2,3-d]pyridazin-5(6H)-one |
| C-13 | (S)-3-(3,5-dimethylphenyl)-6-(3-fluoro-5-hydroxyphenyl)-4-((methyl(pyrrolidin-2-ylmethyl)amino)methyl)-pyrido[2,3-d]pyridazin-5(6H)-one |
| C-14 | (S)-3-(3,5-dimethylphenyl)-6-(3-hydroxy-5-(trifluoromethyl)phenyl)-4-((methyl(pyrrolidin-2-ylmethyl)amino)methyl)pyrido[2,3-d]pyridazin-5(6H)-one |
| C-15 | (S)-3-(3-(3,5-dimethylphenyl)-4-((methyl(pyrrolidin-2-ylmethyl)amino)methyl)-5-oxopyrido[2,3-d]pyridazin-6(5H)-yl)-5-hydroxybenzonitrile |
| C-16 | (S)-3-(3,5-dimethylphenyl)-6-(3-fluoro-5-hydroxyphenyl)-4-((methyl(pyrrolidin-2-ylmethyl)amino)methyl)-pyrido[2,3-d]pyridazin-5(6H)-one |
| C-17 | (S)-3-(3-chloro-5-methoxyphenyl)-6-(3-fluoro-5-hydroxyphenyl)-4-((methyl(pyrrolidin-2-ylmethyl)amino)methyl)pyrido[2,3-d]pyridazin-5(6H)-one |

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound of Formula (A) with an acid. In some embodiments, the compound of Formula (A) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (A) is prepared as a chloride salt, sulfate salt, bromide salt, mesylate salt, maleate salt, citrate salt or phosphate salt.

In some embodiments, pharmaceutically acceptable salts are obtained by reacting a compound of Formula (A) with a base. In some embodiments, the compound of Formula (A) is acidic and is reacted with a base. In such situations, an acidic proton of the compound of Formula (A) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (A), as well as active metabolites of these compounds having the same type of activity.

In some embodiments, sites on the organic radicals (e.g. alkyl groups, aromatic rings) of compounds of Formula (A) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds of Formula (A) possess one or more stereocenters and each stereocenter exists independently in either the R or S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds of Formula (A) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (A) as set forth herein are included within the scope of the claims. In some cases, some of the herein-described compounds is a prodrug for another derivative or active compound.

In some embodiments, any one of the hydroxyl group(s), amino group(s) and/or carboxylic acid group(s) are functionalized in a suitable manner to provide a prodrug moiety. In some embodiments, the prodrug moiety is as described above.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds of Formula (A) described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as described as outlined in Scheme A.

Scheme A:

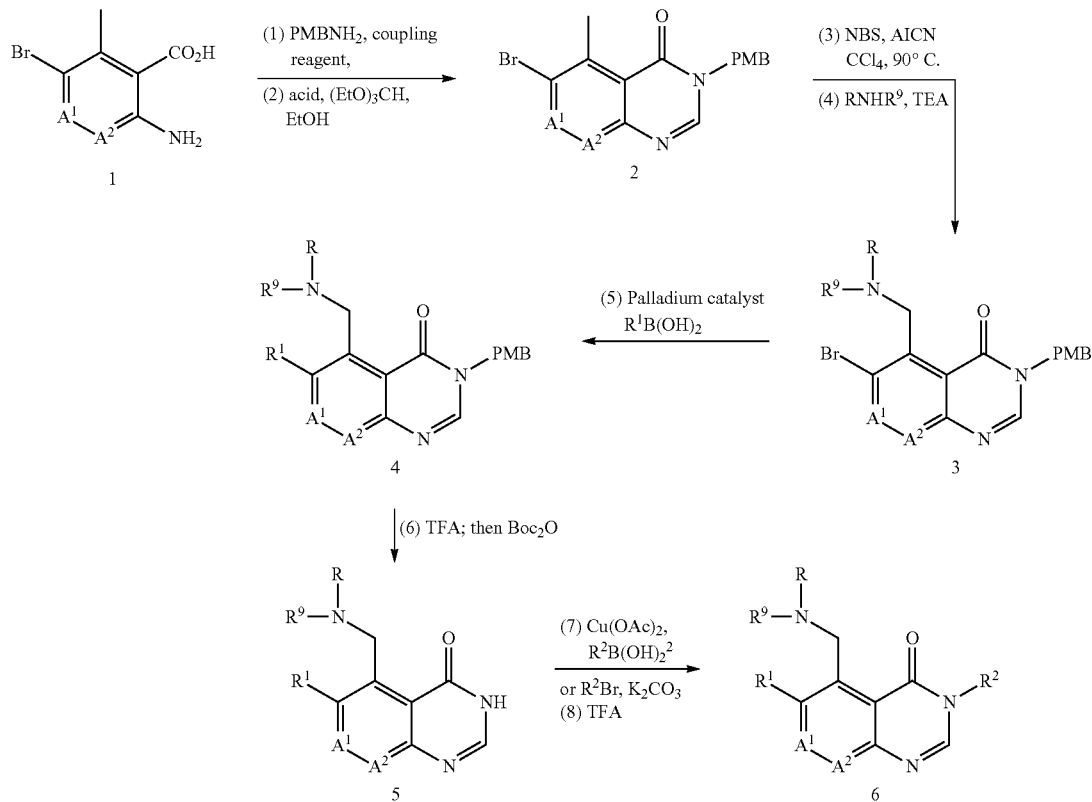

In one aspect, acid compound 1 is coupled with p-methoxybenzylamine (PMBNH$_2$), followed by the cyclization with orthoformate in the presence of an acid such as PTS to form compound 2. Compound 2 is brominated with a suitable brominating agent and then reacted with an amine, RR$^9$NH, where R can be a protected alkylaminoalkyl group and R$^9$ can be hydrogen or an alkyl group to produce compound 3. In some embodiments, bromination is performed by refluxing compound 2 with N-bromosuccinimide (NBS) in the presence of radical initializer such as 1,1'-azobiscyclohexanecarbonitrile (ABCN) in carbon tetrachloride (CCl$_4$). A Suzuki coupling with compound 3 and R$^1$B(OH)$_2$ or its ester or R$^1$BF$_3$$^+$F$^-$ produces compound 4. Other suitable reaction conditions or protocols may be used instead of the Suzuki reaction, such as Stille reaction conditions. The p-methoxybenzyl group (PMB) of compound 4 is removed to provide compound 5. Suitable reaction conditions for the removal of the PMB include, but are not limited to, treatment with a strong acid, such as trifluoroacetic acid. If the protecting group on the amino moiety of R group is also acid-sensitive such as Boc, then the amino group is re-protected with an urethane group such as Boc or Cbz to give compound 5. Under copper mediated reaction such as Cu(OAc)$_2$, aromatic group can be introduced via its boronic acid, R$^2$B(OH)$_2$ (Chan-Lam coupling) and removal of the protecting group on the amino moiety of R group affords the final compound 6. Alternatively, an alkyl group R$^2$ can be introduced by reacting compound 5 with alkylating agent such as R$^2$Br, followed by removing the protecting group of amine on R to produce the final compound 6.

In another aspect, compounds described herein are prepared as outlined in Scheme B.

Scheme B

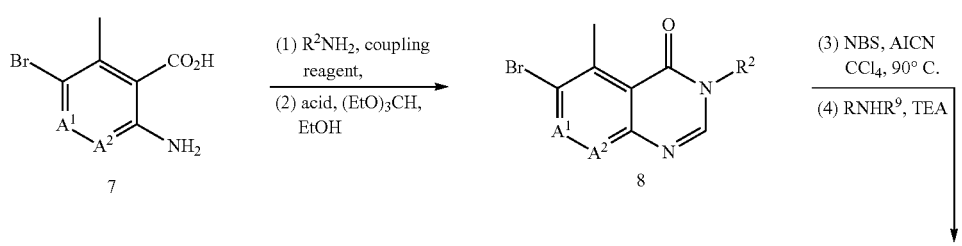

-continued

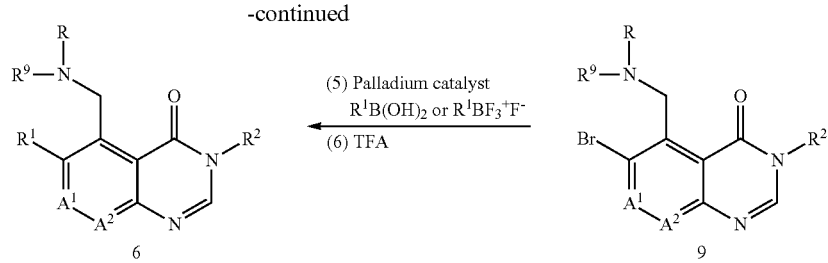

In one aspect Acid 7 is coupled with amine or aniline ($R^2NH_2$) in the presence of a coupling reagent such as, but not limited to, HATU, followed by treatment of orthoformate in the presence of an acid such as p-toluene sulfonic acid or acetic acid to give compound 8. Compound 8 is brominated with a suitable brominating agent and then reacted with an amine, $RR^9NH$, where R can be a protected alkylaminoalkyl group and $R^9$ can be hydrogen or an alkyl group to produce compound 9. In some embodiments, bromination is performed by refluxing compound 8 with N-bromosuccinimide (NBS) in the presence of radical initializer such as 1,1'-azobiscyclohexanecarbonitrile (ABCN) in carbon tetrachloride ($CCl_4$). A Suzuki coupling between compound 9 and $R^1B(OH)_2$ or its ester or $R^1BF_3^+F^-$ is followed by the removal of any protecting groups to produce compound 6. Other suitable reaction conditions or protocols may be used instead of the Suzuki reaction, such as Stille reaction conditions.

In some embodiments, Compounds of structural Formula (I), where $A^1$, $B^1$ and $B^2$ are CH and $A^2$ is N may be synthesized according to Scheme C.

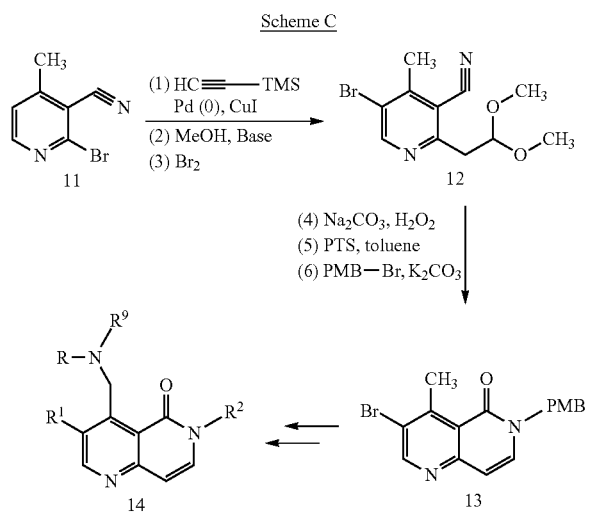

In some embodiments, the commercially available material 11 undergoes a Sonogashira coupling reaction followed by treatment of methanol in the presence of base, followed by bromination of the pyridine to yield the intermediate 12. Partial hydrolysis of cyano group to the carboxamide is achieved by use of hydrogen peroxide under basic reaction conditions, followed by subsequent treatment with para-toluene sulfonic acid (PTS) yields the ring closed product, that is then treated with para-methoxybenzylbromide under standard alkylating reaction conditions to provide compound 13. By using similar reaction conditions and transformations as outlined in Scheme A, compound 13 is transformed into compound 14.

In some embodiments, Compounds of structural Formula (I), where $A^1$ and $B^1$ are CH, $A^2$ is either N or CH and $B^2$ is N, are synthesized as outlined in Scheme D.

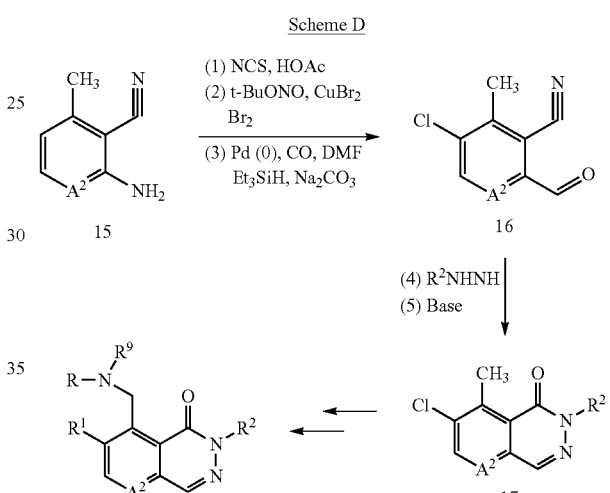

In some embodiments, commercially available starting material 15 undergoes a chlorination reaction with N-chlorosuccinimde (NCS), followed by a standard diazotization procedure or its variation to transfer the amino group to the corresponding bromide. In some embodiments, diazotization can transfer the amino group to hydroxyl group, which can be activated by forming a trifluoromethanesulfonyl group (OTf). Either bromo or OTf group is then converted to formyl group by use of palladium catalyzed carbon monoxide insertion to afford compound 16. Treatment of 16 with a hydrazine ($R^2NHNH_2$) yields a ring closure which is followed by the hydrolysis of C=NH functionality with a base, such as NaOH, to afford compound 17. Following similar reaction conditions and transformations described in Scheme B, compound 17 is converted to compound 18. In some embodiments, the cyano group (CN) of compound 15 can be replaced with a carboxylate such as $CO_2Me$, which in turn can form compound 17 directly upon treatment of $R^2NHNH_2$ from compound 16 (wherein CN is replaced with $CO_2Me$).

In some embodiments, compounds, wherein $R^b$ is not hydrogen, described herein are prepared as outlined in Scheme E:

Scheme E

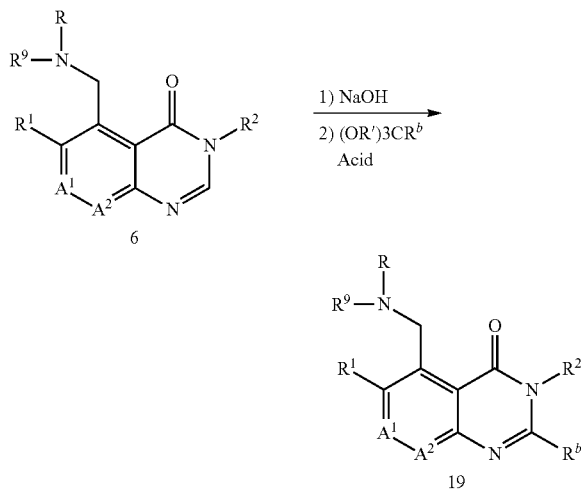

The ring of pyrimidine on compound 10 can be reopened by a base such as NaOH, and then re-closed by an orthoformate such as trimethyl orthoacetate to form 19.

In some embodiments, compounds described herein are synthesized as outlined in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. Typical alkylene groups include, but are not limited to, —$CH_2$—, —$CH_2CH_2$—, —$CH_2CH_2CH_2$—, —$CH_2CH_2CH_2CH_2$—, and the like. In some embodiments, an alkylene is —$CH_2$—.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

An "hydroxyalkyl" refers to an alkyl in which one hydrogen atom is replaced by a hydroxyl. In some embodiments, a hydroxyalkyl is a $C_1$-$C_4$hydroxyalkyl. Typical hydroxyalkyl groups include, but are not limited to, —$CH_2OH$, —$CH_2CH_2OH$, —$CH_2CH_2CH_2OH$, —$CH_2CH_2CH_2CH_2OH$, and the like.

An "aminoalkyl" refers to an alkyl in which one hydrogen atom is replaced by an amino. In some embodiments, aminoalkyl is a $C_1$-$C_4$aminoalkyl. Typical aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, and the like.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahyodronaphthyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a $C_1$-$C_6$fluoroalkyl.

The term"fluoroalkoxy" group refers to a (fluoroalkyl) O— group, where fluoroalkyl is as defined herein.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heterocycloalkyl also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, heterocycle, $C_1$-$C_4$alkyl, $C_1$-$C_4$fluoroalkyl, $C_1$-$C_4$fluoroalkoxy, —CN, —OR$^{17}$, —CO$_2$R$^{17}$, —C(=O)NR$^{17}$R$^{18}$, —NR$^{17}$R$^{18}$, —NR$^{17}$C(=O)NHR$^{18}$, —NR$^{17}$C(=O)R$^{18}$, —C(=NOR$^{17}$)R$^{18}$, —SR$^{17}$, —S(=O)(C$_1$-C$_4$alkyl), —SO$_2$(C$_1$-C$_4$alkyl), or —SO$_2$NR$^{17}$R$^{18}$. In some other embodiments, optional substituents are independently selected from halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (A), or a pharmaceutically acceptable salt thereof, and a co-agent, are both administered to a patient simultaneously in the form of a single entity or dosage. The term "non-fixed combination" means that the active ingredients, e.g. a compound of Formula (A), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds of Formula (A), or a pharmaceutically acceptable salt thereof, are used in the preparation of medicaments for the treatment of diseases or conditions in a mammal that would benefit from modulation of somatostatin activity. Methods for treating any of the diseases or conditions described herein in a mammal in need of such treatment, involves administration of pharmaceutical compositions that include at least one compound of Formula (A) or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (A), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (A), or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound of Formula (A), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound of Formula (A), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound of Formula (A), or a pharmaceutically acceptable salt thereof, is co-administered with a second therapeutic agent, wherein the compound of Formula (A), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (A), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

EXAMPLES

Abbreviations

ABCN: 1,1'-azobis(cyclohexanecarbonitrile);
DCM: dichloromethane;
EtOAc: ethyl acetate;
HATU: 1-[bis(dimethylamino)methylene]-1H-1,2,3-triazolo[4,5-b]pyridinium 3-oxid hexafluorophosphate;
NBS: N-bromosuccinimide:
NCS: N-chlorosuccinimide;
PTS: p-toluene sulfonic acid;
Pd (amphos)Cl$_2$: bis(di-tert-butyl(4dimethylaminophenyl)phosphine)dichloropalladium(II);
rt: room temperature;
SST: somatostatin;
SSTR: somatostatin receptor;
TEA: trimethylamine
hrs: hours;
hr: hour.

The following examples are provided for illustrative purposes only and not to limit the scope of the claims provided herein.

Synthesis of Compounds

Example 1: Preparation of Benzyl [(2S)-1-(methylamino)butan-2-yl]carbamate

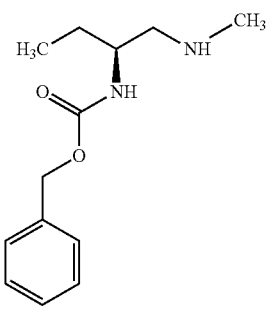 [SMILES: CC[C@@H](CNC)NC(=O)OCc1ccccc1]

Step 1, Preparation of benzyl [(2S)-1-hydroxybutan-2-yl]carbamate: to (2S)-2-aminobutan-1-ol (2.0 g, 22.5 mmol) in DCM (10 ml), Cbz-OSu (5 g, 20 mmol) was added dropwise. The mixture was then stirred at rt for 2 hrs, diluted with ethyl acetate (100 ml) and then washed with 4N HCl (10 ml), then 2N NaOH (10 ml), dried and concentrated to give a colorless oil as the desired product. MS (M+1)$^+$: 224.1.

Step 2: Preparation of benzyl {(2S)-1-[methyl(prop-2-en-1-yl)amino]butan-2-yl}carbamate To the oil from Step 1 in DCM (70 ml), Dess Martin periodinane (8.48 g, 20 mmol) was added slowly over 10 min. The slurry was stirred for another 1 hr after addition, the precipitates were filtered off. To the filtered solution cooled with ice-water bath, triethylamine (2.8 ml, 20 mmol) was added, followed by addition of N-allylmethylamine (1.45 g, 20 mmol), then NaBH(OAc)$_3$ (5.1 g, 20 mmol) in several portions. The mixture was stirred at rt for additional 1 hr, diluted with DCM (200 ml), then washed with water (200 ml), 4N NaOH (2×100 ml), dried, concentrated to produce the desired product (3.7 g). MS (M+1)$^+$: 277.2.

Step 3, Preparation of benzyl [(2S)-1-(methyl-amino)butan-2-yl]carbamate

To the oil from step in THF (60 ml), thiosalicylic acid (3.8 g, 20 mmol) was added, followed addition of 1,4-bis(diphenylphosphino)butane (426 mg, 1 mmol) and tris(dibenzylideneacetone)-dipalladium (0) (458 mg, 0.5 mmol). The reaction was stirred at rt for 30 min. it was concentrated, then diluted with ethyl acetate. The ethyl acetate layer was then washed with 6 N HCl (2×50 ml). The aqueous acid solution was then carefully neutralized to pH 9 by slow addition of $Na_2CO_3$ powders, then extracted with ethyl acetate. The ethyl acetate layer was then washed with 4N NaOH, water, dried and concentrated to yield 3.1 g of the desired product. MS (M+1)$^+$: 237.2.

The following compounds in the table were prepared using the above similar techniques with appropriate substitutions of reagents and substrates, where the acid extraction was not used if the amino protecting group was Boc, instead of direct column chromatography of the crude was performed using DCM/MeOH as eluents.

| Compound # | Structure | MS (M + H)$^+$ |
|---|---|---|
| 1-2 | 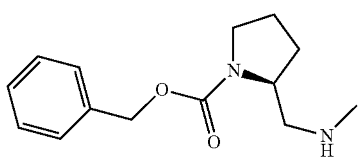 [SMILES: CNC[C@@H]1CCCN1C(=O)OCc1ccccc1] | 249.2 |
| 1-3 | 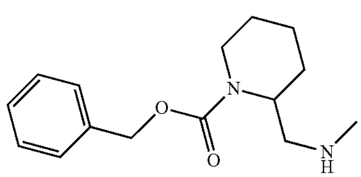 [SMILES: CNCC1CCCCN1C(=O)OCc1ccccc1] | 263.2 |
| 1-4 | 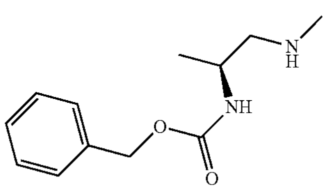 [SMILES: CNC[C@H](C)NC(=O)OCc1ccccc1] | 223.1 |
| 1-5 | 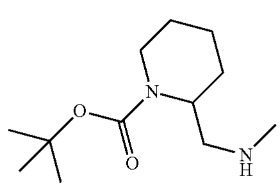 [SMILES: CNCC1CCCCN1C(=O)OC(C)(C)C] | 229.2 |
| 1-6 | 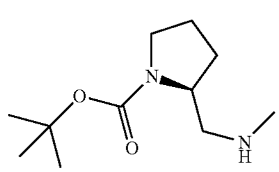 | 215.2 |

Example 2: Synthesis of 5-{[(2-amino-ethyl)-methyl-amino]-methyl}-6-(3,5-dimethyl-phenyl)-3-(3-hydroxy-phenyl)-3H-pyrido[2,3-d]pyrimidin-4-one

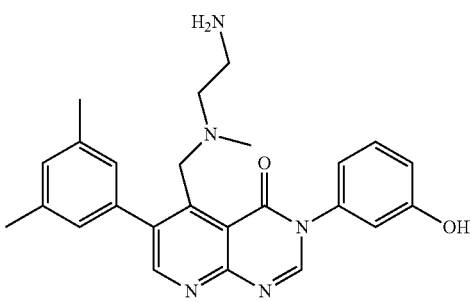 [SMILES: Cc1cc(C)cc(-c2cnc3ncn(-c4cccc(O)c4)c(=O)c3c2CN(C)CCN)c1]

Step 1, Preparation of 2-amino-N-(3-benzyloxy-phenyl)-5-bromo-4-methylnicotinamide To a dry DMF solution (30 ml) of 2-amino-5-bromo-4-methyl-nicotinic acid (2.0 g, 8.7 mmol), 3-benzoxylaniline (2.6 g, 13.0 mmol) and TEA (3.6 ml, 3.0 eq), HATU (5.0 g, 1.5 eq) was added. The slurry was stirred at rt for 2 days, then diluted with 1 N NaOH (50 ml) and extracted with ethyl acetate (100 ml). The ethyl acetate layer was separated, dried, concentrated. The crude was purified by silica gel chromatography eluted with hexane/ethyl acetate to yield the desired product (4.5 g) was obtained as an off white solid. MS (M+H)$^+$: 412.1.

Step 2, Preparation of 3-(3-benzyloxy-phenyl)-6-bromo-5-methyl-3H-pyrido[2,3-d]pyrimidin-4-one A mixture of 2-amino-N-(3-benzyloxy-phenyl)-5-bromo-4-methylnicotinamide from Step 1-1 (4.5 g, 11 mmol) and triethyl orthoformate (13 ml, 80 mmol), PTS.H$_2$O (160 mg, 0.84 mmol) were heated at 105° C. for 17 hrs, then cooled to rt, concentrated and then purified by silica gel column chromatography eluted with hexane/ethyl acetate to afford the product (2.9 g). MS (M+H)$^+$: 422.1.

Step 3, Preparation of 3-(3-benzyloxy-phenyl)-6-bromo-5-bromomethyl-3H-pyrido[2,3-d]pyrimidin-4-one A mixture of 3-(3-benzyloxy-phenyl)-6-bromo-5-methyl-3H-pyrido[2,3-d]pyrimidin-4-one from Step 1-2 (845.0 mg, 2.0 mmol) and NBS (534.0 mg, 3.0 mmol) and ABCN (97 mg, 0.4 mmol) in CCl$_4$ (15 ml) were refluxed for 2 hrs. The crude is cooled to rt and used for next step without further purification. MS (M+H)$^+$: 501.0.

Step 4, Preparation of (2-{[3-(3-benzyloxy-phenyl)-6-bromo-4-oxo-3,4-dihydro-pyrido[2,3-d]pyrimidin-5-ylmethyl]-amino}-ethyl)-carbamic acid tert-butyl ester Above solution from Step 1-3 was diluted with dioxane (15 ml), (2-methyl-amino-ethyl)-carbamic acid tert-butyl ester (640 mg, 3.7 mmol) and TEA (0.55 ml, 4 mmol) were added. The mixture was stirred at rt for 17 hrs. The mixture was then concentrated and purified by silica gel chromatography eluted with DCM/MeOH to produce the desired product (450 mg). (M+H)+: 594.1.

Step 5, preparation of (2-{[3-(3-benzyloxy-phenyl)-6-(3,5-dimethyl-phenyl)-4-oxo-3,4-dihydro-pyrido[2,3-d]pyrimidin-5-ylmethyl]-methyl-amino}-ethyl)-carbamic Acid tert-butyl Ester To (2-{[3-(3-benzyloxy-phenyl)-6-bromo-4-oxo-3,4-dihydro-pyrido[2,3-d]pyrimidin-5-ylmethyl]-methyl-amino}-ethyl)-carbamic acid tert-butyl ester from Step 1-4 (450 mg, 0.76 mmol) in dioxane/water (3 ml/0.3 ml), 3,5-dimethyl-phenylboronic acid (150 mg, 1.0 mmol), $K_2CO_3$ (250 mg, 1.8 mmol) were added. The mixture was bubbled with $N_2$ gas for 10 min, then Pd (amphos)$Cl_2$(40 mg, 0.06 mmol), then sealed and heated at 100° C. for 3 hrs. The crude was concentrated and purified on silica gel using DCM/EtOAc to give the desired product (500 mg). (M+H)+: 620.4.

Step 6, Preparation of (2-{[6-(3,5-dimethyl-phenyl)-3-(3-hydroxy-phenyl)-4-oxo-3,4-dihydro-pyrido[2,3-d]pyrimidin-5-ylmethyl]-methyl-amino}-ethyl)-carbamic Acid tert-butyl Ester The above product from Step 1-5 (500 mg) was refluxed with Pd/C (10%, 30 mg) and ammonium formate (400 mg, 6.3 mmol) for 1 hr. The mixture was filtered and concentrated, then purified by silica gel column chromatography eluted with DCM/EtOAc to afford the desired product (32 mg). (M+H)+: 530.3

Step 7, Preparation of 5-{[(2-amino-ethyl)-methyl-amino]-methyl}-6-(3,5-dimethyl-phenyl)-3-(3-hydroxy-phenyl)-3H-pyrido[2,3-d]pyrimidin-4-one To the above oil from Step 6, 4N HCl in dioxane (2 ml) was added. The mixture was stirred at rt for 30 min. then concentrated to yield the desired product (28 mg) as HCl salt (compound A-1). (M+H)+: 430.3.

Example 3: Synthesis of 5-{[(2-Amino-ethyl)-ethyl-amino]-methyl}-6-(3,5-dimethyl-phenyl)-3-(3-hydroxy-phenyl)-3H-pyrido[2,3-d]pyrimidin-4-one

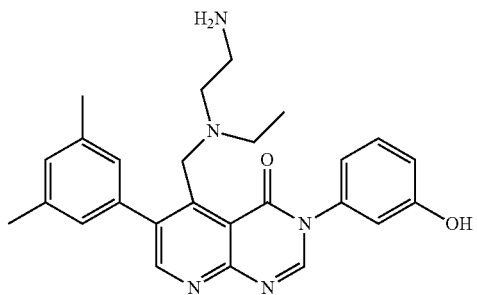 [SMILES: CCN(CCN)Cc1c(-c2cc(C)cc(C)c2)cnc2ncn(-c3cccc(O)c3)c(=O)c12]

The title compound (A-2) was prepared similarly according to the procedures outlined in Example 2.

Example 4: Synthesis of 6-(3,5-dimethyl-phenyl)-3-(3-hydroxy-phenyl)-5-[(methyl-piperidin-2-ylmethyl-amino)-methyl]-3H-pyrido[2,3-d]pyrimidin-4-one

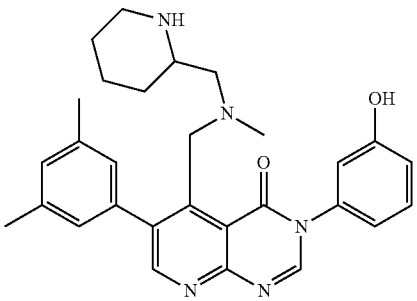 [SMILES: Cc1cc(C)cc(-c2cnc3ncn(-c4cccc(O)c4)c(=O)c3c2CN(C)CC2CCCCN2)c1]

Step 1, preparation of 2-amino-5-bromo-N-{3-[(4-methoxybenzyl)oxy]phenyl}-4-methylpyridine-3-carboxamide To a dry DMF solution (200 ml) of 2-amino-5-bromo-4-methyl-nicotinic acid (11.6 g, 50 mmol), 3-(4-methoxybenzyl)aniline (11.5 g, 50 mmol) and TEA (7.0 ml, 50 mmol), HATU (20.9 g, 55 mmol) was added. The slurry was stirred at 35° C. for 24 hrs, then diluted with water (100 ml) and ethyl acetate (200 ml). The ethyl acetate layer was separated, dried. The product precipitated out gradually upon standing and was filtered and washed with tert-butyl methyl ether, dried. The mother liquor was partially concentrated to yield the second crop. Total 14.2 g of the product was obtained as an off white solid. MS (M+H)+: 442.1.

Step 2, preparation of 6-bromo-3-{3-[(4-methoxybenzyl)oxy]phenyl}-5-methylpyrido[2,3-d]pyrimidin-4(3H)-one A mixture of 2-amino-5-bromo-N-{3-[(4-methoxybenzyl)oxy]phenyl}-4-methylpyridine-3-carboxamide (4.4 g, 10 mmol) and triethyl orthoformate (16.6 ml, 100 mmol), and acetic acid (12 ml, 200 mmol) were refluxed for 24 hrs, then cooled to rt which led to precipitation. The precipitates were filtered, washed with t-butyl methyl ether and dried to afford the product (4.0 g). MS (M+H)+: 452.1.

Step 3, Preparation of 6-bromo-5-(bromomethyl)-3-{3-[(4-methoxybenzyl)oxy]phenyl}pyrido[2,3-d]pyrimidin-4(3H)-one A mixture of 6-bromo-3-{3-[(4-methoxybenzyl)oxy]phenyl}-5-methylpyrido[2,3-d]pyrimidin-4(3H)-one from Step 2-2 (200 mg, 0.44 mmol) and NBS (126 mg, 0.71 mmol) and ABCN (24 mg, 0.1 mmol) in $CCl_4$ (6 ml) were refluxed for 1 hr. The crude is cooled to rt and used for next step without further purification. MS (M+H)+: 530.0.

Step 4, Preparation of 2-[({6-bromo-3-[3-(4-methoxy-benzyloxy)-phenyl]-4-oxo-3,4-dihydro-pyrido[2,3-d]pyrimidin-5-ylmethyl]-amino)-methyl}-piperidine-1-carboxylic Acid tert-butyl Ester To the above solution from Step 3, tert-butyl 2-(aminomethyl)piperidine-1-carboxylate (214 mg, 1 mmol) and TEA (0.14 ml, 1 mmol) were added. The mixture was stirred at rt for 17 hrs. The mixture was then concentrated and purified by silica gel chromatography eluted with a combination of DCM and MeOH to produce the desired product (110 mg). (M+H)+: 664.2.

Step 5, Preparation of 2-[({6-bromo-3-[3-(4-methoxy-benzyloxy)-phenyl]-4-oxo-3,4-dihydro-pyrido[2,3-d]pyrimidin-5-ylmethyl}-methyl-amino)-methyl]-piperidine-1-carboxylic Acid tert-butyl Ester To the oil from Step 4 in DCM (4 ml), formaldehyde (0.08 ml, 1 mmol) was added, followed by addition of NaBH(OAc)₃ (424 mg, 2 mmol). The mixture was stirred at rt for 2 hrs, then diluted with ethyl acetate. The organic layer was washed with water, concentrated to yield the desired product (110 mg). (M+H)+: 678.2.

Step 6, Preparation of 2-[({6-(3,5-dimethyl-phenyl)-3-[3-(4-methoxy-benzyloxy)-phenyl]-4-oxo-3,4-dihydro-pyrido[2,3-d]pyrimidin-5-ylmethyl}-methyl-amino)-methyl]-piperidine-1-carboxylic Acid tert-butyl Ester To 2-[({6-bromo-3-[3-(4-methoxy-benzyloxy)-phenyl]-4-oxo-3,4-dihydro-pyrido[2,3-d]pyrimidin-5-ylmethyl}-methyl-amino)-methyl]-piperidine-1-carboxylic acid tert-butyl ester from Step 5 (110 mg, 0.16 mmol) in dioxane/water (2 ml/0.2 ml), Pd (amphos)Cl₂ (20 mg, 0.03 mmol), 3,5-dimethylphenylboronic acid (75 mg, 0.5 mmol), K₂CO₃ (91 mg, 0.65 mmol) were added. The mixture was bubbled with N₂ gas for 10 min and then sealed and heated at 95° C. for 8 hrs. The crude was concentrated and purified on silica gel using DCM/MeOH to give the desired product (46 mg). (M+H)+: 704.5.

Step 7, Preparation of 6-(3,5-dimethyl-phenyl)-3-(3-hydroxy-phenyl)-5-[(methyl-piperidin-2-ylmethyl-amino)-methyl]-3H-pyrido[2,3-d]pyrimidin-4-one The above product from Step 6 (46 mg) was stirred with 50% TFA in DCM (2 ml) for 17 hrs, and then concentrated partially. Tert-butyl methyl ether (10 ml) was added, resulted in precipitation. The precipitates were filtered and dried to afford the desired product (12 mg) as compound A-13. (M+H)+: 484.6.

The following compounds were prepared similarly to Example 4:

| Compound # | MS (M + H)+ |
|---|---|
| A-4 | 458.2 |
| A-5 | 506.3 |
| A-7 | 444.5 |
| A-12 | 486.5 |
| A-68 | 530.4 |
| A-10 | 442.6 |
| A-11 | 456.6 |
| A-21 | 470.6 |
| A-23 | 486.3 |
| A-24 | 490.3 |
| A-22 | 498.4 |
| A-69 | 506.4 |
| A-13 | 484.4 |
| A-25 | 488.3 |
| A-26 | 488.3 |
| A-70 | 502.3 |

Example 5: Synthesis of (2S)-6-(3,5-dimethyl-phenyl)-3-(3-hydroxy-phenyl)-5-[(methyl-pyrrolidin-2-ylmethyl-amino)-methyl]-3H-pyrido[2,3-d]pyrimidin-4-one

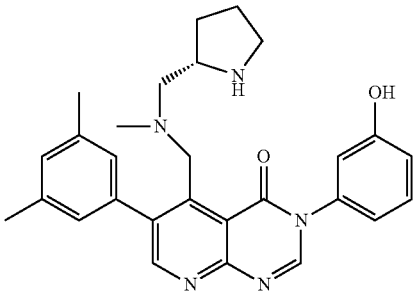 [SMILES: Cc1cc(C)cc(-c2cnc3ncn(-c4cccc(O)c4)c(=O)c3c2CN(C)C[C@@H]2CCCN2)c1]

Step 1, Preparation of (2S)-2-[({6-bromo-3-[3-(4-methoxy-benzyloxy)-phenyl]-4-oxo-3,4-dihydro-pyrido[2,3-d]pyrimidin-5-ylmethyl}-amino)-methyl]-pyrrolidine-1-carboxylic Acid tert-butyl Ester To 6-bromo-5-(bromomethyl)-3-{3-[(4-methoxybenzyl)oxy]phenyl}pyrido[2,3-d]pyrimidin-4(3H)-one (Step 3 of Example 4, 232 mg, 0.44 mmol), (S)-2-aminomethyl-pyrrolidine-1-carboxylic acid tert-butyl ester (200 mg, 1.0 mmol) and TEA (0.15 ml, 1.1 mmol) were added. The mixture was stirred at rt for 17 hrs. The mixture was then concentrated and purified by silica gel chromatography eluted with a combination of DCM and MeOH and to produce the desired product (150 mg). MS (M+H)+: 651.2.

Step 2, Preparation of (2S)-2-[({6-bromo-3-[3-(4-methoxy-benzyloxy)-phenyl]-4-oxo-3,4-dihydro-pyrido[2,3-d]pyrimidin-5-ylmethyl}-methyl-amino)-methyl]-pyrrolidine-1-carboxylic Acid tert-butyl Ester To the oil from Step 1 in DCM (4 ml), formaldehyde solution in water (37%, 0.081 ml, 1.0 mmol) was added, followed by addition of NaBH(OAc)₃ (420 mg, 2.0 mmol). The mixture was stirred at rt for 1 hr, then diluted with ethyl acetate. The organic layer was washed with water, concentrated to yield the desired product (170 mg). MS (M+H)+: 664.2.

Step 3, Preparation of (2S)-2-[({6-3,5-dimethyl-phenyl)-3-[3-(4-methoxy-benzyloxy)-phenyl]-4-oxo-3,4-dihydro-pyrido[2,3-d]pyrimidin-5-ylmethyl}-methyl-amino)-methyl]-pyrrolidine-1-carboxylic Acid tert-butyl Ester To the material from Step 2 (170 mg, 0.26 mmol) in dioxane/water (2 ml/0.2 ml), Pd (amphos)Cl₂ (7.1 mg, 0.01 mmol), 3,5-dimethylphenylboronic acid (75 mg, 0.5 mmol), K₂CO₃ (90 mg, 0.65 mmol) were added. The mixture was bubbled with N₂ gas for 10 min and then sealed and heated at 90° C. for 8 hrs. The crude was concentrated and purified on silica gel using DCM/MeOH to give the desired product (37 mg). MS (M+H)+: 690.5.

Step 4 Preparation of (2S)-6-(3,5-dimethyl-phenyl)-3-(3-hydroxy-phenyl)-5-[(methyl-pyrrolidin-2-ylmethyl-amino)-methyl]-3H-pyrido[2,3-d]pyrimidin-4-one The above product from Step 3 (37 mg) was stirred with 50% TFA in DCM (2 ml) for 17 hrs, and then concentrated partially. Tert-butyl methyl ether (10 ml) was added, resulted in precipitation. The precipitates were filtered and dried to afford the desired product (9 mg) as compound A-17. MS (M+H)+: 470.5.

Example 6: Synthesis of (2S)-6-(3-chloro-5-methyl-phenyl)-3-(3-hydroxy-phenyl)-5-[(methyl-pyrrolidin-2-ylmethyl-amino)-methyl]-3H-pyrido[2,3-d]pyrimidin-4-one

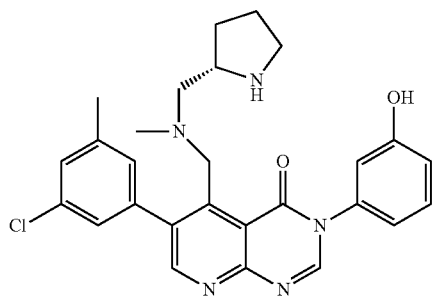 [SMILES: Cc1cc(Cl)cc(-c2cnc3ncn(-c4cccc(O)c4)c(=O)c3c2CN(C)C[C@@H]2CCCN2)c1]

Step 1, Preparation of (2S)-2-[({6-bromo-3-[3-(4-methoxy-benzyloxy)-phenyl]-4-oxo-3,4-dihydro-pyrido[2,3-d]pyrimidin-5-ylmethyl}-methyl-amino)-methyl]-pyrrolidine-1-carboxylic Acid Benzyl Ester (1.45 g)

Was accomplished similarly according to Step 4 of Example 4 by use of (S)-2-methylaminomethyl-pyrrolidine-1-carboxylic acid benzyl ester (Compound 1-2, 1.5 g) and 6-bromo-5-(bromomethyl)-3-{3-[(4-methoxybenzyl)oxy]phenyl}pyrido[2,3-d]pyrimidin-4(3H)-one (1.80 g). MS (M+H)+: 698.4.

Step 2, Preparation of (2S)-2-[({6-(3-chloro-5-methyl-phenyl)-3-[3-(4-methoxy-benzyloxy)-phenyl]-4-oxo-3,4-dihydro-pyrido[2,3-d]pyrimidin-5-ylmethyl}-methyl-amino)-methyl]-pyrrolidine-1-carboxylic Acid Benzyl Ester Was conducted similarly according to Step 6 of Example 4 by use of 3-chloro-5-methylphenyl boronic acid (140 mg) and (2S)-2-({[6-bromo-3-(3-hydroxy-phenyl)-4-oxo-3,4-dihydro-pyrido[2,3-d]pyrimidin-5-ylmethyl]-methyl-amino}-methyl)-pyrrolidine-1-carboxylic acid benzyl ester (280 mg) to produce the titled compound (160 mg). MS (M+H)+: 744.5.

Step 3, Preparation of (2S)-6-(3-chloro-5-methyl-phenyl)-3-(3-hydroxy-phenyl)-5-[(methyl-pyrrolidin-2-ylmethyl-amino)-methyl]-3H-pyrido[2,3-d]pyrimidin-4-one (2S)-2-[({6-(3-chloro-5-methyl-phenyl)-3-[3-(4-methoxy-benzyloxy)-phenyl]-4-oxo-3,4-dihydro-pyrido[2,3-d]pyrimidin-5-ylmethyl}-methyl-amino)-methyl]-pyrrolidine-1-carboxylic acid benzyl ester (160 mg) was heated in a mixture of TFA (5 ml) and thioanisole (0.5 ml) at 55° C. for 2 hrs, then concentrated and precipitated with hexane and then further purified by reverse phase column (15 g, Isco) eluted with water and acetonitrile which contain 0.1% TFA to yield the desired product (33.5 mg) as compound A-30. MS (M+H)+: 490.4.

The following compounds were prepared similarly to Example 5 or Example 6.

| Compound # | MS (M + H)+ |
| --- | --- |
| A-16 | 470.5 |
| A-19 | 486.7 |
| A-15 | 484.5 |
| A-14 | 484.5 |
| A-18 | 456.5 |
| A-8 | 444.4 |
| A-9 | 458.4 |
| A-36 | 474.4 |
| A-34 | 472.3 |
| A-37 | 486.3 |
| A-38 | 506.5 |
| A-35 | 494.4 |
| A-32 | 486.2 |
| A-28 | 522.5 |
| A-27 | 502.2 |
| A-29 | 504.2 |

Example 7: Synthesis of (2S)-6-(3-chloro-5-methyl-phenyl)-3-(3-fluoro-5-hydroxy-phenyl)-5-[(methyl-pyrrolidin-2-ylmethyl-amino)-methyl]-3H-pyrido[2,3-d]pyrimidin-4-one

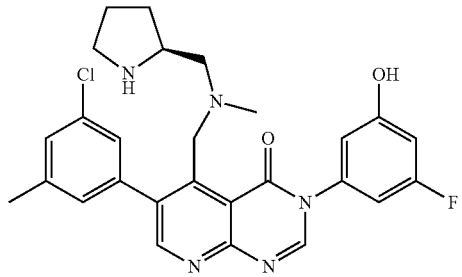 [SMILES: Cc1cc(Cl)cc(-c2cnc3ncn(-c4cc(O)cc(F)c4)c(=O)c3c2CN(C)C[C@@H]2CCCN2)c1]

Step 1, Preparation of 2-amino-5-bromo-N-(4-methoxybenzyl)-4-methylnicotinamide 2-amino-5-bromo-4-methylnicotinic acid (4.60 g, 20 mmol) and HATU (9.2 g, 24 mmol) were dissolved into DMF (60 ml) under the ice-water bath, then TEA (4.2 ml, 30 mmol) was added to above solution and the solution became clearly immediately. Then 4-methoxybenzylamine (3.9 ml, 30 mmol) was added in one portion. The reaction mixture was stirred for 4 hours at room temperature. LCMS showed the completion of the reaction. Thus it was dumped into vigorously stirred water (1000 ml), which resulted in precipitation and the solid was then collected by filtration and dried to give the desired product (5.75 g). MS (M+H)+: 350.2.

Step 2, Preparation of the 6-bromo-3-(4-methoxybenzyl)-5-methylpyrido[2,3-d]pyrimidin-4(3H)-one To 2-amino-5-bromo-N-(4-methoxybenzyl)-4-methylnicotinamide (1.14 g, 3.3 mmol) in a mixture of EtOH (20 ml)

and triethoxyl orthformate (20 ml), p-toluenesulfonic acid (95 mg, 0.5 mmol) was added. The reaction solution was heated to reflux for overnight, then cooled to room temperature. The corresponding precipitates were collected and dried to provide the desired products (0.81 g). MS (M+H)$^+$: 360.2

Step 3, Preparation of 6-bromo-5-bromomethyl-3-(4-methoxy-benzyl)-3H-pyrido[2,3-d]pyrimidin-4-one To 6-bromo-3-(4-methoxybenzyl)-5-methylpyrido[2,3-d]pyrimidin-4(3H)-one (360 mg, 1 mmol), NBS (260 mg, 1.5 mmol), ABCN (250 mg, 1 mmol) were added into CCl$_4$ (5 ml), and the reaction was heated to reflux. LCMS monitored the progress of the reaction. It showed the reaction was completed in 2 hrs. MS (M+H)$^+$: 440.1.

Step 4, Preparation of (2S)-({[6-bromo-3-(4-methoxy-benzyl)-4-oxo-3,4-dihydro-pyrido[2,3-d]pyrimidin-5-ylmethyl]-methyl-amino}-methyl)-pyrrolidine-1-carboxylic Acid tert-butyl Ester The crude from Step 3 was diluted by DCM (10 ml), then, TEA (0.45 ml, 3 mmol) was added and followed by addition of 2-(S)-methylaminomethyl-pyrrolidine-1-carboxylic acid tert-butyl ester (Example 1-6, 214 mg, 1 mmol). The reaction mixture was stirred for overnight, and it was concentrated and directly loaded to silica gel for chromatography which was eluted with a mixture of DCM with MeOH to give the desired compounds (440 mg). MS (M+H)$^+$: 572.5.

Step 5, Preparation of (2S)-2-({[6-(3-chloro-5-methyl-phenyl)-3-(4-methoxy-benzyl)-4-oxo-3,4-dihydro-pyrido[2,3-d]pyrimidin-5-ylmethyl]-methyl-amino}-methyl)-pyrrolidine-1-carboxylic Acid tert-butyl Ester (S)-({[6-bromo-3-(4-methoxy-benzyl)-4-oxo-3,4-dihydro-pyrido[2,3-d]pyrimidin-5-ylmethyl]-methyl-amino}-methyl)-pyrrolidine-1-carboxylic acid tert-butyl ester (1.2 g, 2.1 mmol), tetra-kis(triphenylphosphine)-palladium (122 mg, 0.11 mmol), potassium triphosphate (1.5 g, 6 mmol), and 3-chloro-5-methylphenylboronic acid (535 mg, 3.0 mmol) were mixed into a mixture of dioxane (30 ml) and water (3 ml), then the reaction mixture was bubbled with N$_2$ for 10 min, then sealed and heated to 50° C. for 5 hrs. After cooled to rt, the crude was loaded on silica gel directly and purified using DCM and MeOH as eluents to offer the desired product (500 mg). (M+H)$^+$: 618.2.

Step 6, Preparation of (2S)-2-({[6-(3-chloro-5-methyl-phenyl)-4-oxo-3,4-dihydro-pyrido[2,3-d]pyrimidin-5-ylmethyl]-methyl-amino}-methyl)-pyrrolidine-1-carboxylic Acid tert-butyl Ester (S)-2-({[6-(3-chloro-5-methyl-phenyl)-3-(4-methoxy-benzyl)-4-oxo-3,4-dihydro-pyrido[2,3-d]pyrimidin-5-ylmethyl]-methyl-amino}-methyl)-pyrrolidine-1-carboxylic acid tert-butyl ester (500 mg, 0.8 mmol) was dissolved into TFA (5 ml) and heated to 60° C. for 4 hrs, then concentrated, the residue was redissolved into DCM (10 ml), then TEA (0.42 ml, 3 mmol) and Boc$_2$O (218 mg, 1 mmol) were added to the above solution, the reaction mixture was stirred for 30 min, and concentrated. The residue was loaded into the C$_{18}$ reverse phase column (50 g, Isco) and eluted with water and acetonitrile containing 0.1% TFA. The fractions with desired products were collected and concentrated to provide desired compound (300 mg). MS (M+H)$^+$: 498.1.

Step 7, Preparation of (2S)-6-(3-chloro-5-methyl-phenyl)-3-(3-fluoro-5-hydroxy-phenyl)-5-[(methyl-pyrrolidin-2-ylmethyl-amino)-methyl]-3H-pyrido[2,3-d]pyrimidin-4-one (2S)-2-({[6-(3-chloro-5-methyl-phenyl)-4-oxo-3,4-dihydro-pyrido[2,3-d]pyrimidin-5-ylmethyl]-methyl-amino}-methyl)-pyrrolidine-1-carboxylic acid tert-butyl ester (280 mg, 0.56 mmol), Cu(OAc)$_2$ (200 mg, 1.2 mmol), 3-fluoro-5-hydroxy-phenylboronic acid (200 mg, 1.28 mmol), pyridine (0.3 ml, 3.7 mmol) were mixed into DCM (28 ml), then the mixture was stirred for 8 hrs at rt and quenched with acetic acid (1 ml). The resulting solution was concentrated and the residue was loaded into the C$_{18}$ reverse phase column (50 g, Isco) and eluted with water and acetonitrile which contains 0.1% TFA, the fractions with desired product were collected and concentrated to an oil. The above oil was stirred in 50% TFA in DCM (2 ml) for 0.5 hr and concentrated. The residue was loaded into the C$_{18}$ column (50 g, Isco) and eluted with water and acetonitrile which contains 0.1% TFA. The fractions with desired product were collected and concentrated to provide the desired compound A-47 (104 mg). MS (M+H)$^+$: 508.0.

The following compounds were prepared similarly according to the procedures outlined for preparation of Example 7:

| Compound # | MS (M + H)$^+$ |
|---|---|
| A-33 | 484.3 |
| A-42 | 479.3 |
| A-43 | 497.3 |
| A-40 | 484.3 |
| A-41 | 470.3 |
| A-43 | 511.3 |
| A-45 | 488.2 |
| A-44 | 484.3 |
| A-31 | 517.2 |
| A-54 | 508.3 |
| A-48 | 558.2 |
| A-49 | 524.2 |
| A-50 | 535.2 |
| A-52 | 574.2 |
| A-46 | 497.2 |
| A-61 | 458.3 |
| A-3 | 481.3 |
| A-65 | 546.2 |
| A-62 | 476.3 |
| A-66 | 496.2 |
| A-64 | 523.2 |
| A-63 | 546.2 |
| A-53 | 508.2 |
| A-51 | 535.2 |
| A-71 | 515.5 |

Example 8: Synthesis of (2S)-6-(3-chloro-5-methyl-phenyl)-3-(3-hydroxy-phenyl)-2-isopropyl-5-[(methyl-pyrrolidin-2-ylmethyl-amino)-methyl]-3H-quinazolin-4-one

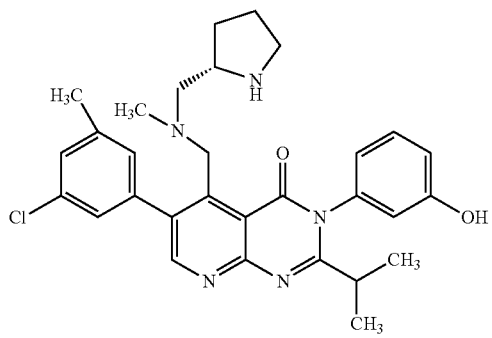 [SMILES: Cc1cc(Cl)cc(-c2cnc3nc(C(C)C)n(-c4cccc(O)c4)c(=O)c3c2CN(C)C[C@@H]2CCCN2)c1]

Step 1, Preparation of (2S)-2-[({2-amino-5-(3-chloro-5-methyl-phenyl)-3-[3-(4-methoxy-benzyloxy)-phenylcarbamoyl]-pyridin-4-ylmethyl}-methyl-amino)-methyl]-pyrrolidine-1-carboxylic Acid Benzyl Ester A mixture of (2S)-2-[({6-(3-chloro-5-methyl-phenyl)-3-[3-(4-methoxy-benzyloxy)-phenyl]-4-oxo-3,4-dihydro-pyrido[2,3-d]pyrimidin-5-ylmethyl}-methyl-amino)-methyl]-pyrrolidine-1-carboxylic acid benzyl ester (350 mg, 0.47 mmol), prepared from Step 2 of Example 6 and NaOH (0.4 N, 5 ml) was stirred at 85° C. in dioxane (6 ml) for 6 hr. The crude was extracted with ethyl acetate, dried and concentrated to give an oil (260 mg). MS (M+H)+ 734.3.

Step 2, Preparation of (2S)-6-(3-chloro-5-methyl-phenyl)-3-(3-hydroxy-phenyl)-2-isopropyl-5-[(methyl-pyrrolidin-2-ylmethyl-amino)-methyl]-3H-quinazolin-4-one (2S)-2-[({2-amino-5-(3-chloro-5-methyl-phenyl)-3-[3-(4-methoxy-benzyloxy)-phenylcarbamoyl]-pyridin-4-ylmethyl}-methyl-amino)-methyl]-pyrrolidine-1-carboxylic acid benzyl ester (18 mg, 0.025 mmol) was heated with triisopropyl orthoformate (0.5 ml) in ethanol (0.7 ml) in presence of PTS (2 mg) at 90° C. for 15 hrs. The crude was concentrated and purified by reverse phase C18 column chromatography eluted with water and acetonitrile containing 0.1% of TFA to afford the desired ring closure product (11 mg). MS (M+H)+: 787.4. It was then heated in TFA (1 ml) in the presence of thioanisole (0.2 ml) for 1 hr at 60° C. The crude was concentrated and purified by reverse phase $C_{18}$ column chromatography eluted with water and acetonitrile containing 0.1% of TFA to yield the desired compound A-58 (3 mg). MS (M+H)+: 532.2.

The following compounds were synthesized according to the procedures for preparation of Example 8.

| Compound # | MS (M + H)+ |
|---|---|
| A-56 | 504.2 |
| A-57 | 518.2 |
| A-55 | 502.3 |
| A-59 | 522.3 |
| A-60 | 531.2 |
| A-67 | 496.5 |

Example 9: SSTR Assays

Cell Culture

Chinese hamster ovary (CHO) cells stably expressing one of the six human or rodent somatostatin receptor subtypes are grown to 85-100% confluence on standard tissue culture dishes in F12-Ham's growth media (Hyclone) with following additives: 10% donor calf serum (Hyclone), 200 U/mL penicillin (Hyclone), 200 µg/mL streptomycin (Hyclone), 20 mM HEPES (Hyclone), 200 µg/mL hygromycin Hyclone.

Functional Assay Agonists

General overview: All SSTR subtypes are $G_i$ coupled G-protein coupled receptors (GPCRs) that lead to decreases in intracellular cyclic AMP (cAMP) when activated by an agonist. Therefore, measurement of intracellular cAMP levels can be used to assess whether compounds of the invention are agonists of SSTR subtypes (John Kelly, Troy Stevens, W. Joseph Thompson, and Roland Seifert, *Current Protocols in Pharmacology*, 2005, 2.2.1-2.2). One example of an intracellular cAMP assay is described below.

cAMP Assay Protocol for SSTR2a Agonists:

Four days prior to the assay, 5000 Chinese hamster ovary (CHO) cells stably expressing the human somatostatin receptor subtype 2a are plated in each well of a 96-well tissue culture plate (Nest Biotech Cell, flat bottom with low evaporation tissue culture treated; Polystyrene; Non-Pyrogenic) in F12-Ham's media (100 µL/well) supplemented with 200 µg/mL of hygromycin. Incubate at 37 C, 5% $CO_2$, 95% humidity for four days. The cells should reach full confluence. On the day of the assay, various dilutions of the compounds of the invention are prepared in assay buffer (HRTF cAMP kit, Cisbio) in the presence of 1.6 µM NKH-477 (a water-soluble forskolin derivative) and 50 µL of the dilutions are added to the cultured cells and incubated for 20 minutes at 37° C. (the final concentration of the compounds of the invention are typically 0-10,000 nM). 50 µL of lysis buffer (HRTF cAMP kit, Cisbio) is added to each well and incubated at room temperature for 30 minutes, after which 150 µL assay buffer is added to each well. In a 384-well plate (Grenier, 784-080), 10 µL of assay mixture is added to 10 µL of developing mixture, containing cAMP detection and visualization antibodies are added and the assay is allowed incubate for 1-24 hours at room temperature. The intracellular cAMP concentrations are then measured using a commercially available detection kit (for example, the cAMP HTRF kit, Cisbio). The measured intracellular cAMP concentrations are plotted vs. the concentration of the compounds of the invention and the $EC_{50}$ of the compounds are calculated using standard methods.

Illustrative biological activities are described in the following table. The potencies are divided into the three criteria: + means that $EC_{50}$ is between 100 nM and 10,000 nM; ++ means that $EC_{50}$ is below 100 nM; – means $EC_{50}$ is >10,000 nM, NT means not tested.

| Cmpd # | SSTR1 | SSTR2a | SSTR3 | SSTR4 | SSTR5 |
|---|---|---|---|---|---|
| A-1 | − | ++ | + | ++ | − |
| A-2 | − | ++ | + | ++ | + |
| A-3 | − | ++ | + | ++ | NT |
| A-4 | + | ++ | + | ++ | + |
| A-5 | NT | + | + | ++ | − |
| A-6 | NT | + | NT | + | − |
| A-7 | NT | + | + | ++ | NT |
| A-8 | NT | ++ | + | ++ | − |
| A-9 | + | ++ | ++ | ++ | NT |
| A-10 | NT | − | − | + | NT |
| A-11 | + | − | NT | ++ | NT |
| A-12 | NT | + | + | ++ | + |
| A-13 | + | ++ | ++ | ++ | − |
| A-14 | − | + | ++ | ++ | − |
| A-15 | + | ++ | ++ | ++ | + |
| A-16 | − | ++ | ++ | ++ | − |
| A-17 | + | ++ | ++ | ++ | NT |
| A-18 | + | ++ | + | ++ | NT |
| A-19 | NT | + | ++ | ++ | − |
| A-20 | NT | + | + | ++ | − |
| A-21 | + | ++ | ++ | ++ | − |
| A-22 | NT | + | NT | ++ | NT |
| A-23 | NT | ++ | ++ | ++ | NT |
| A-24 | + | ++ | ++ | ++ | NT |
| A-25 | + | ++ | ++ | ++ | NT |
| A-26 | NT | ++ | ++ | ++ | + |
| A-27 | + | ++ | ++ | ++ | + |
| A-28 | + | ++ | ++ | ++ | + |
| A-29 | + | ++ | ++ | ++ | NT |
| A-30 | + | ++ | ++ | ++ | + |
| A-31 | NT | ++ | + | ++ | NT |
| A-32 | − | ++ | + | ++ | − |
| A-33 | NT | ++ | + | ++ | NT |
| A-34 | − | ++ | + | ++ | − |
| A-35 | + | ++ | ++ | ++ | + |
| A-36 | + | ++ | + | ++ | − |
| A-37 | NT | ++ | + | ++ | − |
| A-38 | + | ++ | ++ | ++ | + |
| A-39 | − | ++ | + | ++ | − |
| A-40 | NT | + | + | ++ | NT |
| A-41 | NT | + | + | ++ | NT |
| A-42 | + | ++ | + | ++ | − |
| A-43 | NT | ++ | + | ++ | NT |
| A-44 | + | ++ | ++ | ++ | − |
| A-45 | + | ++ | ++ | ++ | − |
| A-46 | NT | + | + | ++ | NT |
| A-47 | + | ++ | ++ | ++ | + |
| A-48 | + | ++ | ++ | ++ | − |
| A-49 | + | ++ | ++ | ++ | − |
| A-50 | + | ++ | + | ++ | − |
| A-51 | − | ++ | ++ | ++ | − |
| A-52 | NT | ++ | + | ++ | − |
| A-53 | + | ++ | ++ | ++ | − |
| A-54 | + | ++ | ++ | ++ | − |
| A-55 | − | ++ | + | ++ | + |
| A-56 | + | ++ | + | ++ | − |
| A-57 | + | ++ | ++ | ++ | + |
| A-58 | + | ++ | + | ++ | + |
| A-59 | − | ++ | ++ | ++ | + |
| A-60 | + | ++ | ++ | ++ | NT |
| A-61 | NT | ++ | + | ++ | − |
| A-62 | + | ++ | + | ++ | + |
| A-63 | + | ++ | ++ | ++ | − |
| A-64 | NT | ++ | + | + | + |
| A-65 | + | ++ | ++ | ++ | + |
| A-66 | − | ++ | + | ++ | NT |
| A-67 | NT | ++ | + | ++ | NT |
| A-68 | − | + | − | + | − |
| A-69 | NT | ++ | ++ | ++ | NT |
| A-70 | + | ++ | ++ | ++ | + |
| A-71 | NT | ++ | ++ | ++ | NT |

Example 10: Parenteral Pharmaceutical Composition

To prepare a parenteral pharmaceutical composition suitable for administration by injection (subcutaneous, intravenous), 1-100 mg of a water-soluble salt of a compound Formula (A), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection Example 11: Oral Solution To prepare a pharmaceutical composition for oral delivery, a sufficient amount of a compound of Formula (A), or a pharmaceutically acceptable salt thereof, is added to water (with optional solubilizer(s), optional buffer(s) and taste masking excipients) to provide a 20 mg/mL solution.

Example 12: Oral Tablet

A tablet is prepared by mixing 20-50% by weight of a compound of Formula (A), or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example 13: Oral Capsule

To prepare a pharmaceutical composition for oral delivery, 10-500 mg of a compound of Formula (A), or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound of Formula (A), or a pharmaceutically acceptable salt thereof, is placed into Size 4 capsule, or size 1 capsule (hypromellose or hard gelatin) and the capsule is closed.

Example 14: Topical Gel Composition

To prepare a pharmaceutical topical gel composition, a compound of Formula (A), or a pharmaceutically acceptable salt thereof, is mixed with hydroxypropyl cellulose, propylene glycol, isopropyl myristate and purified alcohol USP. The resulting gel mixture is then incorporated into containers, such as tubes, which are suitable for topical administration.

The examples and embodiments described herein are for illustrative purposes only and various modifications or changes suggested to persons skilled in the art are to be included within the spirit and purview of this application and scope of the appended claims.

What is claimed is:

1. A compound that has the structure of Formula (A), or a pharmaceutically acceptable salt, pharmaceutically acceptable solvate, diastereomeric mixture, or individual enantiomers thereof:

Formula (A)

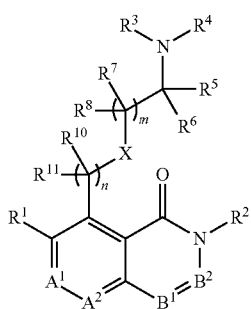

wherein:
A¹ and A² are independently N or CR$^A$, provided that A¹ and A² are not N at the same time;
each R$^A$ is independently hydrogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —$CO_2R^{17}$, —C(=O)$NR^{17}R^{18}$, —$NR^{17}R^{18}$, —$NR^{17}$C(=O)$NHR^{18}$, —$NR^{17}$C(=O)($C_1$-$C_4$alkyl), —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;
B¹ and B² are independently N or CR$^B$, provided that B¹ and B² are not N at the same time;
each R$^B$ is independently hydrogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —$CO_2R^{17}$, —C(=O)$NR^{17}R^{18}$, —$NR^{17}R^{18}$, —$NR^{17}$C(=O)$NHR^{18}$, —$NR^{17}$C(=O)($C_1$-$C_4$alkyl), —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$;
R¹ is unsubstituted or substituted $C_1$-$C_6$alkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if R¹ is substituted then R¹ is substituted with 1-2 $R^{13}$ and 0-2 $R^{14}$;
R² is unsubstituted or substituted $C_1$-$C_6$alkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$ alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if R² is substituted then R² is substituted with 1-2 $R^{15}$ and 0-2 $R^{16}$;
R³ and R⁴ are independently hydrogen, unsubstituted or substituted $C_1$-$C_6$ alkyl, unsubstituted or substituted $C_1$-$C_6$ fluoroalkyl, or unsubstituted or substituted $C_3$-$C_6$ cycloalkyl, wherein any substituted group of R³ and R⁴ is substituted with 1-4 $R^{12}$;
or R³ and R⁴ are taken together with the nitrogen atom with to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;
R⁵, R⁶, R⁷, R⁸, R¹⁰, and R¹¹ are each independently selected from the group consisting of hydrogen, unsubstituted or substituted $C_1$-$C_6$ alkyl, and unsubstituted or substituted $C_1$-$C_6$ fluoroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, —($C_1$-$C_4$ alkylene)-(unsubstituted or substituted monocyclic carbocycle or unsubstituted or substituted bicyclic carbocycle), or —($C_1$-$C_4$ alkylene)-(unsubstituted or substituted monocyclic heterocycle or unsubstituted or substituted bicyclic heterocycle), wherein if R⁵, R⁶, R⁷, R⁸, R¹⁰, and R¹¹ is substituted then R⁵, R⁶, R⁷, R⁸, R¹⁰, and R¹¹ is substituted with 1-2 $R^{15}$ and 0-2 $R^{16}$;
X is $NR^9$, O, or $CR^9R^{19}$;
R⁹ is hydrogen, unsubstituted or substituted $C_1$-$C_6$ alkyl, or unsubstituted or substituted benzyl, wherein if R⁹ is substituted then R⁹ is substituted with 1-4 $R^{12}$;
R¹⁹ is hydrogen, or unsubstituted or substituted $C_1$-$C_6$ alkyl, wherein if R¹⁹ is substituted then R¹⁹ is substituted with 1-4 $R^{12}$;
or R⁴ and any one of R⁵, R⁷, R⁹, or R¹¹ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;
or R⁵ and R⁶ are taken together with the carbon atom to which they are attached to form an unsubstituted or substituted monocyclic 4- to 7-membered carbocyclic ring, wherein if the carbocyclic ring is substituted then the carbocyclic ring is substituted with 1-4 $R^{12}$;
or R⁵ and any one of R⁷, R⁹, or R¹¹ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;
or R⁷ and one of R⁹ or R¹¹ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;
or R⁹ and R¹¹ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{12}$;
each $R^{12}$ is independently halogen, heterocycle, $C_1$-$C_4$alkyl, $C_1$-$C_4$alkoxy, $C_1$-$C_4$hydroxyalkyl, $C_1$-$C_4$aminoalkyl, $C_1$-$C_4$fluoroalkyl, $C_1$-$C_4$fluoroalkoxy, —CN, —$OR^{17}$, —$CO_2R^{17}$, —$C_1$-$C_4$alkyl$CO_2R^{17}$, —C(=O)$NR^{17}R^{18}$, —$NR^{17}R^{18}$, —$NR^{17}$C(=O)$NHR^{18}$, —$NR^{17}$C(O)$R^{18}$, —C(=NOR$^{17}$)R$^{18}$, —SR$^{17}$, —S(=O)(C$_1$-C$_4$alkyl), —SO$_2$(C$_1$-C$_4$alkyl), or —SO$_2$NR$^{17}$R$^{18}$;

each of R$^{13}$ and R$^{14}$ is independently hydrogen, halogen, unsubstituted or substituted C$_1$-C$_4$alkyl, unsubstituted or substituted C$_1$-C$_4$alkoxy, unsubstituted or substituted C$_1$-C$_4$fluoroalkyl, unsubstituted or substituted C$_1$-C$_4$fluoroalkoxy, unsubstituted or substituted heterocycle, —CN, —OH, —CO$_2$R$^{17}$, —C(=O)NR$^{17}$R$^{18}$, —NR$^{17}$R$^{18}$, —NR$^{17}$C(=O)R$^{18}$, —NR$^{17}$C(=O)NHR$^{18}$, —C(=NOR$^{17}$)R$^{18}$, —SR$^{17}$, —S(=O)(C$_1$-C$_4$alkyl), —SO$_2$(C$_1$-C$_4$alkyl), or —SO$_2$NR$^{17}$R$^{18}$, wherein if any group of R$^{13}$ and R$^{14}$ is substituted then the substituted group of R$^{13}$ and R$^{14}$ is substituted with 1-4 R$^{12}$;

each of R$^{15}$ and R$^{16}$ is independently hydrogen, halogen, unsubstituted or substituted C$_1$-C$_4$alkyl, unsubstituted or substituted C$_1$-C$_4$alkoxy, unsubstituted or substituted C$_1$-C$_4$fluoroalkyl, unsubstituted or substituted C$_1$-C$_4$fluoroalkoxy, unsubstituted or substituted heterocycle, —CN, —OH, —CO$_2$R$^{17}$, —C(=O)NR$^{17}$R$^{18}$, —NR$^{17}$R$^{18}$, —NR$^{17}$C(=O)R$^{18}$, —NR$^{17}$C(=O)NHR$^{18}$, —C(=NOR$^{17}$)R$^{18}$, —SR$^{17}$, —S(=O)(C$_1$-C$_4$alkyl), —SO$_2$(C$_1$-C$_4$alkyl), or —SO$_2$NR$^{17}$R$^{18}$, wherein if any group of R$^{15}$ and R$^{16}$ is substituted then the substituted group of R$^{15}$ and R$^{16}$ is substituted with 1-4 R$^{12}$;

each of R$^{17}$ and R$^{18}$ is independently hydrogen, C$_1$-C$_4$alkyl, C$_1$-C$_4$fluoroalkyl, C$_1$-C$_4$hydroxyalkyl, C$_1$-C$_4$aminoalkyl, or heterocycle;

m is 1, 2, 3, or 4; and n is 0, 1, 2, 3, or 4.

2. The compound of claim 1, or a pharmaceutically acceptable salt, pharmaceutically acceptable solvate, diastereomeric mixture, or individual enantiomers thereof, wherein X is NR$^9$ as shown in Formula (I):

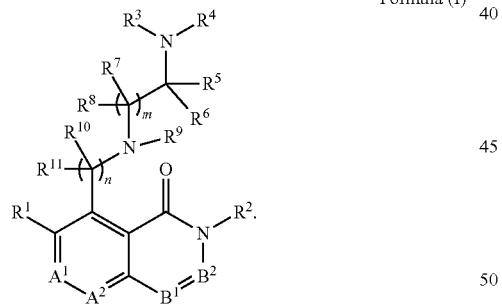

Formula (I)

3. The compound of claim 2, or a pharmaceutically acceptable salt, pharmaceutically acceptable solvate, diastereomeric mixture, or individual enantiomers thereof, wherein:

A$^1$ is CR$^A$; and A$^2$ is N;
or A$^1$ is N; and A$^2$ is CR$^A$;
or A$^1$ is CR$^A$; and A$^2$ is CR$^A$;
each R$^A$ is independently hydrogen, C$_1$-C$_4$alkyl, C$_1$-C$_4$fluoroalkyl, or —CN;
m is 1 or 2; and
n is 1 or 2.

4. The compound of claim 3, or a pharmaceutically acceptable salt, pharmaceutically acceptable solvate, diastereomeric mixture, or individual enantiomers thereof, wherein:

B$^1$ is N; and B$^2$ is CR$^B$;
or B$^1$ is CR$^B$; and B$^2$ is N;
or B$^1$ is CR$^B$; and B$^2$ is CR$^B$;
each R$^B$ is independently hydrogen, C$_1$-C$_4$alkyl, C$_1$-C$_4$fluoroalkyl, or —CN.

5. The compound of claim 4, wherein the compound of Formula (I) has the structure of Formula (Ia), Formula (Id), or Formula (Ig), or a pharmaceutically acceptable salt, pharmaceutically acceptable solvate, diastereomeric mixture, or individual enantiomers thereof:

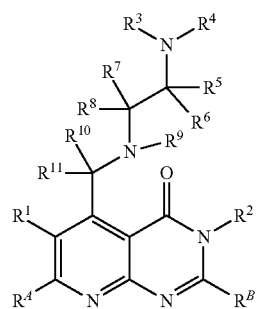

Formula (Ia)

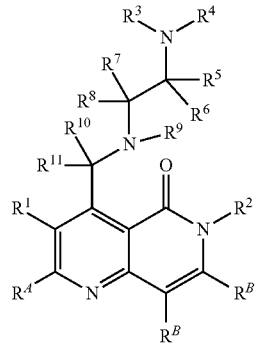

Formula (Id)

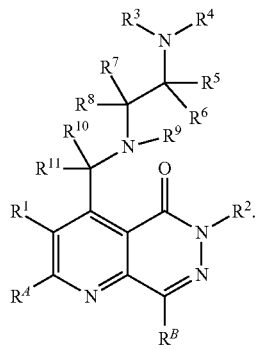

Formula (Ig)

6. The compound of claim 4, wherein the compound of Formula (I) has the structure of Formula (Ib), Formula (Ie), or Formula (Ih), or a pharmaceutically acceptable salt, pharmaceutically acceptable solvate, diastereomeric mixture, or individual enantiomers thereof:

101

Formula (Ib)

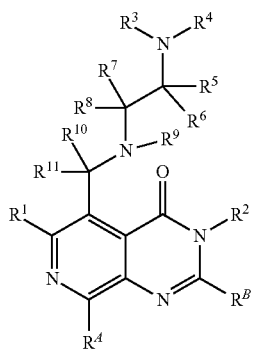

Formula (Ie)

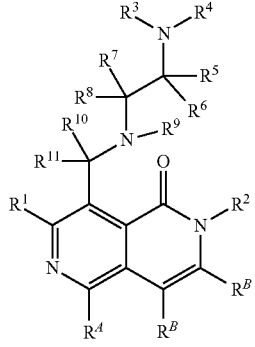

Formula (Ih)

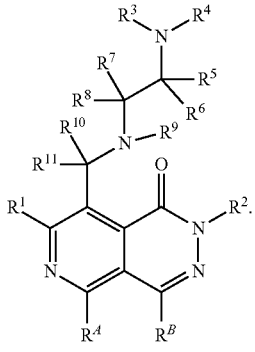

7. The compound of claim 4, wherein the compound of Formula (I) has the structure of Formula (Ic), Formula (If), or Formula (Ii), or a pharmaceutically acceptable salt, pharmaceutically acceptable solvate, diastereomeric mixture, or individual enantiomers thereof:

Formula (Ic)

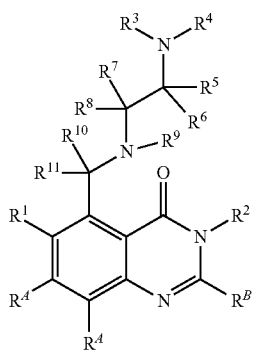

102

-continued

Formula (If)

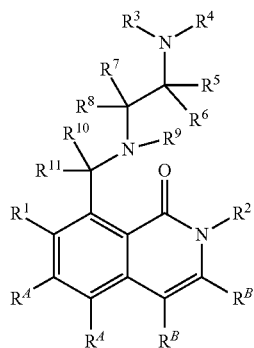

Formula (Ii)

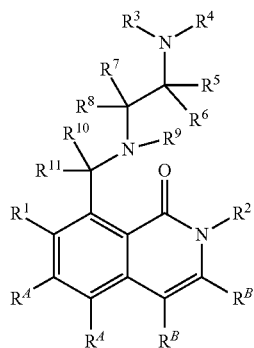

8. The compound of claim 1, or a pharmaceutically acceptable salt, pharmaceutically acceptable solvate, diastereomeric mixture, or individual enantiomers thereof, wherein:

$R^1$ is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if $R^1$ is substituted then $R^1$ is substituted with 1-2 $R^{13}$ and 0-2 $R^{14}$; and $R^2$ is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if $R^2$ is substituted then $R^2$ is substituted with 1-2 $R^{15}$ and 0-2 $R^{16}$.

9. The compound of claim 8, or a pharmaceutically acceptable salt, pharmaceutically acceptable solvate, diastereomeric mixture, or individual enantiomers thereof, wherein:

$R^1$ is an unsubstituted or substituted phenyl, wherein if $R^1$ is substituted then $R^1$ is substituted with 1-2 $R^{13}$ and 0-2 $R^{14}$; and $R^2$ is an unsubstituted or substituted phenyl, wherein if $R^2$ is substituted then $R^2$ is substituted with 1-2 $R^{15}$ and 0-2 $R^{16}$.

10. The compound of claim 9, or a pharmaceutically acceptable salt, pharmaceutically acceptable solvate, diastereomeric mixture, or individual enantiomers thereof, wherein:

$R^1$ is

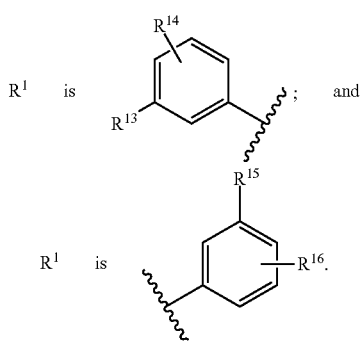

11. The compound of claim 10, or a pharmaceutically acceptable salt, pharmaceutically acceptable solvate, diastereomeric mixture, or individual enantiomers thereof, wherein:
- $R^{13}$ is hydrogen, halogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, or —CN, wherein if any group of $R^{13}$ is substituted then the substituted group of $R^{13}$ is substituted with $R^{12}$;
- $R^{14}$ is hydrogen, halogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}$C(=O)$NHR^{18}$, —$NR^{17}$C(=O)$R^{18}$, —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$; wherein if any group of $R^{14}$ is substituted then the substituted group of $R^{14}$ is substituted with $R^{12}$;
- $R^{15}$ is hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted heterocycle, —CN, —OH, —$CO_2R^{17}$, —C(=O)$NR^{17}R^{18}$, —$NR^{17}R^{18}$, —$NR^{17}$C(=O)$R^{18}$, —$NR^{17}$C(=O)$NHR^{18}$, —C(=$NOR^{17}$)$R^{18}$, —$SR^{17}$, —S(=O)($C_1$-$C_4$alkyl), —$SO_2$($C_1$-$C_4$alkyl), or —$SO_2NR^{17}R^{18}$, wherein if any group of $R^{15}$ is substituted then the substituted group of $R^{15}$ is substituted with $R^{12}$; and
- $R^{16}$ is hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, —CN, or —OH, wherein if any group of $R^{16}$ is substituted then the substituted group of $R^{16}$ is substituted with $R^{12}$.

12. The compound of claim 11, or a pharmaceutically acceptable salt, pharmaceutically acceptable solvate, diastereomeric mixture, or individual enantiomers thereof, wherein:
- $R^{13}$ is hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, or —CN, wherein if any group of $R^{13}$ is substituted then the substituted group of $R^{13}$ is substituted with $R^{12}$;
- $R^{14}$ is hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, —CN, —OH, wherein if any group of $R^{14}$ is substituted then the substituted group of $R^{14}$ is substituted with $R^{12}$;
- each $R^{15}$ is independently F, Cl, —$CF_3$, —CN, —OH, —$CO_2R^{17}$, or —C(=O)$NR^{17}R^{18}$; and
- each $R^{16}$ is independently hydrogen, halogen, unsubstituted or substituted $C_1$-$C_4$alkyl, unsubstituted or substituted $C_1$-$C_4$alkoxy, —CN, —OH, —$CO_2R^{17}$, —C(=O)$NR^{17}R^{18}$, —$SR^{17}$, —S(=O)($C_1$-$C_4$alkyl), —$SO_2$($C_1$-$C_4$alkyl), or —$SO_2NR^{17}R^{18}$; wherein if any group of $R^{16}$ is substituted then the substituted group of $R^{16}$ is substituted with $R^{12}$.

13. The compound of claim 1, or a pharmaceutically acceptable salt, pharmaceutically acceptable solvate, diastereomeric mixture, or individual enantiomers thereof, wherein:
- $R^3$ and $R^4$ are independently hydrogen, or unsubstituted or substituted $C_1$-$C_6$ alkyl, wherein any substituted group of $R^3$ and $R^4$ is substituted with 1-4 $R^{12}$;
- $R^5$ and $R^6$ are each independently selected from the group consisting of hydrogen, and unsubstituted or substituted $C_1$-$C_6$ alkyl, wherein any substituted group of $R^5$, and $R^6$ is substituted with 1-2 $R^{15}$ and 0-2 $R^{16}$;
- or $R^4$ and $R^5$ are taken together with the intervening atoms to which they are attached to form an unsubstituted or substituted monocyclic 4- to 7-membered heterocyclic ring, wherein if the heterocyclic ring is substituted then the heterocyclic ring is substituted with 1-4 $R^{12}$.

14. The compound of claim 13, or a pharmaceutically acceptable salt, pharmaceutically acceptable solvate, diastereomeric mixture, or individual enantiomers thereof, wherein:
- $R^3$ is hydrogen;
- $R^4$ is hydrogen, or unsubstituted or substituted $C_1$-$C_6$ alkyl;
- $R^5$ is hydrogen, or unsubstituted or substituted $C_1$-$C_6$ alkyl;
- or $R^4$ and $R^5$ are taken together with the intervening atoms to which they are attached to form an unsubstituted or substituted monocyclic 4- to 7-membered heterocyclic ring, wherein if the heterocyclic ring is substituted then the heterocyclic ring is substituted with 1-4 $R^{12}$; and
- $R^6$ is hydrogen.

15. The compound of claim 14, or a pharmaceutically acceptable salt, pharmaceutically acceptable solvate, diastereomeric mixture, or individual enantiomers thereof, wherein:
- $R^3$ is hydrogen;
- $R^4$ is hydrogen, methyl, ethyl, n-propyl, i-propyl, n-butyl, i-butyl, sec-butyl, or tert-butyl;
- $R^5$ is hydrogen, methyl, ethyl, n-propyl, i-propyl, n-butyl, i-butyl, sec-butyl, or tert-butyl;
- or $R^4$ and $R^5$ are taken together with the intervening atoms to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted pyrrolidinonyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl, wherein if the heterocyclic ring is substituted then the heterocyclic ring is substituted with 1-4 $R^{12}$;

$R^6$ is hydrogen; and $R^9$ is methyl, ethyl, n-propyl, i-propyl, n-butyl, i-butyl, sec-butyl, tert-butyl, or benzyl.

16. The compound claim 15, or a pharmaceutically acceptable salt, pharmaceutically acceptable solvate, diastereomeric mixture, or individual enantiomers thereof, wherein:

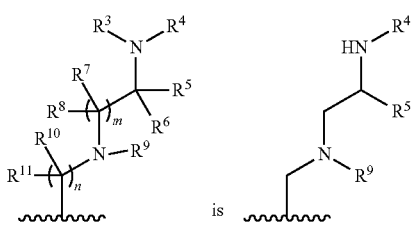

17. The compound of claim 16, or a pharmaceutically acceptable salt, pharmaceutically acceptable solvate, diastereomeric mixture, or individual enantiomers thereof, wherein:

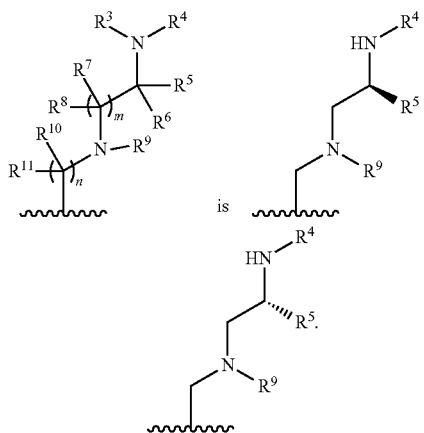

18. The compound of claim 15, or a pharmaceutically acceptable salt, pharmaceutically acceptable solvate, diastereomeric mixture, or individual enantiomers thereof, wherein:

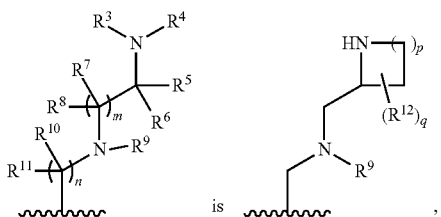

p is 1, 2, or 3; and q is 0, 1, or 2.

19. The compound of claim 18, or a pharmaceutically acceptable salt, pharmaceutically acceptable solvate, diastereomeric mixture, or individual enantiomers thereof, wherein:

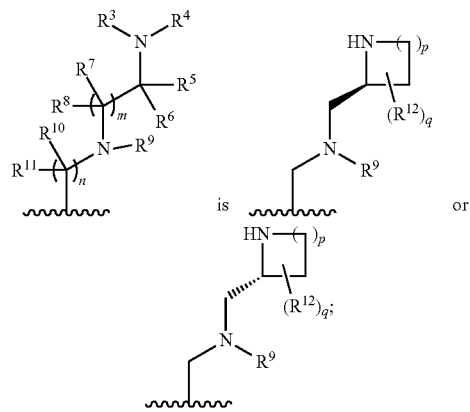

p is 1, 2, or 3; and q is 0, 1, or 2.

20. A compound that is:

5-{[(2-aminoethyl)(methyl)amino]methyl}-6-(3,5-dimethylphenyl)-3-(3-hydroxyphenyl)-3H,4H-pyrido[2,3-d]pyrimidin-4-one;

5-{[(2-aminoethyl)(ethyl)amino]methyl}-6-(3,5-dimethylphenyl)-3-(3-hydroxyphenyl)-3H,4H-pyrido[2,3-d]pyrimidin-4-one;

5-(((2-aminoethyl)(ethyl)amino)methyl)-6-(3-chloro-5-methylphenyl)-3-(3-fluoro-5-hydroxyphenyl)pyrido[2,3-d]pyrimidin-4(3H)-one;

5-{[(2-aminoethyl)(propyl)amino]methyl}-6-(3,5-dimethylphenyl)-3-(3-hydroxyphenyl)-3H,4H-pyrido[2,3-d]pyrimidin-4-one;

5-{[(2-aminoethyl)(benzyl)amino]methyl}-6-(3,5-dimethylphenyl)-3-(3-hydroxyphenyl)-3H,4H-pyrido[2,3-d]pyrimidin-4-one;

5-({[2-(benzylamino)ethyl](methyl)amino}methyl)-6-(3,5-dimethylphenyl)-3-(3-hydroxyphenyl)-3H,4H-pyrido[2,3-d]pyrimidin-4-one;

5-{[(1-aminopropan-2-yl)(methyl)amino]methyl}-6-(3,5-dimethylphenyl)-3-(3-hydroxyphenyl)-3H,4H-pyrido[2,3-d]pyrimidin-4-one;

5-({[(2S)-2-aminopropyl](methyl)amino}methyl)-6-(3,5-dimethylphenyl)-3-(3-hydroxyphenyl)-3H,4H-pyrido[2,3-d]pyrimidin-4-one;

5-({[(2S)-2-aminopropyl](ethyl)amino}methyl)-6-(3,5-dimethylphenyl)-3-(3-hydroxyphenyl)-3H,4H-pyrido[2,3-d]pyrimidin-4-one;

5-[(3-aminopyrrolidin-1-yl)methyl]-6-(3,5-dimethylphenyl)-3-(3-hydroxyphenyl)-3H,4H-pyrido[2,3-d]pyrimidin-4-one;

5-{[2-(aminomethyl)pyrrolidin-1-yl]methyl}-6-(3,5-dimethylphenyl)-3-(3-hydroxyphenyl)-3H,4H-pyrido[2,3-d]pyrimidin-4-one;

5-({[(1-aminocyclopentyl)methyl](methyl)amino}methyl)-6-(3,5-dimethylphenyl)-3-(3-hydroxyphenyl)-3H,4H-pyrido[2,3-d]pyrimidin-4-one;

6-(3,5-dimethylphenyl)-3-(3-hydroxyphenyl)-5-{[methyl(piperidin-2-ylmethyl)amino]methyl}-3H,4H-pyrido[2,3-d]pyrimidin-4-one;

6-(3,5-dimethylphenyl)-3-(3-hydroxyphenyl)-5-({methyl[(2R)-piperidin-2-ylmethyl]amino}methyl)-3H,4H-pyrido[2,3-d]pyrimidin-4-one;

6-(3,5-dimethylphenyl)-3-(3-hydroxyphenyl)-5-({methyl[(2S)-piperidin-2-ylmethyl]amino}methyl)-3H,4H-pyrido[2,3-d]pyrimidin-4-one;

6-(3,5-dimethylphenyl)-3-(3-hydroxyphenyl)-5-({methyl[(2R)-pyrrolidin-2-ylmethyl]amino}methyl)-3H,4H-pyrido[2,3-d]pyrimidin-4-one;

6-(3,5-dimethylphenyl)-3-(3-hydroxyphenyl)-5-({methyl[(2S)-pyrrolidin-2-ylmethyl]amino}methyl)-3H,4H-pyrido[2,3-d]pyrimidin-4-one;

5-({[(2S)-azetidin-2-ylmethyl](methyl)amino}methyl)-6-(3,5-dimethylphenyl)-3-(3-hydroxyphenyl)-3H,4H-pyrido[2,3-d]pyrimidin-4-one;

6-(3,5-dimethylphenyl)-3-(3-hydroxyphenyl)-5-{[methyl(morpholin-3-ylmethyl)amino]methyl}-3H,4H-pyrido[2,3-d]pyrimidin-4-one;

3-(3-hydroxyphenyl)-5-{[methyl(piperidin-2-ylmethyl)amino]methyl}-6-(2-methylphenyl)-3H,4H-pyrido[2,3-d]pyrimidin-4-one;

3-(3-hydroxyphenyl)-5-{[methyl(piperidin-2-ylmethyl)amino]methyl}-6-(3-methylphenyl)-3H,4H-pyrido[2,3-d]pyrimidin-4-one;

3-(3-hydroxyphenyl)-5-{[methyl(piperidin-2-ylmethyl)amino]methyl}-6-[3-(propan-2-yl)phenyl]-3H,4H-pyrido[2,3-d]pyrimidin-4-one;

3-(3-hydroxyphenyl)-6-(3-methoxyphenyl)-5-{[methyl(piperidin-2-ylmethyl)amino]methyl}-3H,4H-pyrido[2,3-d]pyrimidin-4-one;

6-(3-chlorophenyl)-3-(3-hydroxyphenyl)-5-{[methyl(piperidin-2-ylmethyl)amino]methyl}-3H,4H-pyrido[2,3-d]pyrimidin-4-one;

6-(3-fluoro-5-methylphenyl)-3-(3-hydroxyphenyl)-5-{[methyl(piperidin-2-ylmethyl)amino]methyl}-3H,4H-pyrido[2,3-d]pyrimidin-4-one;

6-(3-fluoro-2-methylphenyl)-3-(3-hydroxyphenyl)-5-{[methyl(piperidin-2-ylmethyl)amino]methyl}-3H,4H-pyrido[2,3-d]pyrimidin-4-one;

6-(3,5-dimethylphenyl)-3-(3-fluoro-5-hydroxyphenyl)-5-({methyl[(2 S)-piperidin-2-ylmethyl]amino}methyl)-3H,4H-pyrido[2,3-d]pyrimidin-4-one;

6-(3-chloro-5-methylphenyl)-3-(3-fluoro-5-hydroxyphenyl)-5-({methyl[(2 S)-piperidin-2-ylmethyl]amino}methyl)-3H,4H-pyrido[2,3-d]pyrimidin-4-one;

6-(3-chloro-5-methylphenyl)-3-(3-hydroxyphenyl)-5-({methyl[(2S)-piperidin-2-ylmethyl]amino}methyl)-3H,4H-pyrido[2,3-d]pyrimidin-4-one;

6-(3-chloro-5-methylphenyl)-3-(3-hydroxyphenyl)-5-({methyl[(2 S)-pyrrolidin-2-ylmethyl]amino}methyl)-3H,4H-pyrido[2,3-d]pyrimidin-4-one;

3-[6-(3-chloro-5-methylphenyl)-5-({methyl[(2S)-pyrrolidin-2-ylmethyl]amino}methyl)-4-oxo-3H,4H-pyrido[2,3-d]pyrimidin-3-yl]benzamide;

6-[3-(2-hydroxyethyl)phenyl]-3-(3-hydroxyphenyl)-5-({methyl[(2S)-pyrrolidin-2-ylmethyl]amino}methyl)-3H,4H-pyrido[2,3-d]pyrimidin-4-one;

6-(3,5-dimethylphenyl)-3-(3-methoxyphenyl)-5-({methyl[(2S)-pyrrolidin-2-ylmethyl]amino}methyl)-3H,4H-pyrido[2,3-d]pyrimidin-4-one;

6-[3-(hydroxymethyl)phenyl]-3-(3-hydroxyphenyl)-5-({methyl[(2S)-pyrrolidin-2-ylmethyl]amino}methyl)-3H,4H-pyrido[2,3-d]pyrimidin-4-one;

6-(3-chloro-5-fluorophenyl)-3-(3-hydroxyphenyl)-5-({methyl[(2S)-pyrrolidin-2-ylmethyl]amino}methyl)-3H,4H-pyrido[2,3-d]pyrimidin-4-one;

6-(3-fluoro-5-methylphenyl)-3-(3-hydroxyphenyl)-5-({methyl[(2 S)-pyrrolidin-2-ylmethyl]amino}methyl)-3H,4H-pyrido[2,3-d]pyrimidin-4-one;

6-[3-(hydroxymethyl)-5-methylphenyl]-3-(3-hydroxyphenyl)-5-({methyl[(2S)-pyrrolidin-2-ylmethyl]amino}methyl)-3H,4H-pyrido[2, 3-d]pyrimidin-4-one;

6-[3-chloro-5-(hydroxymethyl)phenyl]-3-(3-hydroxyphenyl)-5-({methyl[(2 S)-pyrrolidin-2-ylmethyl]amino}methyl)-3H,4H-pyrido[2, 3-d]pyrimidin-4-one;

3-[6-(3,5-dimethylphenyl)-5-({methyl[(2S)-pyrrolidin-2-ylmethyl]amino}methyl)-4-oxo-3H,4H-pyrido[2,3-d]pyrimidin-3-yl]benzamide;

6-(3,5-dimethylphenyl)-3-[3-(hydroxymethyl)phenyl]-5-({methyl[(2S)-pyrrolidin-2-ylmethyl]amino}methyl)-3H,4H-pyrido[2,3-d]pyrimidin-4-one;

6-(3,5-dimethylphenyl)-3-(4-hydroxyphenyl)-5-({methyl[(2S)-pyrrolidin-2-ylmethyl]amino}methyl)-3H,4H-pyrido[2,3-d]pyrimidin-4-one;

3-[6-(3,5-dimethylphenyl)-5-({methyl[(2S)-pyrrolidin-2-ylmethyl]amino}methyl)-4-oxo-3H,4H-pyrido[2,3-d]pyrimidin-3-yl]benzonitrile;

3-[6-(3,5-dimethylphenyl)-5-({methyl[(2S)-pyrrolidin-2-ylmethyl]amino}methyl)-4-oxo-3H,4H-pyrido[2, 3-d]pyrimidin-3-yl]-N-methylbenzamide;

6-(3,5-dimethylphenyl)-3-(3-hydroxy-5-methylphenyl)-5-({methyl[(2S)-pyrrolidin-2-ylmethyl]amino}methyl)-3H,4H-pyrido[2,3-d]pyrimidin-4-one;

6-(3,5-dimethylphenyl)-3-(3-fluoro-5-hydroxyphenyl)-5-({methyl[(2S)-pyrrolidin-2-ylmethyl]amino}methyl)-3H,4H-pyrido[2,3-d]pyrimidin-4-one;

3-[6-(3,5-dimethylphenyl)-5-({methyl[(2S)-pyrrolidin-2-ylmethyl]amino}methyl)-4-oxo-3H,4H-pyrido[2,3-d]pyrimidin-3-yl]-5-fluorobenzonitrile;

6-(3-chloro-5-methylphenyl)-3-(3-fluoro-5-hydroxyphenyl)-5-({methyl[(2S)-pyrrolidin-2-ylmethyl]amino}methyl)-3H,4H-pyrido[2,3-d]pyrimidin-4-one;

6-(3-chloro-5-methylphenyl)-3-[3-hydroxy-5-(trifluoromethyl)phenyl]-5-({methyl[(2S)-pyrrolidin-2-ylmethyl]amino}methyl)-3H,4H-pyrido[2,3-d]pyrimidin-4-one;

3-(3-chloro-5-hydroxyphenyl)-6-(3-chloro-5-methylphenyl)-5-({methyl[(2S)-pyrrolidin-2-ylmethyl]amino}methyl)-3H,4H-pyrido[2,3-d]pyrimidin-4-one;

3-[6-(3-chloro-5-methylphenyl)-5-({methyl[(2S)-pyrrolidin-2-ylmethyl]amino}methyl)-4-oxo-3H,4H-pyrido[2,3-d]pyrimidin-3-yl]-5-fluorobenzamide;

3-[6-(3-chloro-5-methylphenyl)-5-({methyl[(2R)-pyrrolidin-2-ylmethyl]amino}methyl)-4-oxo-3H,4H-pyrido[2,3-d]pyrimidin-3-yl]-5-fluorobenzamide;

6-(3-chloro-5-methylphenyl)-3-[3-hydroxy-5-(trifluoromethoxy)phenyl]-5-({methyl[(2S)-pyrrolidin-2-ylmethyl]amino}methyl)-3H,4H-pyrido[2,3-d]pyrimidin-4-one;

6-(3-chloro-5-methylphenyl)-3-(3-fluoro-5-hydroxyphenyl)-5-({methyl[(2R)-pyrrolidin-2-ylmethyl]amino}methyl)-3H,4H-pyrido[2,3-d]pyrimidin-4-one;

6-(3-chloro-5-methylphenyl)-3-(2-fluoro-5-hydroxyphenyl)-5-({methyl[(2S)-pyrrolidin-2-ylmethyl]amino}methyl)-3H,4H-pyrido[2,3-d]pyrimidin-4-one;

6-(3,5-dimethylphenyl)-3-(3-fluoro-5-hydroxyphenyl)-2-methyl-5-({methyl[(2S)-pyrrolidin-2-ylmethyl]amino}methyl)-3H,4H-pyrido[2,3-d]pyrimidin-4-one;

6-(3-chloro-5-methylphenyl)-3-(3-hydroxyphenyl)-2-methyl-5-({methyl[(2S)-pyrrolidin-2-ylmethyl]amino}methyl)-3H,4H-pyrido[2,3-d]pyrimidin-4-one;

6-(3-chloro-5-methylphenyl)-2-ethyl-3-(3-hydroxyphenyl)-5-({methyl[(2S)-pyrrolidin-2-ylmethyl]amino}methyl)-3H,4H-pyrido[2,3-d]pyrimidin-4-one;

6-(3-chloro-5-methylphenyl)-3-(3-hydroxyphenyl)-5-({methyl[(2S)-pyrrolidin-2-ylmethyl]amino}methyl)-2-(propan-2-yl)-3H,4H-pyrido[2,3-d]pyrimidin-4-one;

6-(3-chloro-5-methylphenyl)-3-(3-fluoro-5-hydroxyphenyl)-2-methyl-5-({methyl[(2S)-pyrrolidin-2-ylmethyl]amino}methyl)-3H,4H-pyrido[2,3-d]pyrimidin-4-one;

3-[6-(3-chloro-5-methylphenyl)-2-methyl-5-({methyl[(2S)-pyrrolidin-2-ylmethyl]amino}methyl)-4-oxo-3H,4H-pyrido[2,3-d]pyrimidin-3-yl]-5-fluorobenzonitrile;

5-({[(2S)-2-aminobutyl](methyl)amino}methyl)-6-(3,5-dimethylphenyl)-3-(3-hydroxyphenyl)-3H,4H-pyrido[2,3-d]pyrimidin-4-one;

5-({[(2S)-2-aminobutyl](methyl)amino}methyl)-6-(3,5-dimethylphenyl)-3-(3-fluoro-5-hydroxyphenyl)-3H,4H-pyrido[2,3-d]pyrimidin-4-one;

5-({[(2 S)-2-aminobutyl](methyl)amino}methyl)-6-(3,5-dimethylphenyl)-3-[3-hydroxy-5-(trifluoromethyl)phenyl]-3H,4H-pyrido[2,3-d]pyrimidin-4-one;

3-[5-({[(2 S)-2-aminobutyl](methyl)amino}methyl)-6-(3,5-dimethylphenyl)-4-oxo-3H,4H-pyrido[2,3-d]pyrimidin-3-yl]-5-fluorobenzamide;

5-({[(2S)-2-aminobutyl](methyl)amino}methyl)-6-(3-chloro-5-methylphenyl)-[3-hydroxy-5-(trifluoromethyl)phenyl]-3H,4H-pyrido[2,3-d]pyrimidin-4-one;

5-({[(2S)-2-aminobutyl](methyl)amino}methyl)-6-(3-chloro-5-methylphenyl)-3-(3-fluoro-5-hydroxyphenyl)-3H,4H-pyrido[2,3-d]pyrimidin-4-one;

5-{[(2-aminoethyl)(ethyl)amino]methyl}-6-(3-chloro-5-methylphenyl)-3-(3-fluoro-5-hydroxyphenyl)-2-methyl-3H,4H-pyrido[2,3-d]pyrimidin-4-one;

ethyl 2-{[2-({[3-(3,5-dimethylphenyl)-6-(3-hydroxyphenyl)-4-oxo-3H,4H-pyrido[2,3-d]pyrimidin-5-yl]methyl}(ethyl)amino)ethyl]amino}acetate;

6-(3-methyl-5-chlorophenyl)-3-(3-cyano-5-hydroxyphenyl)-5-({methyl[(2 S)-pyrrolidin-2-ylmethyl]amino}methyl)-3H,4H-pyrido[2,3-d]pyrimidin-4-one;

6-(3-methoxy-5-chlorophenyl)-3-(3-fluoro-5-hydroxyphenyl)-5-({methyl[(2 S)-pyrrolidin-2-ylmethyl]amino}methyl)-3H,4H-pyrido[2,3-d]pyrimidin-4-one;

6-(3-methyl-5-fluorophenyl)-3-(3-fluoro-5-hydroxyphenyl)-5-({methyl[(2 S)-pyrrolidin-2-ylmethyl]amino}methyl)-3H,4H-pyrido[2,3-d]pyrimidin-4-one;

6-(3-methyl-5-chlorophenyl)-3-(3-hydroxyphenyl)-2-cyano-5-({methyl[(2 S)-pyrrolidin-2-ylmethyl]amino}methyl)-3H,4H-pyrido[2,3-d]pyrimidin-4-one;

6-(3-methyl-5-chlorophenyl)-3-(3-fluoro-5-hydroxyphenyl)-2-cyano-5-({methyl[(2 S)-pyrrolidin-2-ylmethyl]amino}methyl)-3H,4H-pyrido[2,3-d]pyrimidin-4-one;

6-(3-methyl-5-chlorophenyl)-3-(3-hydroxyphenyl)-5-({methyl[(2 S)-4-fluoropyrrolidin-2-ylmethyl]amino}methyl)-3H,4H-pyrido[2,3-d]pyrimidin-4-one;

6-(3-methyl-5-chlorophenyl)-3-(3-fluoro-5-hydroxyphenyl)-5-({methyl[(2 S)-4-fluoropyrrolidin-2-ylmethyl]amino}methyl)-3H,4H-pyrido[2,3-d]pyrimidin-4-one;

6-(3-methoxy-5-chlorophenyl)-3-(3-fluoro-5-hydroxyphenyl)-5-({methyl[(2 S)-4-fluoropyrrolidin-2-ylmethyl]amino}methyl)-3H,4H-pyrido[2,3-d]pyrimidin-4-one;

6-(3-methoxy-5-fluorophenyl)-3-(3-fluoro-5-hydroxyphenyl)-5-({methyl[(2 S)-4-fluoropyrrolidin-2-ylmethyl]amino}methyl)-3H,4H-pyrido[2,3-d]pyrimidin-4-one;

6-(3-methyl-5-chlorophenyl)-3-(3-hydroxyphenyl)-5-({methyl[(2 S)-4,4-difluoropyrrolidin-2-ylmethyl]amino}methyl)-3H,4H-pyrido[2,3-d]pyrimidin-4-one;

6-(3-methyl-5-chlorophenyl)-3-(3-fluoro-5-hydroxyphenyl)-5-({methyl[(2 S)-4,4-difluoropyrrolidin-2-ylmethyl]amino}methyl)-3H,4H-pyrido[2,3-d]pyrimidin-4-one;

6-(3-methoxy-5-chlorophenyl)-3-(3-fluoro-5-hydroxyphenyl)-5-({methyl[(2 S)-4,4-difluoropyrrolidin-2-ylmethyl]amino}methyl)-3H,4H-pyrido[2,3-d]pyrimidin-4-one;

6-(3-methoxy-5-fluorophenyl)-3-(3-fluoro-5-hydroxyphenyl)-5-({methyl[(2 S)-4,4-difluoropyrrolidin-2-ylmethyl]amino}methyl)-3H,4H-pyrido[2,3-d]pyrimidin-4-one;

(5 S)-5-(((((6-(3-chloro-5-methylphenyl)-3-(3-fluoro-5-hydroxyphenyl)-4-oxo-3,4-dihydropyrido[2,3-d]pyrimidin-5-yl)methyl)(methyl)amino)methyl)pyrrolidine-3-carboxylic acid;

2-((5 S)-5-(((((6-(3-chloro-5-methylphenyl)-3-(3-fluoro-5-hydroxyphenyl)-4-oxo-3,4-dihydropyrido[2,3-d]pyrimidin-5-yl)methyl)(methyl)amino)methyl)pyrrolidin-3-yl)acetic acid;

3-((5 S)-5-(((((6-(3-chloro-5-methylphenyl)-3-(3-fluoro-5-hydroxyphenyl)-4-oxo-3,4-dihydropyrido[2,3-d]pyrimidin-5-yl)methyl)(methyl)amino)methyl)pyrrolidin-3-yl)propanoic acid;

(S)-6-(3-chloro-5-methylphenyl)-3-(3-fluoro-5-hydroxyphenyl)-5-(((2-hydroxyethyl)(pyrrolidin-2-ylmethyl)amino)methyl)pyrido[2,3-d]pyrimidin-4(3H)-one;

(S)-2-(((6-(3-chloro-5-methylphenyl)-3-(3-fluoro-5-hydroxyphenyl)-4-oxo-3,4-dihydropyrido[2,3-d]pyrimidin-5-yl)methyl)(pyrrolidin-2-ylmethyl)amino)acetic acid;

6-(3-methyl-5-chlorophenyl)-3-(3-hydroxyphenyl)-5-({methyl[(S)-azetidin-2-ylmethyl]amino}methyl)-3H,4H-pyrido[2,3-d]pyrimidin-4-one;

6-(3-methyl-5-chlorophenyl)-3-(3-fluoro-5-hydroxyphenyl)-5-({methyl[(S)-azetidin-2-ylmethyl]amino}methyl)-3H,4H-pyrido[2,3-d]pyrimidin-4-one;

6-(3-methyl-5-chlorophenyl)-3-(3-hydroxy-5-trifluoromethylphenyl)-5-({methyl[(S)-azetidin-2-ylmethyl]amino}methyl)-3H,4H-pyrido[2,3-d]pyrimidin-4-one;

3-(3-hydroxy-phenyl)-5-[(methyl-piperidin-2-ylmethyl-amino)-methyl]-6-naphthalen-1-yl-3H-pyrido[2, 3-d]pyrimidin-4-one;

6-(2-Fluoro-3,5-dimethyl-phenyl)-3-(3-hydroxy-phenyl)-5-[(methyl-piperidin-2-ylmethyl-amino)-methyl]-3H-pyrido[2,3-d]pyrimidin-4-one;

(S)-4-(((2-aminobutyl)(methyl)amino)methyl)-3-(3,5-dimethylphenyl)-6-(3-hydroxyphenyl)-1,6-naphthyridin-5(6H)-one;

(S)-4-(((2-aminobutyl)(methyl)amino)methyl)-3-(3-chloro-5-methylphenyl)-6-(3-hydroxyphenyl)-1,6-naphthyridin-5(6H)-one;

(S)-4-(((2-aminobutyl)(methyl)amino)methyl)-3-(3-chloro-5-methylphenyl)-6-(3-fluoro-5-hydroxyphenyl)-1,6-naphthyridin-5(6H)-one;

(S)-4-(((2-aminobutyl)(methyl)amino)methyl)-3-(3-chloro-5-methylphenyl)-6-(3-fluoro-5-hydroxyphenyl)-7-methyl-1,6-naphthyridin-5(6H)-one;

(S)-4-(((2-aminobutyl)(methyl)amino)methyl)-3-(3-chloro-5-methylphenyl)-6-(3-fluoro-5-hydroxyphenyl)-5-oxo-5,6-dihydro-1,6-naphthyridine-7-carbonitrile;

(S)-4-(((2-aminobutyl)(methyl)amino)methyl)-3-(3-chloro-5-methylphenyl)-6-(3-fluoro-5-hydroxyphenyl)-7-(trifluoromethyl)-1,6-naphthyridin-5(6H)-one;

(S)-4-(((2-aminobutyl)(methyl)amino)methyl)-3-(3-chloro-5-methylphenyl)-6-(3-hydroxy-5-(trifluoromethyl)phenyl)-1,6-naphthyridin-5(6H)-one;

(S)-3-(3-chloro-5-methylphenyl)-6-(3-hydroxyphenyl)-4-((methyl(pyrrolidin-2-ylmethyl)amino)methyl)-1,6-naphthyridin-5(6H)-one;

(S)-3-(3-chloro-5-methylphenyl)-6-(3-hydroxyphenyl)-7-methyl-4-((methyl(pyrrolidin-2-ylmethyl)amino)methyl)-1,6-naphthyridin-5(6H)-one;
(S)-3-(3-chloro-5-methylphenyl)-6-(3-fluoro-5-hydroxyphenyl)-4-((methyl(pyrrolidin-2-ylmethyl)amino)methyl)-1,6-naphthyridin-5(6H)-one;
(S)-3-(3-chloro-5-methylphenyl)-6-(3-fluoro-5-hydroxyphenyl)-7-methyl-4-((methyl(pyrrolidin-2-ylmethyl)amino)methyl)-1,6-naphthyridin-5(6H)-one;
(S)-3-(3-chloro-5-methylphenyl)-6-(3-fluoro-5-hydroxyphenyl)-4-((methyl(pyrrolidin-2-ylmethyl)amino)methyl)-7-(trifluoromethyl)-1,6-naphthyridin-5(6H)-one;
(S)-3-(3-chloro-5-methylphenyl)-6-(3-hydroxy-5-(trifluoromethyl)phenyl)-4-((methyl(pyrrolidin-2-ylmethyl)amino)methyl)-1,6-naphthyridin-5(6H)-one;
(S)-3-(3-chloro-5-methylphenyl)-6-(3-hydroxy-5-(trifluoromethyl)phenyl)-7-methyl-4-((methyl(pyrrolidin-2-ylmethyl)amino)methyl)-1,6-naphthyridin-5(6H)-one;
(S)-3-(3-chloro-5-methylphenyl)-6-(3-hydroxy-5-(trifluoromethyl)phenyl)-4-((methyl(pyrrolidin-2-ylmethyl)amino)methyl)-5-oxo-5,6-dihydro-1,6-naphthyridine-7-carbonitrile;
(S)-3-(3-(3-chloro-5-methylphenyl)-4-((methyl(pyrrolidin-2-ylmethyl)amino)methyl)-5-oxo-1,6-naphthyridin-6(5H)-yl)-5-hydroxybenzonitrile;
(S)-3-(3-fluoro-5-methylphenyl)-6-(3-hydroxyphenyl)-4-((methyl(pyrrolidin-2-ylmethyl)amino)methyl)-1,6-naphthyridin-5(6H)-one;
(S)-3-(3-fluoro-5-methyl phenyl)-6-(3-hydroxyphenyl)-7-methyl-4-((methyl(pyrrolidin-2-ylmethyl)amino)methyl)-1,6-naphthyridin-5(6H)-one;
(S)-6-(3-fluoro-5-hydroxyphenyl)-3-(3-fluoro-5-methylphenyl)-4-((methyl(pyrrolidin-2-ylmethyl)amino)methyl)-1,6-naphthyridin-5(6H)-one;
(S)-6-(3-fluoro-5-hydroxyphenyl)-3-(3-fluoro-5-methylphenyl)-7-methyl-4-((methyl(pyrrolidin-2-ylmethyl)amino)methyl)-1,6-naphthyridin-5(6H)-one;
(S)-6-(3-fluoro-5-hydroxyphenyl)-3-(3-fluoro-5-methylphenyl)-4-((methyl(pyrrolidin-2-ylmethyl)amino)methyl)-7-(trifluoromethyl)-1,6-naphthyridin-5(6H)-one;
(S)-3-(3-fluoro-5-methyl phenyl)-6-(3-hydroxy-5-(trifluoromethyl)phenyl)-4-((methyl(pyrrolidin-2-ylmethyl)amino)methyl)-1,6-naphthyridin-5(6H)-one;
(S)-3-(3-fluoro-5-methyl phenyl)-6-(3-hydroxy-5-(trifluoromethyl)phenyl)-7-methyl-4-((methyl(pyrrolidin-2-ylmethyl)amino)methyl)-1,6-naphthyridin-5(6H)-one;
(S)-3-(3-fluoro-5-methyl phenyl)-6-(3-hydroxy-5-(trifluoromethyl)phenyl)-4-((methyl(pyrrolidin-2-ylmethyl)amino)methyl)-5-oxo-5,6-dihydro-1,6-naphthyridine-7-carbonitrile;
(S)-3-(3, 5-dimethylphenyl)-6-(3-hydroxyphenyl)-4-((methyl(pyrrolidin-2-ylmethyl)amino)methyl)-1,6-naphthyridin-5(6H)-one;
(S)-3-(3, 5-dimethylphenyl)-6-(3-hydroxyphenyl)-7-methyl-4-((methyl(pyrrolidin-2-ylmethyl)amino)methyl)-1,6-naphthyridin-5(6H)-one;
(S)-3-(3, 5-dimethylphenyl)-6-(3-fluoro-5-hydroxyphenyl)-4-((methyl(pyrrolidin-2-ylmethyl)amino)methyl)-1,6-naphthyridin-5(6H)-one;
(S)-3-(3, 5-dimethylphenyl)-6-(3-fluoro-5-hydroxyphenyl)-7-methyl-4-((methyl(pyrrolidin-2-ylmethyl)amino)methyl)-1,6-naphthyridin-5(6H)-one;
(S)-3-(3, 5-dimethylphenyl)-6-(3-fluoro-5-hydroxyphenyl)-4-((methyl(pyrrolidin-2-ylmethyl)amino)methyl)-7-(trifluoromethyl)-1,6-naphthyridin-5(6H)-one;
(S)-3-(3, 5-dimethylphenyl)-6-(3-hydroxy-5-(trifluoromethyl)phenyl)-4-((methyl(pyrrolidin-2-ylmethyl)amino)methyl)-1,6-naphthyridin-5(6H)-one;
(S)-3-(3, 5-dimethylphenyl)-6-(3-hydroxy-5-(trifluoromethyl)phenyl)-7-methyl-4-((methyl(pyrrolidin-2-ylmethyl)amino)methyl)-1,6-naphthyridin-5(6H)-one;
(S)-3-(3, 5-dimethylphenyl)-6-(3-hydroxy-5-(trifluoromethyl)phenyl)-4-((methyl(pyrrolidin-2-ylmethyl)amino)methyl)-5-oxo-5,6-dihydro-1,6-naphthyridine-7-carbonitrile;
(S)-3-(3-(3,5-dimethylphenyl)-4-((methyl(pyrrolidin-2-ylmethyl)amino)methyl)-5-oxo-1,6-naphthyridin-6(5H)-yl)-5-hydroxybenzonitrile;
(S)-3-(3-chloro-5-methoxyphenyl)-6-(3-fluoro-5-hydroxyphenyl)-4-((methyl(pyrrolidin-2-ylmethyl)amino)methyl)-1,6-naphthyridin-5(6H)-one;
(S)-6-(3-fluoro-5-hydroxyphenyl)-3-(3-fluoro-5-methoxyphenyl)-4-((methyl(pyrrolidin-2-ylmethyl)amino)methyl)-1,6-naphthyridin-5(6H)-one;
(S)-4-(((2-aminobutyl)(methyl)amino)methyl)-3-(3, 5-dimethylphenyl)-6-(3-hydroxyphenyl)pyrido[2, 3-d]pyridazin-5(6H)-one;
(S)-4-(((2-aminobutyl)(methyl)amino)methyl)-3-(3-chloro-5-methylphenyl)-6-(3-hydroxyphenyl)pyrido[2, 3-d]pyridazin-5(6H)-one;
(S)-4-(((2-aminobutyl)(methyl)amino)methyl)-3-(3-chloro-5-methylphenyl)-6-(3-fluoro-5-hydroxyphenyl)pyrido[2, 3-d]pyridazin-5(6H)-one;
(S)-4-(((2-aminobutyl)(methyl)amino)methyl)-3-(3-chloro-5-methylphenyl)-6-(3-hydroxy-5-(trifluoromethyl)phenyl)pyrido[2,3-d]pyridazin-5(6H)-one;
(S)-3-(3-chloro-5-methylphenyl)-6-(3-hydroxyphenyl)-4-((methyl(pyrrolidin-2-ylmethyl)amino)methyl)pyrido[2, 3-d]pyridazin-5(6H)-one;
(S)-3-(3-chloro-5-methylphenyl)-6-(3-fluoro-5-hydroxyphenyl)-4-((methyl(pyrrolidin-2-ylmethyl)amino)methyl)pyrido[2, 3-d]pyridazin-5(6H)-one;
(S)-3-(3-chloro-5-methylphenyl)-6-(3-hydroxy-5-(trifluoromethyl)phenyl)-4-((methyl(pyrrolidin-2-ylmethyl)amino)methyl)pyrido[2, 3-d]pyridazin-5(6H)-one;
(S)-3-(3-(3-chloro-5-methylphenyl)-4-((methyl(pyrrolidin-2-ylmethyl)amino)methyl)-5-oxopyrido[2,3-d]pyridazin-6(5H)-yl)-5-hydroxybenzonitrile;
(S)-3-(3-fluoro-5-methylphenyl)-6-(3-hydroxyphenyl)-4-((methyl(pyrrolidin-2-ylmethyl)amino)methyl)pyrido[2,3-d]pyridazin-5(6H)-one;
(S)-6-(3-fluoro-5-hydroxyphenyl)-3-(3-fluoro-5-methylphenyl)-4-((methyl(pyrrolidin-2-ylmethyl)amino)methyl)pyrido[2,3-d]pyridazin-5(6H)-one;
(S)-3-(3-fluoro-5-methylphenyl)-6-(3-hydroxy-5-(trifluoromethyl)phenyl)-4-((methyl(pyrrolidin-2-ylmethyl)amino)methyl)pyrido[2,3-d]pyridazin-5(6H)-one;
(S)-3-(3,5-dimethylphenyl)-6-(3-hydroxyphenyl)-4-((methyl(pyrrolidin-2-ylmethyl)amino)methyl)pyrido[2,3-d]pyridazin-5(6H)-one;
(S)-3-(3,5-dimethylphenyl)-6-(3-fluoro-5-hydroxyphenyl)-4-((methyl(pyrrolidin-2-ylmethyl)amino)methyl)pyrido[2,3-d]pyridazin-5(6H)-one;
(S)-3-(3,5-dimethylphenyl)-6-(3-hydroxy-5-(trifluoromethyl)phenyl)-4-((methyl(pyrrolidin-2-ylmethyl)amino)methyl)pyrido[2,3-d]pyridazin-5(6H)-one;

(S)-3-(3-(3,5-dimethylphenyl)-4-((methyl(pyrrolidin-2-ylmethyl)amino)methyl)-5-oxopyrido[2,3-d]pyridazin-6(5H)-yl)-5-hydroxybenzonitrile;

(S)-3-(3,5-dimethylphenyl)-6-(3-fluoro-5-hydroxyphenyl)-4-((methyl(pyrrolidin-2-ylmethyl)amino)methyl)pyrido[2,3-d]pyridazin-5(6H)-one;

(S)-3-(3-chloro-5-methoxyphenyl)-6-(3-fluoro-5-hydroxyphenyl)-4-((methyl(pyrrolidin-2-ylmethyl)amino)methyl)pyrido[2,3-d]pyridazin-5(6H)-one;

or a pharmaceutically acceptable salt, pharmaceutically acceptable solvate, diastereomeric mixture, or individual enantiomers thereof.

21. A pharmaceutical composition comprising a compound of claim 1, or a pharmaceutically acceptable salt, pharmaceutically acceptable solvate, diastereomeric mixture, or individual enantiomers thereof, and at least one pharmaceutically acceptable excipient.

22. A method of treating a disease or condition in a mammal that would benefit from the modulation of somatostatin receptor activities comprising administering a compound as described in claim 1, or a pharmaceutically acceptable salt, pharmaceutically acceptable solvate, diastereomeric mixture, or individual enantiomers thereof, to the mammal in need thereof wherein the disease or condition is selected from the group consisting of acromegaly, neuroendocrine tumor and pain.

* * * * *

UNITED STATES PATENT AND TRADEMARK OFFICE
CERTIFICATE OF CORRECTION

PATENT NO. : 9,957,267 B2
APPLICATION NO. : 15/186086
DATED : May 1, 2018
INVENTOR(S) : Yunfei Zhu et al.

Page 1 of 1

It is certified that error appears in the above-identified patent and that said Letters Patent is hereby corrected as shown below:

In the Specification

• Column 1, Lines 13-16:
"This invention was made with the support of the United States government under SBIR Grant No. 1R43DK088501-01A1, 1R44NS092231-01, 2R44DK088501-02A1, and 1R43EY024185-01 by the National Institutes of Health." should read -- This invention was made with government support under grant numbers DK088501, NS092231, and EY024185 awarded by the National Institutes of Health. The government has certain rights in the invention. --.

In the Claims

• Claim 1: Column 98, Line 8:
"$C_1$-$C_6$ alkyl, and unsubstituted" should read -- $C_1$-$C_6$ alkyl, unsubstituted --.

• Claim 12: Column 104, Lines 2-3:
"—CN, —OH," should read -- —CN, or —OH, --.

Signed and Sealed this
Thirtieth Day of June, 2020

Andrei Iancu
*Director of the United States Patent and Trademark Office*